(12) United States Patent
Hakamata

(10) Patent No.: US 6,760,058 B2
(45) Date of Patent: Jul. 6, 2004

(54) METHOD AND APPARATUS FOR PHOTOGRAPHING FLUORESCENT AND REFLECTED-LIGHT IMAGES

(75) Inventor: Kazuo Hakamata, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 433 days.

(21) Appl. No.: 09/837,764

(22) Filed: Apr. 19, 2001

(65) Prior Publication Data

US 2002/0018649 A1 Feb. 14, 2002

(30) Foreign Application Priority Data

Apr. 19, 2000 (JP) .......................................... 2000-117439
Jun. 9, 2000 (JP) .......................................... 2000-174165

(51) Int. Cl.[7] ............................ H04N 13/00; A61B 1/06
(52) U.S. Cl. ............................................ 348/45; 600/160
(58) Field of Search ............................ 348/222, 207.1, 348/207.11, 207.2, 207.99, 172, 45, 65, 76, 40, 42, 169; 600/476, 488, 477, 160; 382/274, 299, 289

(56) References Cited

U.S. PATENT DOCUMENTS

| | | |
|---|---|---|
| 4,762,391 A | 8/1988 | Margolin |
| 4,868,645 A | 9/1989 | Kobayashi |
| 4,951,135 A | 8/1990 | Sasagawa et al. |
| 5,528,059 A | 6/1996 | Isogai |
| 5,749,830 A | 5/1998 | Kaneko et al. |
| 5,833,617 A | 11/1998 | Hayashi |
| 5,909,244 A | 6/1999 | Waxman et al. |
| 6,316,215 B1 * | 11/2001 | Adair et al. .................. 435/29 |
| 2003/0191368 A1 * | 10/2003 | Wang et al. ................ 600/160 |

FOREIGN PATENT DOCUMENTS

| | | |
|---|---|---|
| EP | 0 655 860 A1 | 5/1995 |
| EP | 0 792 062 A2 | 8/1997 |
| FR | 2 548 497 | 1/1985 |

* cited by examiner

Primary Examiner—Chris Kelley
Assistant Examiner—Behrooz Senfi
(74) Attorney, Agent, or Firm—Sughrue Mion, PLLC

(57) ABSTRACT

A photographing method and apparatus for photographing a fluorescent image, composed of fluorescent light emitted by a living tissue that has been illuminated by a stimulating light, as an image having a higher S/N ratio. Fluorescent light emitted by a living tissue that has been illuminated by a stimulating light emitted from a light source and propagated along an endoscope enters an image fiber. The fluorescent light entering the image fiber is propagated along the image fiber to the output face of the image fiber and focused on the light-receiving zone of a photographing element, under photographing conditions set so that the relation between the pixels of aforementioned output face, upon which the fluorescent image is formed, to the pixels receiving the light of the fluorescent image within aforementioned light-receiving zone satisfies the condition expressed by the formula: Nf×4>Nd.

25 Claims, 35 Drawing Sheets

F I G. 2
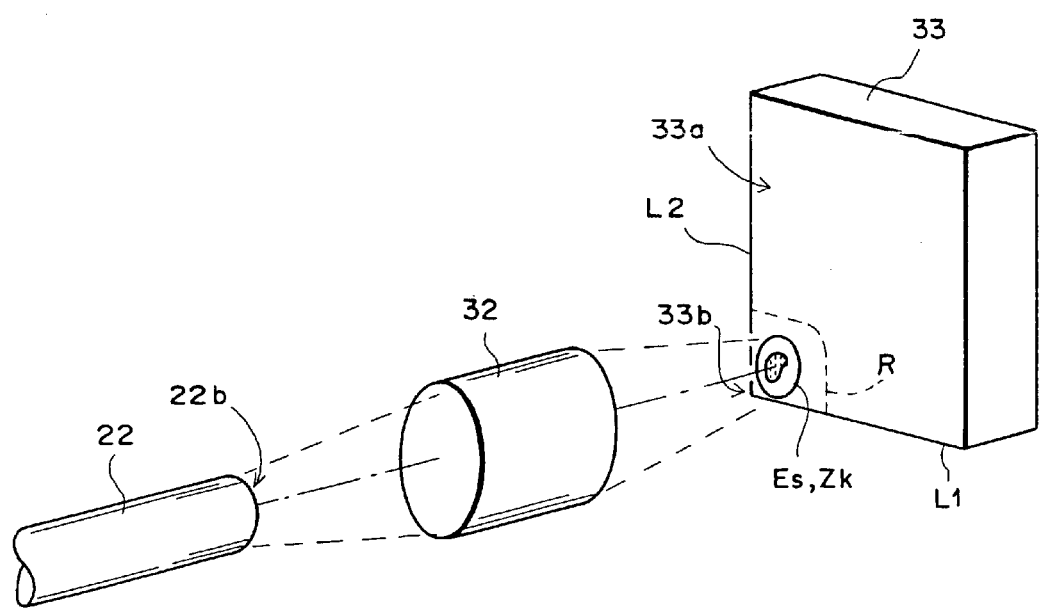

F I G. 3
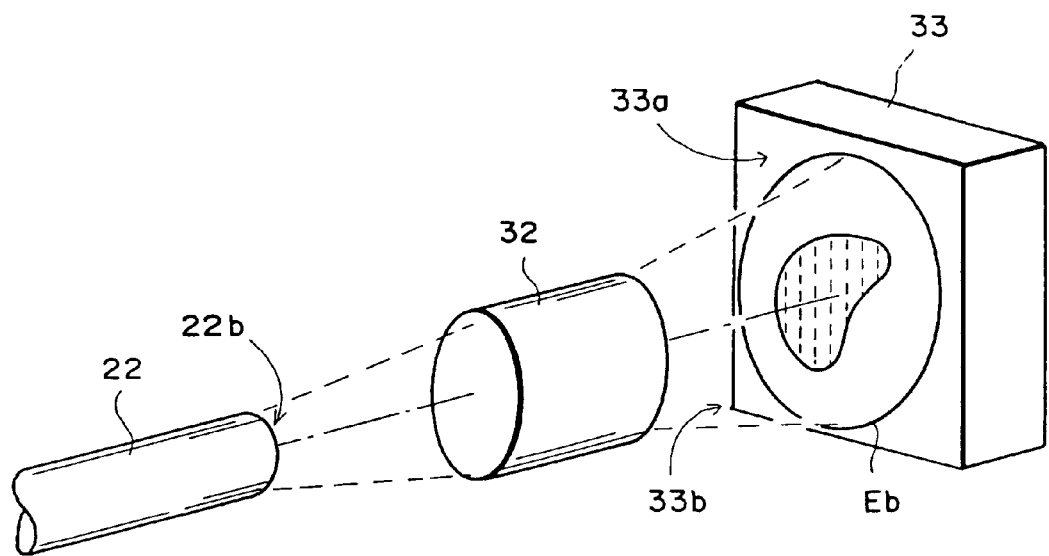

F I G. 7A
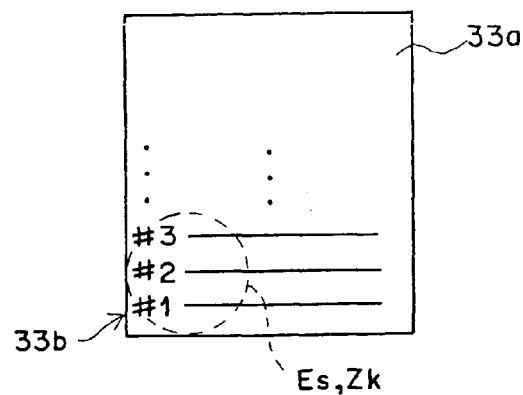
F I G. 7B
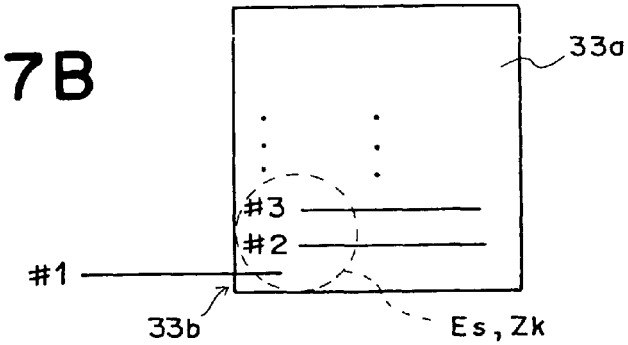
F I G. 7C
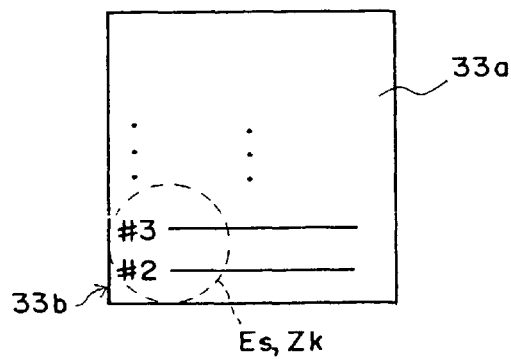
F I G. 7D
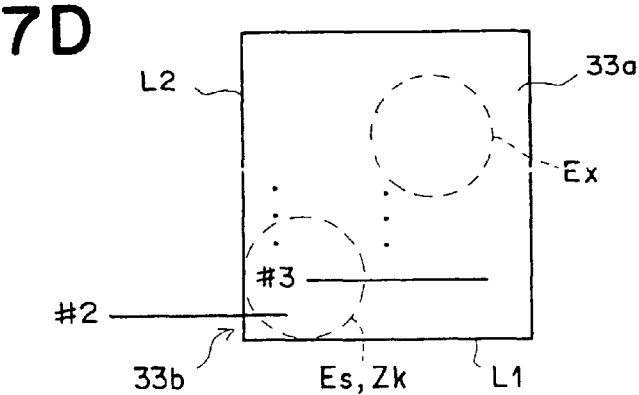

F I G . 11
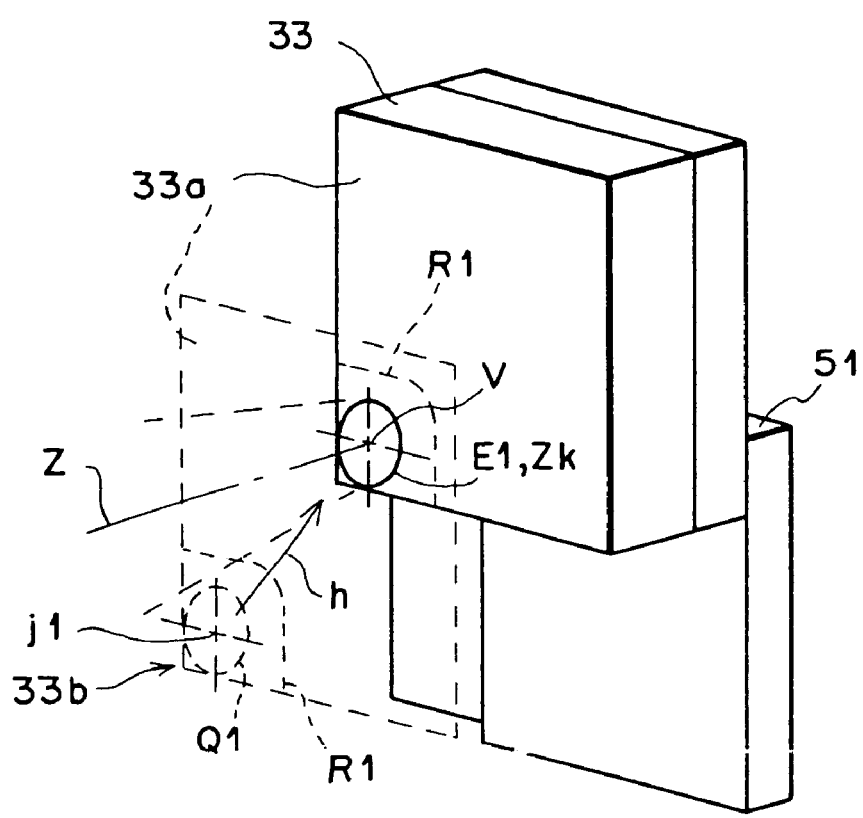

F I G . 12
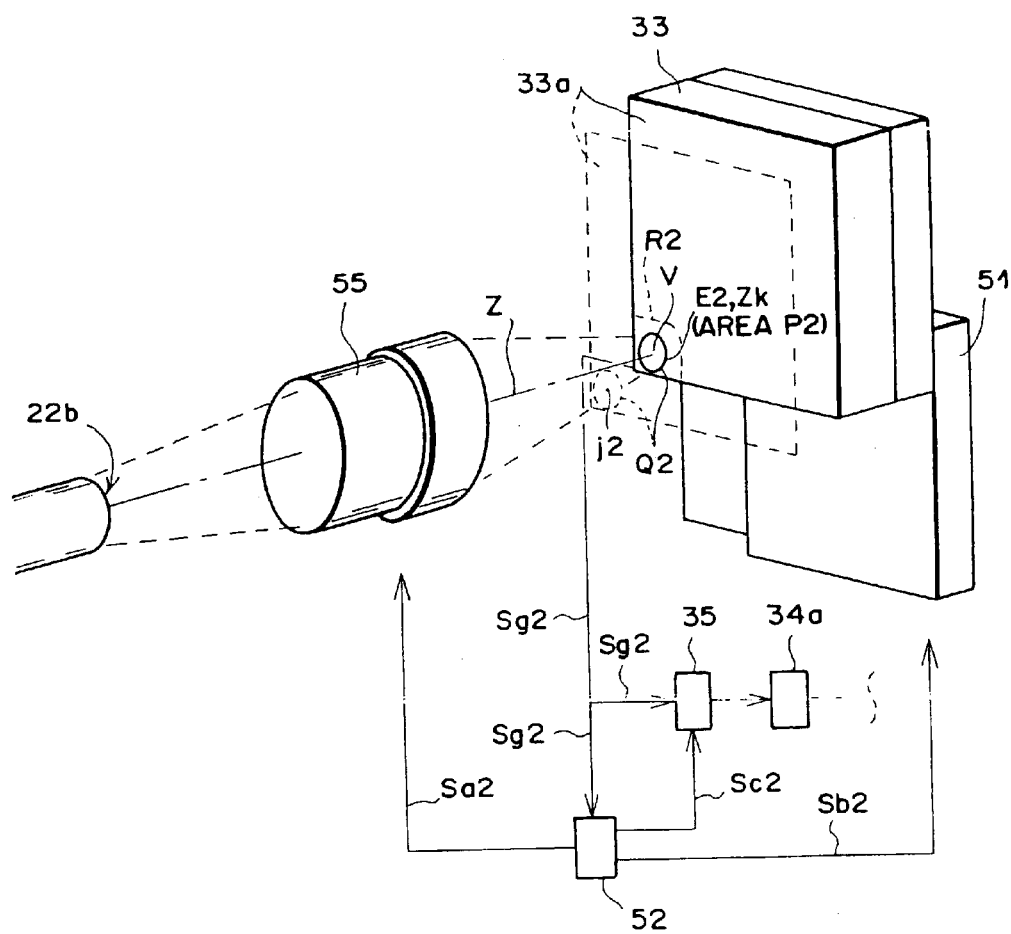

F I G . 13
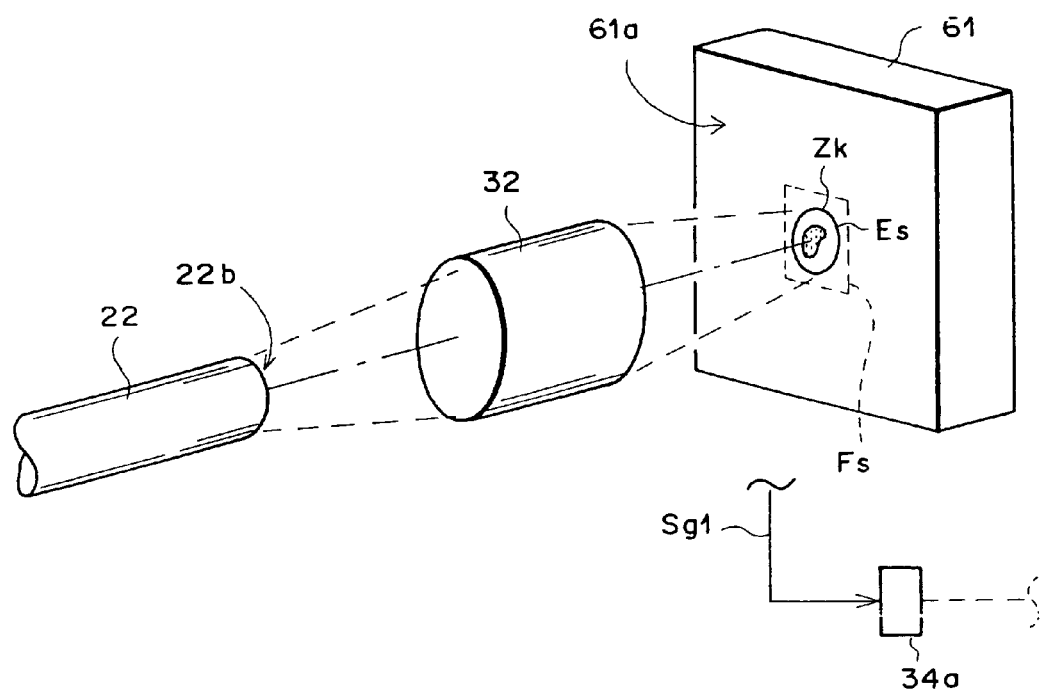

F I G . 14
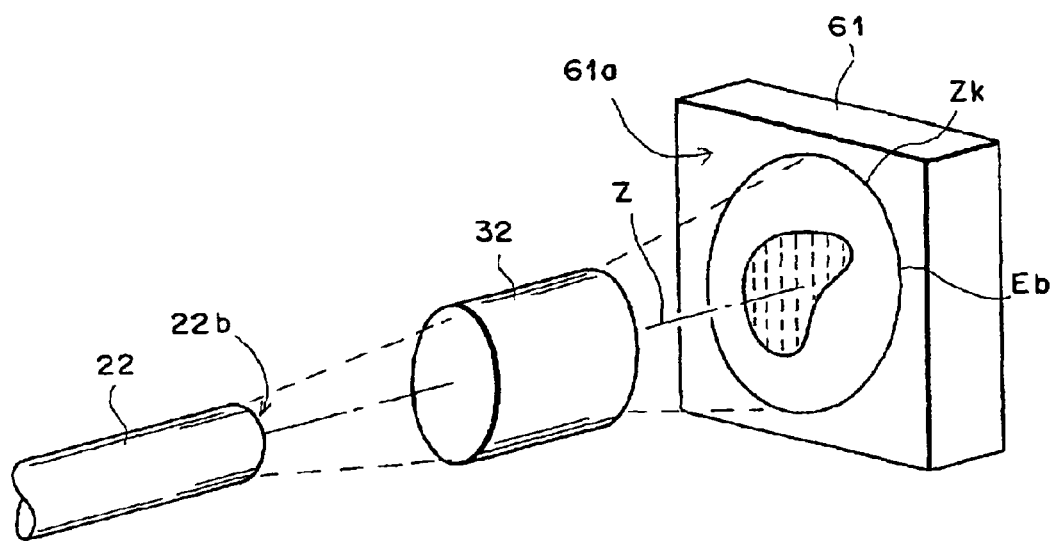

F I G . 16
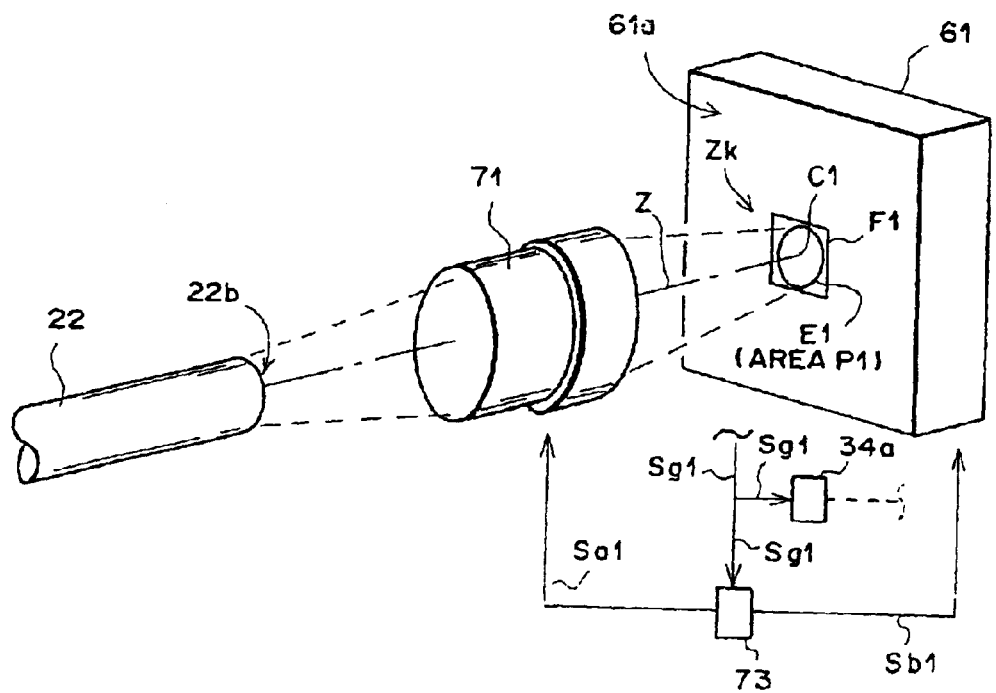

F I G . 17
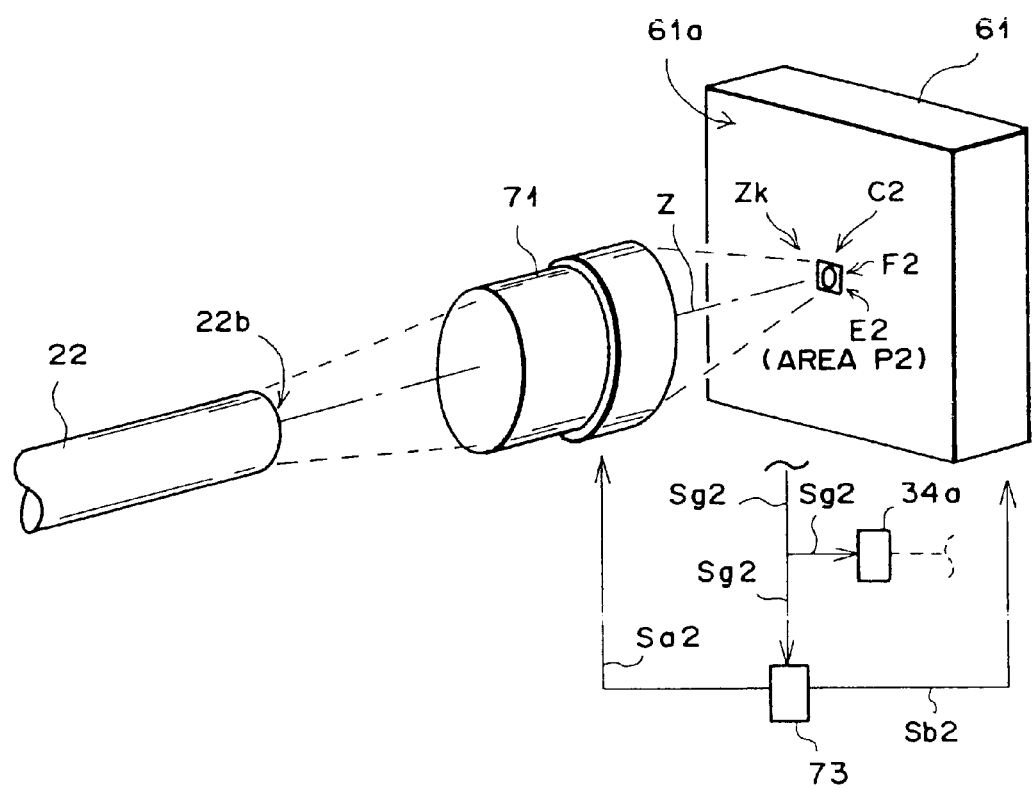

F I G. 23
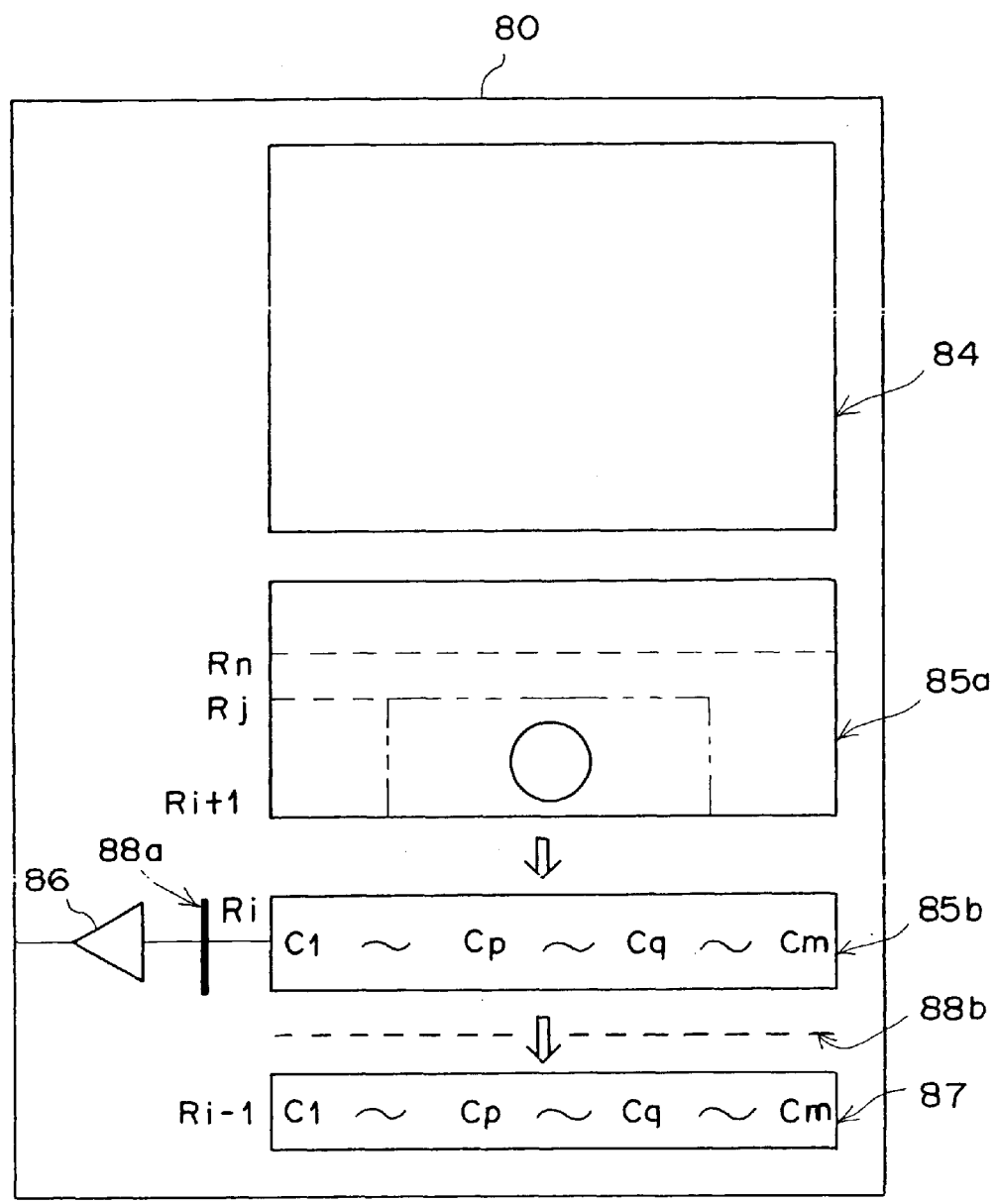

F I G . 26
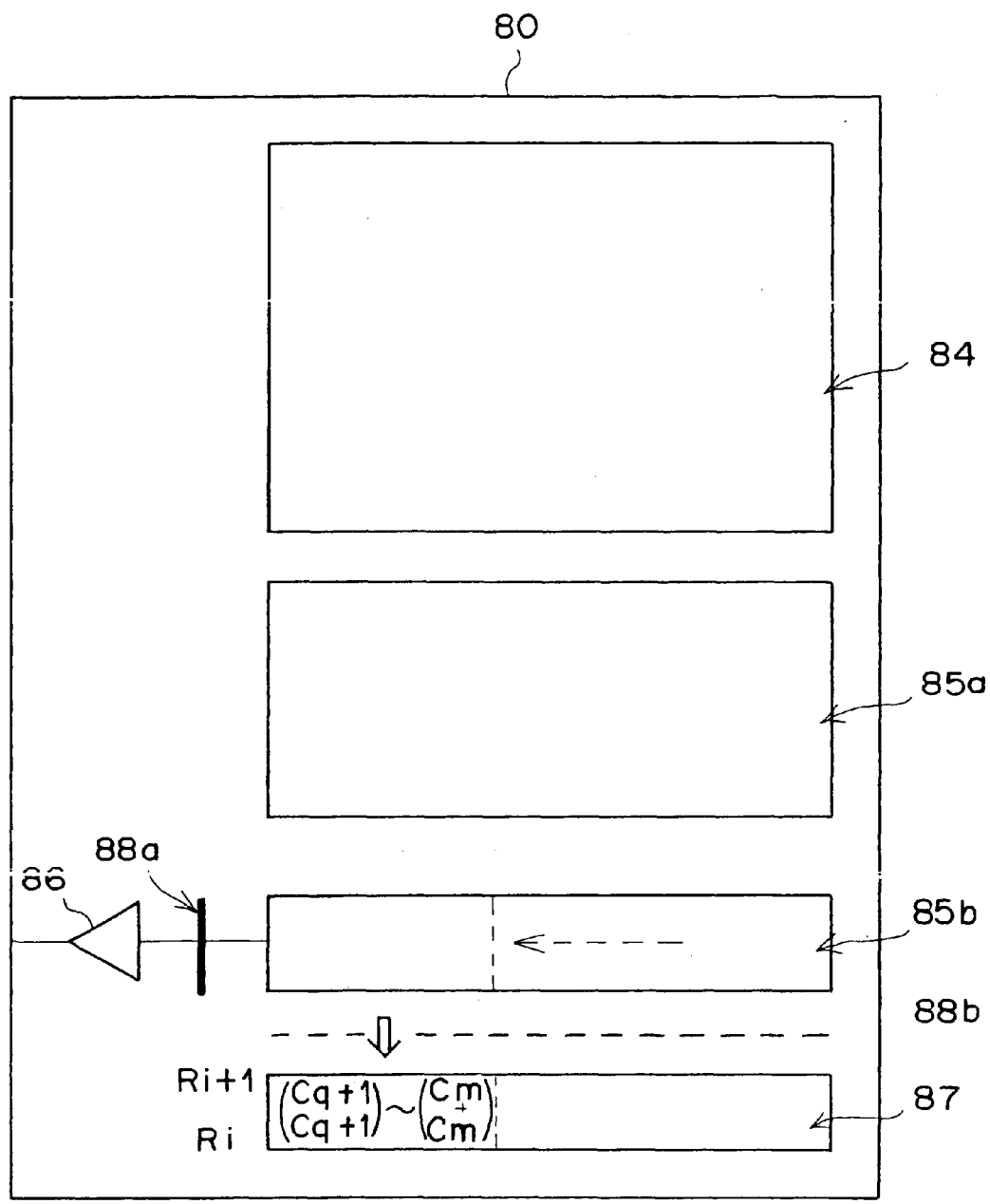

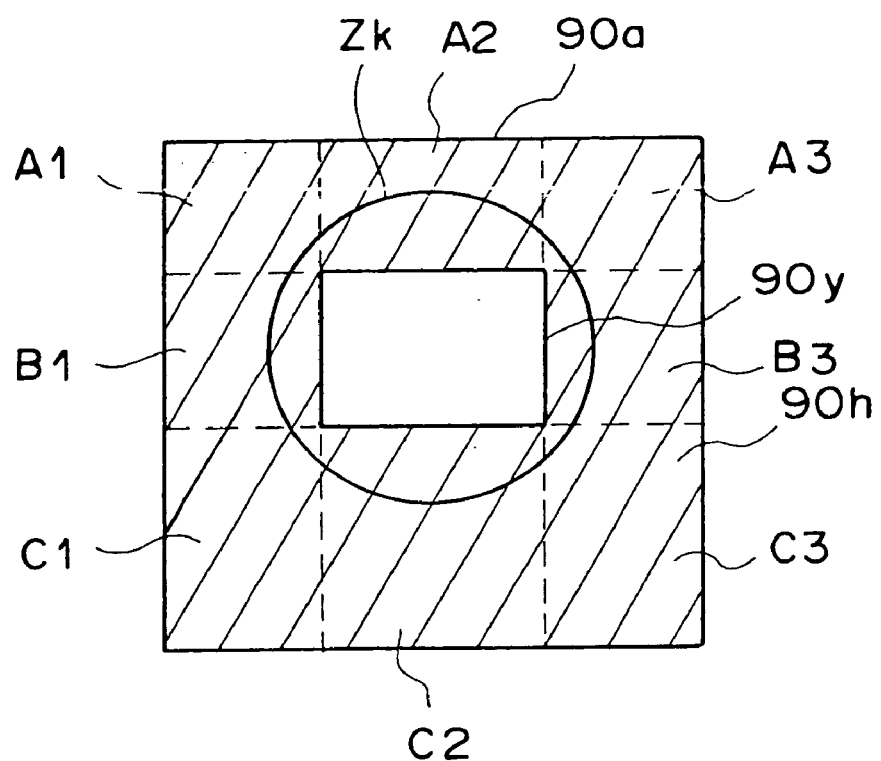
F I G . 35

METHOD AND APPARATUS FOR PHOTOGRAPHING FLUORESCENT AND REFLECTED-LIGHT IMAGES

BACKGROUND OF THE INVENTION

1. Field of the Invention

The present invention relates generally to a photographing method and apparatus, and more particularly to a photographing method and apparatus for photographing a fluorescent image of the fluorescent light emitted by a subject and a reflected light-image, etc. of a subject illuminated by a faint light.

2. Description of the Related Art

There has been expressed a desire for photographing a fluorescent image of the fluorescent light emitted by a subject and a reflected-light image of a subject illuminated by a faint light as clear images, and much discussion has ensued in regard to development of a high-sensitivity photographing system therefor.

For example, research has been conducted on an apparatus which, by analyzing fluorescent light-images obtained by photographing the fluorescent light emitted by the inherent dye of the structures of a living tissue illuminated by a stimulating light, facilitates the distinguishing of changes, etc. in the state of each type of disease. In a fluorescent endoscope, the image of the fluorescent light emitted by a subject is propagated along an image fiber and guided to the end thereof. The size of the image guided into the image fiber is magnified to a larger size than that at which it entered the image fiber, focused on a photographing element and photographed.

The fluorescent light emitted by the structures of a living tissue is faint, and a high-sensitivity photographing element is used to detect this light as an image. When the quantity of light received by the photographing element is large, the fluorescent image is photographed at the resolution corresponding to the number of pixels provided on the photographing element, however, when the quantity of light received by the photographing element is small, the signal charge of a plurality of pixels is multiplied, readout, subjected to a pixel binning processing, and the fluorescent image is photographed. For example, if an image fiber of a 2 mm diameter is constituted of 10,000 strands and the image formed by fluorescent light at the end of this fiber is formed of 10,000 pixels, the light-receiving zone of the photographing element for receiving this image is provided with 4 times the number of pixels (40,000 pixels or more). When, for example, the phosphor image received uses 25,000 or 38,000, etc. substantially all of the light-receiving zone of the photographing element, and when the quantity of fluorescent light received is small, the number of pixels to be subjected to pixel binning processing; that is, the number of pixels corresponding to 1 pixel is multiplied and increased, the quantity of light received corresponding to one pixel is increased and the resolution decreased, and conversely, when the quantity of fluorescent light received is large, the number of pixels to be subjected to pixel binning processing is reduced, the resolution increased and the image photographed.

More specifically, a desire has been expressed to obtain an image of a cancerous portion, which is located 50 mm away from the point on which the stimulated light is emitted, as an image signal having a S/N ratio of 1 or higher under standard photographing conditions, in which the structures of a living tissue are illuminated by a 120° wide, 100 mw stimulating light and exposed for $\frac{1}{30}$ of a second over the entire light-receiving zone.

When photographing is performed using a front-exposure type photographing element under aforementioned standard photographing conditions, because the normal charge of the image signal representing the fluorescent image of aforementioned cancerous portion stored on 1 pixel of the light-receiving zone is substantially 10 electrons, by controlling the sum of the number of electrons of the readout noise of each pixel of the light-receiving zone and the number of electrons of dark noise to 10 electrons or less, a S/N ratio of 1 or higher can be obtained for the image signal representing the fluorescent light-image of the cancerous portion. In addition, for cases in which a rear-exposure type photographing element, which has a quantum efficiency substantially twice that of aforementioned front-exposure photographing element, is used, because the charge of the image signal representing the fluorescent image stored on 1 pixel under the settings of aforementioned standard photographing conditions is substantially 20 electrons, by controlling the sum of the number of electrons of the readout noise of each pixel of the light-receiving zone and the number of electrons of dark noise to 20 electrons or less, a S/N ratio of 1 or higher can be obtained for the image signal representing the fluorescent light-image of the cancerous tissue.

However, even if the above described method of employing a processing such as pixel binning is used, when the signal charge that has been stored on a plurality of pixels receiving the fluorescent light the fluorescent image is multiplied within the photographing element, because the signal charge generated due to reception of fluorescent light is in the end simultaneously multiplied together with the signal charge stored due to the dark noise, even if the charge of the image signal stored on a plurality of pixels is grouped together as a unit by being subjected to pixel binning processing and are and treated as corresponding to 1 pixel, the ratio of the dark noise component is not reduced, and an improvement in the S/N ratio cannot be hoped for. At this point, a photographing system in which the S/N ratio can be improved by reducing the dark noise component is desired.

SUMMARY OF THE INVENTION

The present invention has been developed in consideration of the circumstances described above, and it is a primary object of the present invention to provide a faint light photographing method and apparatus in which, by reducing the dark noise, the light-image of a subject can be photographed as an image having a high S/N ratio.

According to the photographing method of the present invention, in which fluorescent light emitted by a living-tissue subject illuminated by stimulating light enters an image fiber and is guided toward the output face of the image fiber, and the fluorescent image formed at the output face of the image fiber is focused on the light-receiving zone of the photographing element and photographed by the photographing element, the relationship between the number of pixels Nf forming the fluorescent image on the output face of the image fiber and the number of pixels Nd receiving the light of the fluorescent image assembled within the light-receiving zone of the photographing element satisfy the condition expressed by the formula: Nf×4>Nd.

For cases in which a front-exposure type photographing element is used, at normal temperature or lower, it is preferable that the fluorescent image be photographed under photographing conditions set so that the sum of the number of electrons of the readout noise produced on each pixel within the light-receiving zone receiving the light of a fluorescent image and the number of electrons of dark noise be 10 or less.

For cases in which a rear-exposure type photographing element is used, at normal temperature or lower, it is preferable that the fluorescent image be photographed with the photographing conditions set so that the sum of the number of electrons of the readout noise produced on each pixel within the light-receiving zone receiving the light of a fluorescent image and of dark noise be 20 or less.

It is preferable that the fluorescent image be focused on an imaged focusing means in which the number of pixels of the light-receiving zone receiving the light of the fluorescent image is 40,000 or less.

For cases in which the photographing element is capable of reading out, in a random manner, the signal charge stored on each pixel, it is preferable that a readout zone narrower than the light-receiving zone and which includes the fluorescent image is set within the light-receiving zone, and that readout of the readout zone be performed prior to readout of other zones within the light-receiving zone.

For cases in which the photographing element reads out the signal charge stored on each pixel sequentially, it is preferable that the fluorescent image be assembled at the closest position to the readout port of the photographing element, within the light-receiving zone.

A photographing apparatus according to the present invention comprises an optical system for directing fluorescent light emitted from a living-tissue subject illuminated by stimulating light into an image fiber and guiding it to the output face of the image fiber, an image focusing means for focusing on the light-receiving zone of the photographing element the fluorescent image formed by the fluorescent light guided to the output face of the image fiber, and a photographing means for photographing the fluorescent image assembled at the light-receiving zone thereof, wherein the relationship between the number of pixels Nf forming the fluorescent image on the output face of the image fiber and the number of pixels Nd receiving light of the fluorescent image assembled within the light-receiving zone of the photographing element satisfy the condition expressed by the formula: $Nf \times 4 > Nd$.

For cases in which the photographing element of the photographing means is provided as a front-exposure type photographing element, at normal temperature or lower, it is preferable that the fluorescent image be photographed under photographing conditions set so that the sum of the number of electrons of the readout noise produced on each pixel within the light-receiving zone receiving the light of a fluorescent image and the number of electrons of dark noise be 10 or less.

For cases in which the photographing element of the photographing means is provided as a rear-exposure type photographing element, at normal temperature or lower, it is preferable that the fluorescent image be photographed under photographing conditions set so that the sum of the number of electrons of the readout noise produced on each pixel within the light-receiving zone receiving the light of a fluorescent image and the number of electrons of dark noise be 20 or less.

It is preferable that the fluorescent image be focused on an imaged focusing means in which the number of pixels of the light-receiving zone receiving the light of the fluorescent image is 40,000 or less.

The image focusing means can be a means capable of changing, corresponding to the quantity of fluorescent light received by the photographing element, the size of the fluorescent image assembled within the light-receiving zone thereof.

The image focusing means is provided with a zooming optical system, and by use of the zooming optical system, can be a means capable of changing the size of the fluorescent image assembled within the light-receiving zone thereof.

The photographing apparatus can also be a photographing element that changes the readout frequency of the photographing element, corresponding to the zooming rate of the zooming optical system.

For cases in which the photographing element is capable of reading out in a random manner the image signal charge stored on each pixel, it is preferable that the photographing means be provided with a readout control means for setting a readout zone narrower than the light-receiving zone and which includes the fluorescent image within the light-receiving zone, and causing readout of the readout zone to be performed prior to readout of other zones within the light-receiving zone.

For cases in which the photographing element is capable of reading out in a random manner the image signal charge stored on each pixel, it is preferable that the photographing means be provided with a readout control means for setting a readout zone narrower than the light-receiving zone and which includes the fluorescent image within the light-receiving zone, which is also capable of changing the size of the readout zone and causing readout of the readout zone to be performed before readout of other zones within the light-receiving zone.

For cases in which the photographing element is a photographing element that sequentially reads out the image signal charge stored on each pixel, it is preferable that the photographing element is structured so that the fluorescent image is assembled at the closest position to the readout port of the photographing element, within the light-receiving zone.

For cases in which the photographing element is a photographing element that sequentially reads out the image signal charge stored on each pixel, it is preferable that the photographing element be provided with an focusing-position changing means for changing the position at which the fluorescent image is assembled within the light-receiving zone.

According to a photographing method of the present invention: a photographing element in which the charge stored on each pixel is sequentially transferred and readout is utilized; the light-image of the subject is focused on the light-receiving zone of the photographing element; the assembled light-image is photoelectrically converted on each light-receiving pixel within the light-receiving zone and stored within each light-receiving pixel as an image charge; and the signal charge stored within each light-receiving pixel is converted to an image signal and readout. In addition, the light-image is focused on the light-receiving pixels of a readout zone formed from less than the total number of pixels of the light-receiving zone, and the readout signal charge transferred to and stored on the light-receiving pixels contained within the readout zone is readout as aforementioned image charge and the residual signal charge transferred to and stored on the light-receiving pixels outside the readout zone in the non-readout zone is readout as a null change.

According to aforementioned photographing method, the sequentially transferred readout signal charge can be subjected to binning processing before it is readout.

According to another photographing method of the present invention: a photographing element in which the charge stored on each pixel is sequentially transferred and readout is utilized; the light-image of the subject is focused on the light-receiving zone of the photographing element; the assembled light-image is photoelectrically converted on each light-receiving pixel within the light-receiving zone and stored within each light-receiving pixel as an image charge; and the signal charge stored within each light-receiving pixel is converted to an image signal and readout. In addition, the light-image is focused on the light-receiving pixels of a readout zone formed from less than the total number of pixels of the light-receiving zone, and the readout signal charge transferred to and stored on the light-receiving pixels contained within the readout zone is readout as aforementioned image charge and the residual signal charge transferred to and stored on the light-receiving pixels outside the readout zone in the non-readout zone is discarded through a clearing drain.

According to a further photographing method of the present invention: a photographing element in which the charge stored on each pixel is sequentially transferred and readout is utilized; in which the light-image of the subject is focused on the light-receiving zone of the photographing element; the assembled light-image is photoelectrically converted on each light-receiving pixel within the light-receiving zone and stored within each light-receiving pixel as an image charge; and the signal charge stored within each light-receiving pixel is converted to an electric image signal and readout. In addition, the light-image is focused on the light-receiving pixels of a readout zone formed from less than the total number of pixels of the light-receiving zone, and after the readout signal charge transferred to and stored on the light-receiving pixels contained within the readout zone is readout as aforementioned image charge, the residual signal charge transferred to and stored on the light-receiving pixels outside the readout zone in the non-readout zone, or aforementioned residual signal charge and the image signal charge stored on the light-receiving pixels contained within the light-receiving zone after the readout signal charge has been read out are grouped together and read out as null for each block or one pixel at a time.

A photographing apparatus according to the present invention comprises a photographing element and an image focusing means for focusing the light-image of a subject in the light-receiving zone of the photographing element. The photographing element is provided with a photoelectric converting portion for photoelectrically converting and accumulating as an image signal the received light on each light-receiving pixel within the light-receiving zone, a charge transfer portion for sequentially transferring the image charge stored on each light-receiving pixel, and a sequential-readout portion for converting the sequentially transferred image charge to an electric image signal and reading out said image charge, wherein said image focusing means focuses the light-image on the light-receiving pixels of a readout zone formed from less than the total number of pixels of the light-receiving zone, and a sequential-readout control means is provided for controlling the readout as an image signal of the readout charge stored on the light-receiving pixels of the readout zone by the sequential-readout portion and the readout as null of the residual signal charge stored on the light-receiving pixels outside the readout zone in the non-readout zone by the sequential-readout portion.

Aforementioned photographing apparatus can be provided with a gate between the charge transfer portion and the sequential-readout portion for controlling passage of the signal charge from the charge transfer portion to the sequential-readout portion, and a gate control means for controlling aforementioned gate so as to facilitate the subjecting of said readout signal charge to binning processing before the readout signal charge is transferred by the charge conversion portion and read out by the sequential-readout portion.

A further photographing apparatus according to the present invention comprises a photographing element and an image focusing means for focusing the light-image of the subject in the light-receiving zone of the photographing element, and the photographing element is provided with a photoelectric converting portion for photoelectrically converting and storing as an image signal the received light on each light-receiving pixel within the light-receiving zone, a charge transfer portion for sequentially transferring the image charge stored on each light-receiving pixel, and a sequential-readout portion for converting the sequentially transferred image charge to an electric image signal and reading out said image charge, wherein said image focusing means focuses the light-image on the light-receiving pixels of a readout zone formed from less than the total number of pixels of the light-receiving zone, and is further provided with a clearing drain for discarding the signal charge sequentially transferred by the charge transfer portion, and a sequential-readout control means for controlling readout of the readout signal charge, which is stored on the light-receiving pixels of the readout zone, by the sequential readout means and the discarding of the residual signal charge, which is stored on the light-receiving pixels outside the readout zone in the non-readout zone, into the clearing drain.

A still further photographing apparatus of the present invention comprises a first gate provided between the charge transfer portion and the sequential-readout portion for controlling passage of the signal charge from the charge transfer portion to the sequential-readout portion, a second gate provided between the charge transfer portion and aforementioned clearing drain for controlling passage of the signal charge from the charge transfer portion to the clearing drain, and a gate control means for controlling gate 1 and gate 2 so as to facilitate the subjecting of the readout signal charge to binning processing before the readout signal charge is transferred by said charge conversion portion and read out by the sequential-readout portion.

Yet another photographing apparatus of the present invention comprises a photographing element and an image focusing means for focusing the light-image of the subject in the light-receiving zone of the photographing element, and the photographing element is provided with a photoelectric converting portion for photoelectrically converting and accumulating as an image signal the light received on each light-receiving pixel within the light-receiving zone, a pixel selecting means capable of randomly selecting pixels from among the light-receiving pixels, and a random readout portion for photoelectrically converting the signal charge of the selected light-receiving pixels to an electric image signal and reading it out, wherein the image focusing means focuses the light-image on the light-receiving pixels of a readout zone formed from less than total number of pixels of the light-receiving zone, and the pixel selecting portion selects light-receiving pixels of the readout zone, and after the random readout portion reads out the image charge stored on the selected light-receiving pixels, the pixel selecting means selects light-receiving pixels contained in the non-readout zone outside the readout zone, or the pixels contained in the non-readout zone and the readout zone, and a random readout control means is provided to control the pixel selecting portion and the random readout portion so as to facilitate readout as a null change for each block or one pixel at a time by the random readout means of the residual signal charge stored on the light-receiving pixels in the non-readout zone or aforementioned residual signal charge grouped together with the image signal charge stored on the light-receiving pixels contained within the light-receiving zone.

According to the random readout control means, at the same time a plurality of light-receiving pixels within the light-receiving zone are selected by the pixel selecting means, binning processing can be performed on the readout signal charge so that the multiplied signal charge of each readout signal charge stored on the selected light-receiving pixels can be converted to an electric image signal and readout.

According to aforementioned photographing apparatus, the image focusing means is provided with a zooming optical system, and said zooming optical system can be a means capable of changing the size of the light image focused on the light-receiving zone.

The photographing apparatus can also be a photographing element that changes the readout frequency of the photographing element, corresponding to the zooming rate of the zooming optical system.

Aforementioned photographing apparatus can be loaded in a fluorescent endoscope.

According to the photographing method and apparatus described above, the photographing element can be a charge amplification type for amplifying the charge by impact ionization.

Note that the "charge-amplification type photographing element" for amplifying the charge by impact ionization is a photographing element having a shift-resistor provided with a charge amplifying function and which is disposed between the horizontal CCD readout shift-resistor and the output amplifier. The operating principle by which the shift-resistor provided with a charge amplifying function amplifies the charge is the impact ionization phenomenon, which forms 2-dimensional electrons, occurring when the signal charge is transferred in deep potential formed at a sufficient strength (the charge collides with Si, and electron holes are formed). By transferring the signal charge, which has been transferred from the horizontal readout shift-resistor, by the multi-step shift-resistors of the shift-resistor provided with a charge amplifying function, each having deep potential, the 2-dimensional electrons are repeatedly formed, the readout noise level is not substantially increased and the signal charge is amplified. In relation to this charge-amplification type photographing element for amplifying a charge by use of impact ionization, refer to the specification of U.S. Pat. No. 5,337,340 (name of invention: Charge Multiplying Detector <CMD> suitable for small pixel CCD image sensor).

According to the photographing method and apparatus of the present invention, in photographing of a fluorescent image focused on the light-receiving zone of the photographing element, because the fluorescent image is focused on the light-receiving zone wherein the relationship of the pixels Nf, which represent the fluorescent image formed on the output face of the image fiber, to the pixels Nd, which are the pixels in the light-receiving zone receiving the light of the fluorescent image assembled therein, satisfies the condition expressed by the formula: Nf×4>Nd. That is, because the number of pixels of the light-receiving zone of the photographing element focusing the fluorescent image formed at the output face of the image fiber has been kept not unnecessarily high, the quantity of dark noise produced per each pixel is not changed and quantity of fluorescent light received per pixel is increased, and because the fluorescent image, having a relatively reduced ratio of dark noise, can be read out from the photographing element, the fluorescent image can be photographed as an image having a high S/N ratio.

Note that for cases in which a front-exposure type photographing element is used, if the photographing conditions are set so that the sum of the number of noise and dark noise electrons produced on each pixel in the light-receiving zone receiving the light of the fluorescent image, at normal temperature or lower, is 10 or less, in aforementioned standard photographing state, an image of a cancerous tissue, for example, can be photographed having an S/N ratio of 1 or higher.

In addition, for cases in which a rear-exposure type photographing element is used, if the photographing conditions are set so that the sum of the number of noise and dark noise electrons produced on each pixel in the light-receiving zone receiving the light of the fluorescent image at normal temperature or lower is 20 or less, because the quantum efficiency of a rear-exposure photographing element becomes twice that of a front-exposure photographing element, in aforementioned standard photographing state, an image of a cancerous tissue, for example, can be photographed having an S/N ratio of 1 or higher.

Further, if the fluorescent image is assembled and photographed in a light-receiving zone in which and the number of pixels receiving the light of the fluorescent image is 40,000 or less, even for cases, for example, in which there are sufficiently plentiful pixels to represent the image formed at the output face of the image fiber, there are not an excess number of unnecessary pixels receiving the light of the fluorescent image in the light-receiving zone, and by controlling the number of pixels receiving the light of the fluorescent image to 40,000 or less, which is a number of pixels providing for the capability for distinguishing the change, etc. in the state of diseased tissues of various diseases by analyzing the photographed fluorescent image, a fluorescent image in which the quantity of light received per pixel is further increased can be read out from the photographing element, and the fluorescent image can be photographed as an image with a higher S/N ratio.

Further yet, if the size of the fluorescent image focused on the photographing element is changed, corresponding to the amount of light received at the photographing element, by use of a zooming optical means, etc., in a case, for example, when the quantity of received light of the fluorescent image is small, the fluorescent image is assembled small on the photographing element, and by photographing the fluorescent image by use of few pixels, the quantity of light received per pixel increases and the resolution of the image deteriorates, and for cases in which the quantity of received light of the fluorescent image is large, the fluorescent image assembled large on the photographing element, and by photographing the fluorescent image by use of many pixels, because adjustment can be made so that the quantity of received light is ensured while increasing the resolution, the fluorescent image can be photographed as an image having both the appropriate quantity of received-light and resolution.

Still further, if the photographing element is provided so that it is capable of reading out, in a random manner, the image charge stored on each pixel and with a readout zone including the fluorescent image and narrower than the light-receiving zone, if readout of the readout zone is performed prior to readout of the other zones, the time for dark noise to accumulate on each pixel of the readout zone, which are read out before the pixels of the other zones, can be shortened, and the fluorescent image can be read out as an image having a high S/N ratio.

Further still, if the photographing element is provided so as to sequentially read out the signal charge stored on each pixel and assemble the fluorescent image at the point closest to the readout port of the photographing element within the light-receiving zone thereof, compared to other cases, because the light of the fluorescent image received at each pixel is read out faster and the time for dark noise to accumulate can be reduced, the fluorescent image can be photographed as an image having a higher S/N ratio.

In addition, if the photographing element is provided so that it is capable of reading out, in a random manner, the signal charge stored on each pixel, and a readout zone, which is read out prior to other zones and whose size it is possible to change, is set within the light-receiving zone of the photographing element, in a case, for example, in which the size of an image to be assembled is changed corresponding to the quantity of received light, the position at which the fluorescent image is to be assembled can be set close to aforementioned readout port corresponding to the change in size thereof, by which efficient early readout of the fluorescent image becomes possible, and the fluorescent image can be photographed as an image having a higher S/N ratio.

Further, if the photographic element is provided so that it sequentially reads out the signal charge stored on each pixel, and so that it is possible to change the position at which the fluorescent image is assembled within the light-receiving zone thereof, in a case, for example, in which the size of an image to be assembled is changed corresponding to the quantity of received light, the position at which the fluorescent image is to be assembled can be set close to aforementioned readout port corresponding to the change in size thereof, by which efficient early readout of the fluorescent image becomes possible, and the fluorescent image can be photographed as an image having a higher S/N ratio.

According to a photographing method and apparatus of the present invention, a photographing element for sequentially transferring and reading out the signal charge stored on each pixel is utilized, and in converting the signal charge stored in each pixel to an electric image signal and reading out said image signal, the light-image is focused on the light-receiving pixels of a readout zone formed from less than the total number of pixels of the light-receiving zone, and accompanying the conversion and readout of the readout signal charge, which has been transferred to and stored on the light-receiving pixels contained within the readout zone, as an image charge, because the residual signal charge transferred to and stored on the light-receiving pixels outside the readout zone in the non-readout zone has been read out as null, the quantity of dark noise produced per each pixel is not changed and quantity of fluorescent light received per pixel can be increased twofold or greater, and because the ratio of dark noise of the fluorescent image can be relatively reduced, the fluorescent image can be photographed as an image having a high S/N ratio.

Note that upon converting the signal charge stored on each light receiving pixel image signal charge and reading out said image signal, the light-image of the subject is focused in a readout zone formed of a number of light-receiving pixels equal to less than half of the total number of light-receiving pixels of the light-receiving zone. Accompanying the conversion to an image signal of the readout signal charge that has been transferred to the readout zone and readout of said image signal, if the residual signal charge that has been transferred to and stored on the light-receiving pixels of the no-readout zone outside of the readout zone is read out as a null change, because the quantity of dark noise produced per pixel does not change and the quantity of light received per pixel can be increased by more than double and the ratio of dark noise can be relatively reduced, the light-image can be photographed as an image having a higher S/N ratio.

According to another photographing method and apparatus of the present invention, a photographing element for sequentially transferring and reading out the signal charge stored on each pixel is utilized, and in converting the signal charge stored in each pixel to an electric image signal and reading out said image signal, the light-image is focused on the light-receiving pixels of a readout zone formed from less than less of the total number of pixels of the light-receiving zone, and accompanying the conversion of the readout signal charge transferred to and stored on the light-receiving pixels contained within the readout zone to an image signal and readout of said image signal, because the residual signal charge transferred to and stored on the light-receiving pixels outside the readout zone in the non-readout zone has been discarded via a clearing drain, the quantity of dark noise produced per each pixel is not changed and quantity of fluorescent light received per pixel can be increased twofold or greater the quantity of dark noise produced per each pixel is not changed and quantity of fluorescent light received per pixel can be increased twofold or greater, the ratio of dark noise of the fluorescent image can be relatively reduced, and it is not necessary to convert the residual signal charge transferred to and stored on the light-receiving pixels outside the readout zone in the non-readout zone to an image signal and read out and discard the thus converted image signal as in the prior art, and because the residual signal charge transferred to and stored on the light-receiving pixels outside the readout zone in the non-readout zone has been discarded at a high speed via the clearing drain, the processing time for one section of the display is shortened, and readout of the signal charge stored in the readout zone can be completed rapidly, the quantity of dark noise can be further reduced with the passage of time and the fluorescent image can be photographed as an image having a high S/N ratio.

Note that upon converting the signal charge stored on each light receiving pixel image signal charge and reading out said image signal, the fluorescent image o the subject is focused in a readout zone formed of a number of light-receiving pixels equal to less than half of the total number of light-receiving pixels of the light-receiving zone. Accompanying the conversion to an image signal of the readout signal charge that has been transferred to the readout zone and readout of said image signal, if the residual signal charge that has been transferred to and stored on the light-receiving pixels of the no-readout zone outside of the readout zone is discarded via a clearing drain, the quantity of dark noise produced per pixel does not change, and by increasing the quantity of light received per pixel by more that double, the ratio of dark noise can be relatively reduced, and because the residual signal charge stored on the light-receiving pixels of the non-readout zone outside the readout zone is not converted to an image signal and readout and discarded as in conventional processing, but is discarded via a clearing drain at a high speed, readout of the signal charge of the readout zone can be completed rapidly, an because the quantity of dark noise, which accumulates with the passage of time, can be further reduced, the light image can be photographed as an image having a higher S/N ratio.

According to yet another photographing method and apparatus of the present invention, a photographing element for sequentially transferring and reading out the signal charge stored on each pixel is utilized, and in converting the signal charge stored in each pixel to an electric image signal and reading out said image signal, the light-image is focused on the light-receiving pixels forming the readout zone, which account for ½ or less of the total number of pixels of the light-receiving zone, and after readout of the readout signal charge stored on the light-receiving pixels contained within the readout zone as an image signal, because the residual signal charge stored on the light-receiving pixels contained in the non-readout zone outside the readout zone, or said residual signal charge together with the signal charge stored on the light-receiving pixels contained in said readout zone after readout of the readout signal charge have been read out from said random readout portion as null for each block or one pixel at a time, readout of the signal charge stored on the light-receiving pixels in the readout zone can be completed more rapidly and the quantity of dark noise, which accumulates with the passage of time, can be further reduced. Also, the blooming that occurs in cases in which the residual signal charge stored on the light-receiving pixels of the non-readout zone is not discarded, that is, the phenomenon wherein a signal charge continues to accumulate on the light-receiving pixels of the non-readout zone and overflows onto the light-receiving pixels of the readout zone can be prevented.

According to a still further readout method and apparatus of the present invention, employing a photographing element capable of reading out, in a random manner, the signal charge stored on each light-receiving pixel, upon conversion of the signal charge stored on each light-receiving pixel to an electric image signal and readout of said image signal, the light-image of the subject is focused in a readout zone formed of a number of light-receiving pixels equal to less than half of the total number of light-receiving pixels of the light-receiving zone, and after readout of the readout signal charge, as an image signal, stored on each of the light-receiving pixels of said readout zone, if the residual signal charge stored on the light-receiving pixels of the non-readout zone outside the readout zone, or said residual signal charge grouped together with the signal charge stored on the readout zone after the readout signal charge has been readout therefrom is readout as empty for each block or each pixel, readout of the signal charge stored on the light-receiving pixels of the readout zone can be completed more rapidly, and the quantity of dark noise, which accumulates with the passage of time, can be reduced. Further, the blooming occurring for cases in which discarding of the residual signal charge stored on the light-receiving pixels of the non-readout zone has not been performed, that is, the phenomenon wherein the signal charge continuing to be accumulated on the light-receiving pixels of the non-readout zone overflows onto the light-receiving pixels within the readout zone, can be prevented.

Further, if aforementioned readout signal charge is subjected to binning processing, because the signal charge stored on a plurality of pixels can be grouped together as a unit and converted to an image signal, the readout noise produced when a signal charge is converted to an electric image signal can be further reduced and image signal carrying the light-image of a subject can be photographed as an image having an even higher S/N ratio.

Still further, if the image focusing means is provided with a zooming optical means, by use of which it becomes a means capable of changing the size of the light-image to be focused on the light-receiving zone, for cases in which the quantity of light received from the light-image is insufficient and an image signal having a low S/N ratio is read out, by focusing the light image in a small area within the light-receiving zone, the quantity of light received per pixel is increased and the light-image can be read out as an image signal having a high S/N ratio. In addition, for cases in which the quantity of light received from the light-image is sufficiently large and an image signal having a high S/N ratio has been read out, by focusing the light-image on a larger area of the light-receiving zone, the number of light-receiving pixels receiving the light of the light-image is increased, and an image signal carrying a light-image having a higher resolution can be read out.

In addition, if the photographing apparatus is a photographing element that changes the readout frequency, corresponding to the zooming rate of the zooming optical system, the level of readout noise mixed in the images to be readout can be more precisely made to be low. That is to say, for cases in which a normal photographing element is used, because the quantity of readout noise produced is proportional to the horizontal base of the readout frequency, if the readout frequency is lowered, the quantity of readout noise can be caused to be low. For example, if the zooming rate of the zooming optical system is set low, and a predetermined observation zone is focused smaller on the photographing element and the number of readout pixels reduced, the readout frequency can be lowered by only the portion of the number of pixels read out for 1 frame and the quantity of readout noise produced can be precisely made to be small.

More specifically, for example, in a case in which a normal photographing element is employed under a photographing condition of 30 frames/second, the readout noise is more controlled than the dark noise, and reducing the readout noise becomes a means of improving the sensitivity (improving the S/N ratio). Because the quantity of readout noise produced is proportional to the horizontal base of the readout frequency, if the readout frequency is lowered, it is possible to raise the sensitivity (S/N). Here, if the predetermined observation zone is focused smaller on the photographing element by the zooming optical means and the number of pixels read out is reduced, the readout frequency can be lowered by only the portion of the number of pixels read out for 1 frame and the quantity of readout noise produced can be precisely made to be small. If the readout frequency becomes low, the quantity of readout noise produced is reduced, and the sensitivity (S/N) can be improved.

If the photographing apparatus is implemented in an endoscope apparatus, because the quantity of light received per pixel is increased and the dark noise can be reduced, a reflected light-image produced by the light reflected from inside a living-tissue subject illuminated by an illuminating light, the fluorescent light image produced by the fluorescent light emitted by a living-tissue subject illuminated by a stimulating light, etc. can be observed as a light-image having a high S/N ratio.

In addition, if the photographing apparatus is a charge-amplification type photographing element that amplifies the charge by impact ionization, the readout noise is lowered, and the signal charge can be read out as an image signal having an even higher S/N ratio.

BRIEF DESCRIPTION OF THE DRAWINGS

FIG. 2 shows a fluorescent image Zk focused on an area of the light-receiving zone of the photographing element smaller than the entire light-receiving zone, FIG. 3 shows a fluorescent image Zk focused on an area covering the entire light-receiving zone of the photographing element, FIGS. 7A, 7B, 7C and 7D show readout of an image signal from fluorescent image focusing zone Es set on the photographing element, FIG. 11 shows a fluorescent image light-receiving sector and fluorescent image focusing zone that have been matched, FIG. 12 shows a fluorescent image Zk focused on an area of the light-receiving zone of the photographing element smaller than the entire light-receiving zone, FIG. 13 is a schematic drawing of a fluorescent endoscope according to the third embodiment of the present invention, FIG. 14 shows a fluorescent image Zk focused on an area covering the entire light-receiving zone of the photographing element, FIG. 16 is a schematic drawing of a fluorescent endoscope according to the fourth embodiment of the present invention, FIG. 17 shows a fluorescent image Zk focused on an area of the light-receiving zone of the photographing element smaller than the entire light-receiving zone, FIG. 23 shows a state in which a signal charge has been discarded into the clearing drain, FIG. 26 shows the excess signal charge discarded into the clearing drain at an intermediate stage of the reading out of signal charge of horizontal line 1, FIG. 35 shows an example of the settings for each block when the residual signal charge is read out for each block.

DESCRIPTION OF THE PREFERRED EMBODIMENTS

Figure 1:
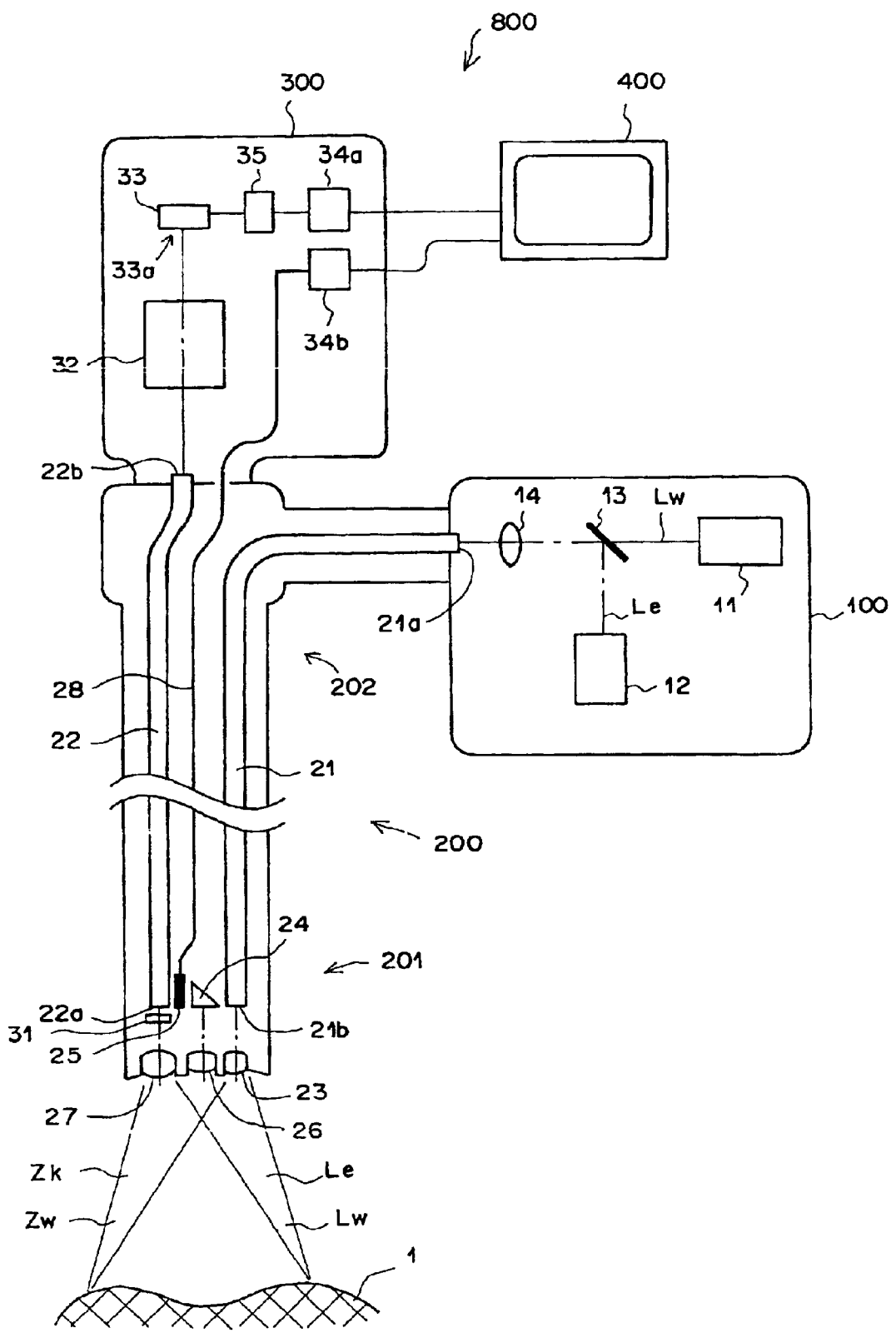
FIG. 1 is a schematic drawing of a fluorescent endoscope according to the first embodiment of the present invention.

Hereinafter, with reference to the drawings, the preferred embodiments of the present invention will be explained. FIG. 1 is a schematic drawing of a first embodiment of a fluorescent endoscope implementing a photographing apparatus for executing the photographing method according to the present invention.

Endoscope apparatus 800 comprises a light source unit 100 for emitting stimulating light Le of a wavelength of 410 nm, an endoscope unit 200 for transferring a fluorescent image of a living-tissue subject 1, which is formed of the fluorescent light emitted by upon illumination thereof by stimulating light Le emitted by light source unit 100 and passed through an illumination fiber 21, from an input face 22a of an image fiber 22 to an output face 22b of said image fiber 22, a fluorescent image photographing unit 300 for photographing, converting to an image signal and outputting the fluorescent image transferred to output face 22b of image fiber 22, and a display 400 for displaying as an image the image signal that has been output from fluorescent image photographing unit 300 and input thereto.

Light source unit 100 is provided with a white light source 11 for emitting white light Lw, and a stimulating light source 12 for emitting stimulating light Le. Of the white light Lw emitted from white light source 11, that having a wavelength of 420 nm is reflected and that in the wavelength range over 420 nm passes through a dichroic mirror 13, and the light passing through dichroic mirror 13 is focused by a focusing lens 14 and enters the end face 21a of illumination fiber 21. The stimulating light Le is emitted from stimulating light source 12 at a different timing from that of the white light Lw, and is reflected by dichroic mirror 13 and enters input face 21a of illumination fiber 21 in the same way as said component of white light Lw.

Endoscope unit 200 comprises a forward end 201, into which the image of living-tissue subject 1, produced by illumination thereof by the white light Lw and stimulating light Le transferred through illumination fiber 21 enters, an operation section 202 to which light source unit 100 and fluorescent image photographing unit 300 are connected, and an image fiber 22 formed of 10,000 strands of optical fiber, wherein illumination fiber 21 extends from operating section 202 to forward end 201.

In addition, forward end 201 is provided with an illumination lens 23 for directing the white light Lw and the stimulating light Le emitted from output 21b of illumination fiber 21 entering end face 21a toward living-tissue subject 1, an assembly lens 26 for focusing the image of living-tissue subject 1 (hereinafter referred to as normal image Zw), formed via a prism 24 by the white light Lw reflected by said living-tissue subject 1, on a normal-image photographing element 25, and a fluorescent image assembly lens 27 for focusing the image of living-tissue subject 1 (hereinafter referred to as fluorescent image Zk), which is composed of the fluorescent light emitted by said living-tissue subject 1 upon illumination thereof by stimulating light Le and passed through a stimulating light cutoff filter that cuts off wavelengths of light in the wavelength range below 420 nm, on input face 22a of image fiber 22; fluorescent image Zk focused on said input face 22a of image fiber 22 is transferred to output face 22b thereof. On the other hand, normal image Zw focused on normal-image photographing element 25 is converted into an electric image signal and transferred via a cable 28 to fluorescent image photographing unit 300.

Output face 22b of image fiber 22 is connected to fluorescent image photographing unit 300, and fluorescent image Zk conveyed to output face 22b is passed through assembly lens 32 and reduced and assembled within light-receiving zone 33a of fluorescent image photographing element 33, which is a front-exposure type CCD photographing element comprising 25,000 pixels. The fluorescent image Zk focused on said light-receiving zone 33a is photographed by fluorescent image photographing element 33, converted to an electric image signal and output. The image signal output by fluorescent image photographing element 33 is input to an image signal extraction circuit 35, and only the image signal obtained from the pixels contained in the image readout zone contained in the assembly zone, which has been determined in advance, within light-receiving zone 33a is extracted and output and again converted to an image signal by a visible image processing circuit 34a and output. On the other hand, the image signal output by normal-image photographing element 25 and transferred via cable 28 is input to visible image processing circuit 34b, converted to an image signal and output.

The two images output from visible image processing circuits 34a and 34b are input to display 400 and displayed as visible images.

Next, the operation of the fluorescent endoscope of the configuration described above will be explained. Stimulating light Le emitted from light source 100 enters end face 21a of illumination fiber 21, is conveyed therethrough to the other end face 21b, is output therefrom and passed through illumination lens 23 and illuminates live-tissue subject 1. Fluorescent image Zk emitted by live-tissue subject 1 upon illumination by stimulating light Le passes through fluorescent image assembly lens 27, stimulating light cutoff filter 31 and image fiber 22 and is conveyed to said output face 22b. Fluorescent image Zk conveyed to output face 22b is assembled within light-receiving zone 33a of photographing element 33 by assembly lens 32. Then, the assembled fluorescent image Zk is photographed by fluorescent image photographing element 33 and output as an image signal; only the image signal obtained from the signal charge held on the pixels contained within the image readout zone of light-receiving zone 33 is extracted by image signal extraction circuit 35 and output. The extracted image signal is converted to a visible-image signal by visible image processing circuit 34a and output from fluorescent image photographing unit 300.

On the other hand, the image of live-tissue subject 1 formed by the white light reflected from live-tissue subject 1 upon illumination thereof by white light Lw emitted from light source 100 is focused on normal-image photographing element 25 via prism 24. The assembled normal image Zw is photographed by normal-image photographing element 25, output as an image signal, input to visible image processing circuit 34b via cable 28, converted to a visible-image signal and output from fluorescent image photographing unit 300.

Next, a detailed explanation will be given for cases in which a fluorescent image Zk is photographed by fluorescent image photographing unit 300. As shown in FIG. 2, fluorescent image Zk transferred to output face 22b is assembled within light-receiving zone 33 as close as possible to readout port 33b from which an image signal is read out from fluorescent image recording element 33. More specifically, a fluorescent image Zk having a circular outline is focused on a zone inscribed in a corner formed by adjacent sides L1 and L2, which define readout port 33b of light-receiving zone 33a of fluorescent photographing element 33. The number of pixels Nd (the number of pixels within the light-receiving zone 33a receiving the light of the fluorescent image focused on light-receiving zone 33a) contained within the fluorescent image focusing zone Es in which fluorescent image Zk has been assembled is less than four times the number of pixels Nf (the number of strands of optical fiber representing fluorescent image Zk) representing the image formed on the output face 22b of image fiber 22, that is to say, the relationship therebetween is set so as to satisfy the condition expressed by the formula Nf×4>Nd.

That is to say, in conventional photographing systems, the fluorescent image Zk conveyed to output face 22b of image fiber 22 is focused on a light-receiving zone having a number of pixels greater than the sampling number of Nf×4 required to obtain the image data of the pixels formed of the number of optical fiber strands Nf; for example, the fluorescent image Zk is focused on a fluorescent image focusing zone Eb 4 times the size of fluorescent image focusing zone Es (16 times the number of pixels, and also substantially 16 times the area), which encompasses almost the entire area of light-receiving zone 33a (refer to FIG. 3).

Therefore, for a case in which fluorescent image Zk, which has been subjected to readout peak cell binning processing, where 4×4 pixels=16 corresponds to 1 pixel, is focused on fluorescent image focusing zone Eb and photographed, because each 16 pixels forming the fluorescent image are treated as corresponding to 1 pixel, the image becomes an image corresponding to the same as that of aforementioned pixels Nd, and the total quantity of received light also becomes equivalent to aforementioned quantity of fluorescent light obtained when said fluorescent image Zk is assembled small on few pixels in fluorescent image focusing zone Es and the quantity of fluorescent light obtained when said fluorescent image Zk is assembled large on many pixels in fluorescent image focusing zone Eb.

Accordingly, for cases in which fluorescent image Zk is not subjected to peak cell binning processing and is assembled small in fluorescent image focusing zone Es, and cases in which fluorescent image Zk is assembled large in fluorescent image focusing zone Eb, is subjected to peak cell binning processing, where 4×4 pixels corresponds to 1 pixel and photographed, with regard to the total amount of received light and resolution, the conditions are the same. However, if the quantity of noise contained in the image signal of the photographed images are compared, the fluorescent image Zk focused on fluorescent image focusing zone Es having few pixels and photographed has less noise per pixel (that which corresponds to 1 pixel) than does the fluorescent image focused on fluorescent image focusing zone Eb having many pixels.

Figure 4A:
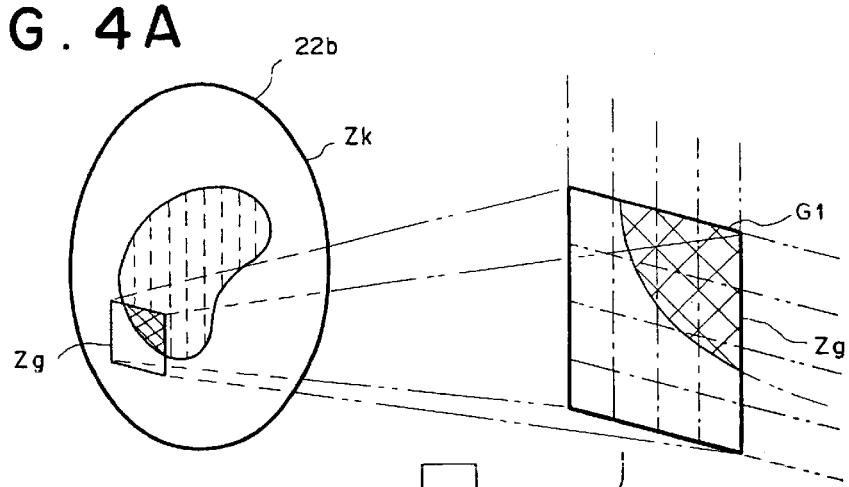
FIGS. 4A, 4B and 4C show the relationship between photographing system and the quantity of readout noise and dark noise produced thereby.

That is to say, as shown in FIG. 4A, when a portion Zg within fluorescent image Zk conveyed to output face 22b of image fiber 22 is focused on a zone g1 formed of 4×4=16 light-receiving pixels, not subjected to peak cell binning processing and is photographed, the total quantity of dark noise and read out noise TDR 1 contained in image signal P1 obtained from the photographed 16 light-receiving pixels is 16 times the quantity of dark noise DN and read out noise Rn produced from 1 pixel, that is:

$TDR1=16\times DN+16\times RN.$

Figure 4B:
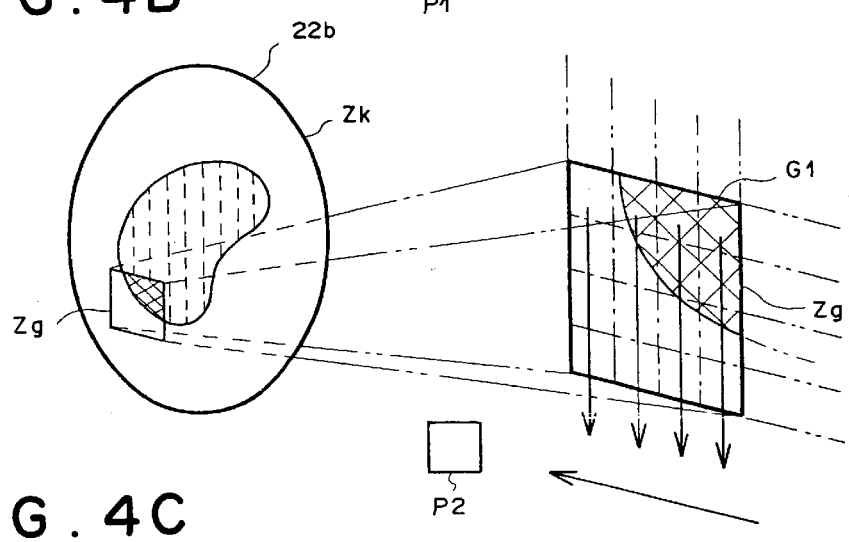

In addition, as shown in FIG. 4B, in the same way as described above, when a portion Zg within fluorescent image Zk is focused on a zone G1 formed of 4×4=16 light-receiving pixels, subjected to readout peak cell binning processing, where 4×4=16 pixels in zone G1 correspond to 1 pixel, and photographed, the total quantity of dark noise and read out noise TDR 2 contained in image signal P2 obtained from the photographed 16 light-receiving pixels is the sum of 16 times the quantity of dark noise DN produced from 1 pixel and 1 times the quantity of read out noise Rn produced from 1 pixel, that is:

$TDR1=16\times DN+1\times RN.$

Figure 4C:
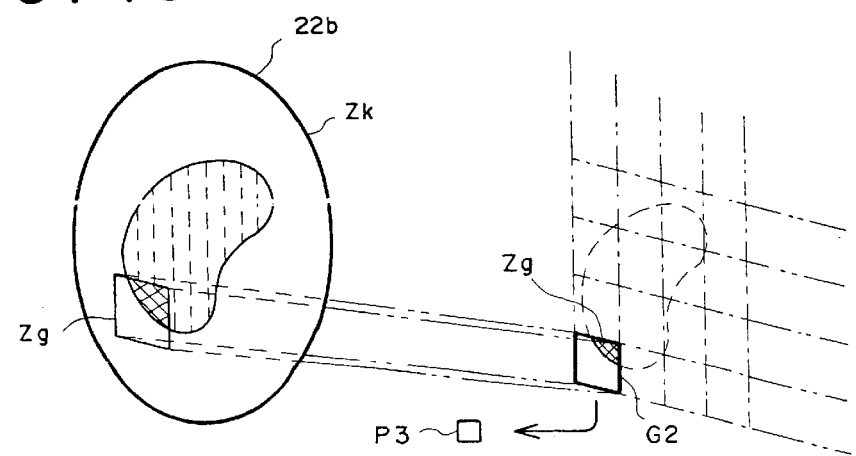
Figure 5A:
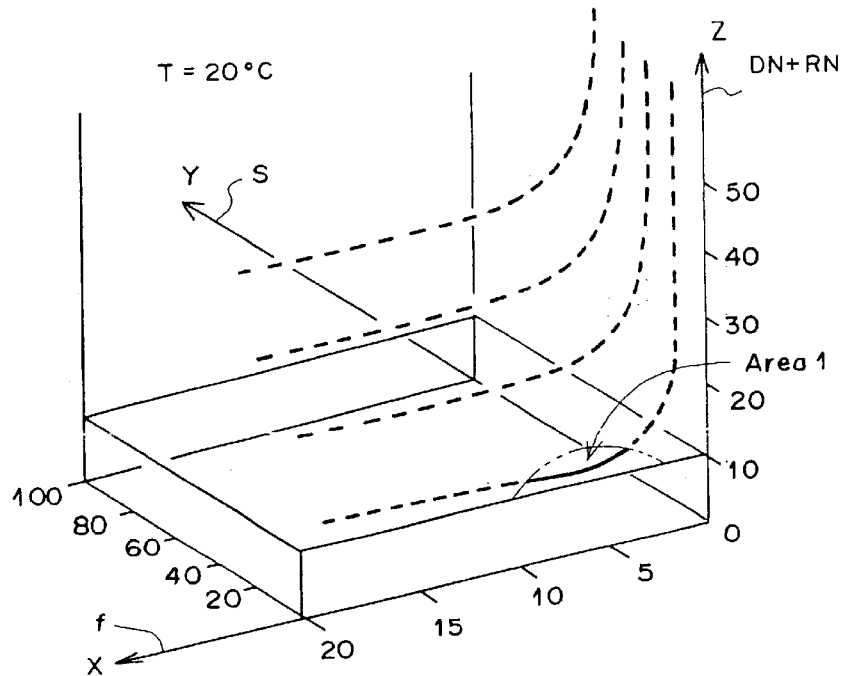
FIGS. 5A and 5B show the quantity of noise produced when the temperature is 20° C.
Figure 5B:
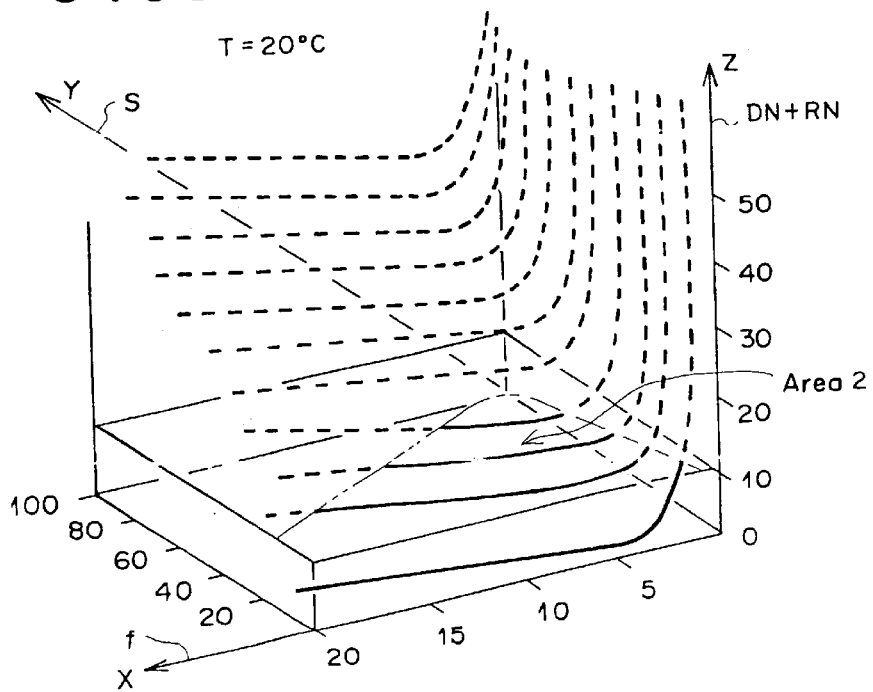

On the other hand, as shown in FIG. 4C, when a portion Zg of the same fluorescent image Zk described above is assembled small in a zone G2 formed of 1 light-receiving pixel, the total quantity of dark noise and read out noise TDR 3 contained in image signal P3 obtained from the photographed 1 pixel is the sum of 1 times the quantity of dark noise DN and read out noise Rn produced from 1 pixel, that is:

$$TDR1 = 1 \times DN + 1 \times RN;$$
$$= (1/16) \times TDR1;$$
$$= (1/8) \times TDR2.$$

Accordingly, if fluorescent image Zk is assembled small and photographed, compared to a case in which the same fluorescent image Zk is assembled large and photographed, the total quantity of noise contained in the image signal representing fluorescent image Zk on only the small number of pixels is reduced, the total quantity of received light can be made equal, and as a result, the quantity of light received per pixel can be increased.

More specifically, in a case, for example, in which fluorescent image Zk is focused on the entire area of a light-receiving zone of a photographing element comprising 512× 512 pixels (substantially 250,000 pixels), is subjected to peak cell binning processing, where 4×4=16 pixels corresponds to 128×128 pixels (corresponding to substantially 16,000 pixels), and photographed, compared to a case in which the same fluorescent image Zk is optically reduced to ¼ size 128×128 pixels (the 16,000 pixels of a zone ¹⁄₁₆ of the light-receiving zone of the photographing element) and assembled and photographed, the noise contained in the imager signal obtained of each fluorescent image is as follows.

That is, as shown in FIGS. 5A, 5B and 6A, 6B, the X axis is the readout frequency of the photographing element: f (mega pixels/sec), the Y axis is the area of 1 pixel of the photographing element: S ($\mu m^2$) and the Z axis is the total of the read out noise added to the dark noise read out from the photographing element per pixel: DN+RN (number of electrons), and for cases in which the exposure time is ¹⁄₃₀ seconds at 20° C., the photographing element and the readout circuit must be set as per the zone setting shown in Area 1 of FIG. 5 in order to control the sum of readout noise electrons and dark noise electrons per pixel contained in an image signal read out when fluorescent image Zk is assembled large in a light-receiving zone comprising 512× 512 pixels, is subjected to peak cell binning processing and photographed to 10 or less; there is almost no freedom in setting the substantially fixed range of the readout frequency F and the area S of 1 pixel. On the other hand, to control the sum of readout noise electrons and dark noise electrons per pixel contained in an image signal read out when the same fluorescent image Zk is optically reduced to ¼ size, assembled small in a zone comprising 128×128 pixels and photographed, readout frequency F and area S of 1 pixel can be set as per the zone shown in Area 2 of FIG. 5B, wherein the range of possible settings for readout frequency F and area S of 1 pixel are expanded, and it becomes possible to select settings whereby the sum of the number of electrons of readout noise and dark noise per pixel (hereinafter referred to as number of noise electrons per pixel) can be controlled to even less than 10.

Figure 6A:
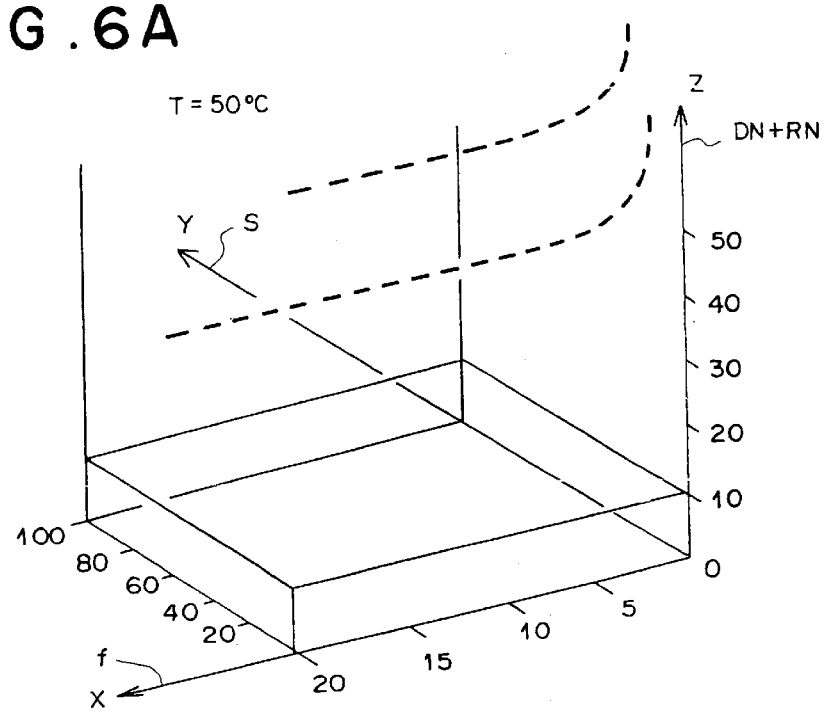
FIGS. 6A and 6B show the quantity of noise produced when the temperature is 50° C.
Figure 6B:
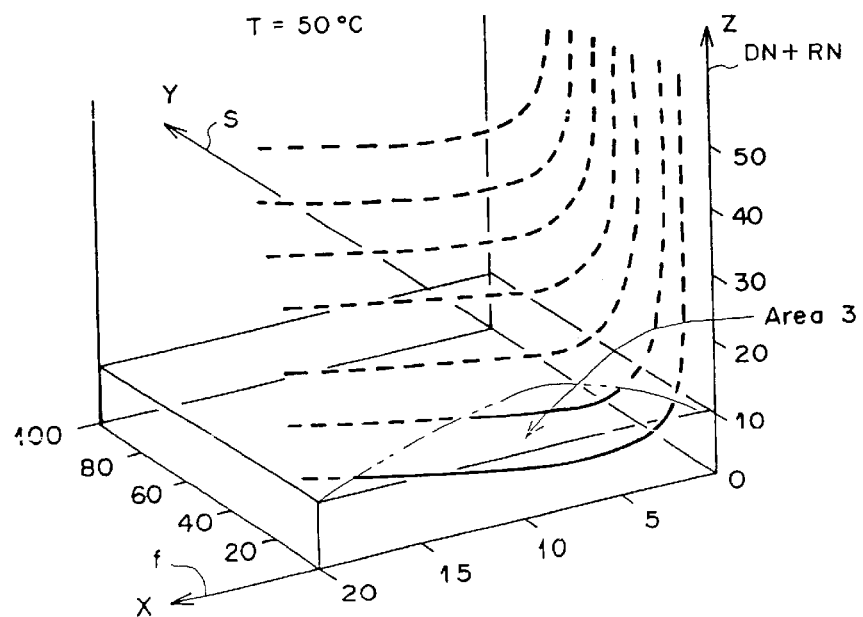

In addition, compared to the total quantity of noise electrons produced when the temperature of the photographing element is 50 C.°, as shown in FIG. 6A, there is no setting zone for readout frequency F and the area S of 1 pixel to control the number of noise electrons contained to 10 or less per pixel in an image signal readout when fluorescent image Zk is assembled large, subjected to peak cell binning processing and photographed, however, the setting zone to control the number of noise electrons per pixel contained in an image signal read out when the same fluorescent image Zk is optically reduced to ¼ size, assembled small in a zone comprising 128×128 pixels and photographed is the zone shown in Area 3 of FIG. 6B, and the settings for readout frequency F and area S of 1 pixel can be selected from this zone.

In this way, by focusing the fluorescent image within a light-receiving zone in which the relationship between the number of pixels Nf representing fluorescent image Zk formed on the output face of the image fiber, and the number of pixels Nd receiving the light of the fluorescent image assembled within the light-receiving zone is such that the condition expressed by the formula: Nd×4>Nf, is satisfied; the number of pixels falls within the range not meeting the required sampling number for obtaining the complete image data of the fluorescent image formed on the output face of the image fiber, and because the light of the fluorescent image has been received on a number of pixels in a range smaller than that by which it becomes possible to distinguish the change of state to a tissue accompanying various types of disease by analyzing a photographed fluorescent image, the total quantity of fluorescent light received is not reduced, the number of pixels, in the range within which analysis of the fluorescent image is unimpeded, receiving the light of fluorescent image Zk can be reduced, and as a result, because the amount of dark noise produced per pixel is not changed and the quantity of light received per pixel can be increased, the fluorescent image can be photographed as an image having a high S/N ratio.

In addition, for cases in which the noise produced on 1 pixel of fluorescent image photographing element 33 is set so as to be controlled to 10 or less, for example, as described above, in the standard photographing state, that is, in a photographing state in which the living-tissue subject is illuminated by 100 mw of stimulating light having an illumination coverage angle of 120° and in which the fluorescent image is photographed utilizing the entire light-receiving zone of the photographing element and an exposure time of 1/30 seconds, an image of a cancerous tissue can be obtained as an image having a S/N ratio of 1 or higher, and if, as described above, the fluorescent image is reduced to ¼ size and focused on one section of the light-receiving zone of the photographing element, an image signal having an even higher S/N ratio can be obtained.

Further, if the number of optical fiber strands of the output face of an image fiber is large, such that the number of pixels representing a fluorescent image is, for example, 30,000, the formula expressing the condition to be met by the relation between the number of pixels Nf and the number of pixels Nd becomes: Nf×4=120,000>Nd, and for cases in which the number of pixels Nd receiving the light of the fluorescent image within the light-receiving zone is sufficiently large, for example Nd=100,000, there are not an unnecessarily large number of pixels Nd of the light-receiving zone of the photographing element focusing the fluorescent image formed on the output face of the image fiber, and by focusing the fluorescent image in a light-receiving zone limited to having 40,000 or fewer pixels, which is the number at which it is possible to analyze a photographed fluorescent image and distinguish the change of state to a tissue accompanying various types of disease, the quantity of fluorescent light received per pixel can be further increased and the fluorescent image read out from the photographing element, and the fluorescent image can be obtained as an image signal having even higher S/N ratio.

Still further, by photographing and reading out fluorescent image Zk at the closest point to readout port 33b, fluorescent image Zk can be photographed as an image having an even higher S/N ratio.

That is to say, as shown in FIG. 7A, if the pixels arranged in lines in light-receiving zone 33a are labeled starting with the line closest to readout port 33b as #1, #2, #3, etc., when read out from the photographing element as an image signal, as shown in FIG. 7B, the image signal stored on a one line portion is read out from readout port 33b starting with the pixels of line #1, and when read out of the image charge stored on the pixels in line #1 is complete, as shown in FIG. 7C, the image signal stored on the pixels of line #2 is transferred one line to the position of readout port 33b, that is, is transferred to the position that had been occupied by the already read out line #1. Then, as shown in FIG. 7D, in the same way as the one line portion of the pixels of line #1 were read out, the image signal stored on line #2 is read out from readout port 33b in a one-line portion. Then, this type of operation is repeated and by reading out the image charge stored on each pixel, because fluorescent image focusing zone Es in which fluorescent image Zk is assembled is read out faster than the other zones, the quantity of dark noise accumulated on each pixel with the passage of time can be kept small.

In other words, the image focusing zone (fluorescent image focusing zone Es) for focusing round fluorescent image Zk is set so that it is inscribed in a corner formed by adjacent sides L1 and L2, which define readout port 33b of light-receiving zone 33a of fluorescent photographing element 33, and although each line #1, #2, #3, etc. also contains pixels of zones outside fluorescent image readout zone Es, cases in which a fluorescent image Zk of the same size is assembled at the closest position to the set readout port 33b described above, readout of fluorescent image Zk can be completed more rapidly than for cases in which fluorescent image Zk is focused on other regions, such as region Ex shown in FIG. 7D.

For cases in which the signal charge stored on each pixel of the photographing element is sequentially read out as described above, by focusing the fluorescent image at the closest position to the readout port within the light-receiving zone of the photographing element, because the time for dark noise to accumulate is reduced, the fluorescent image can be photographed as an image having a higher S/N ratio.

The image signal carrying the image data of a fluorescent image Zk photographed in this way is input to image signal extraction circuit 35, and only the image signal corresponding to the pixels contained within image readout zone R of light-receiving zone 33a of the fluorescent image photographing element shown in FIG. 2, and the thus extracted image signal is again input to image signal processing circuit 34a, converted to a visible-image signal and output from fluorescent image photographing unit 300. Then, the image signal carrying the image data of said fluorescent image Zk is input to display 400 together with the image signal carrying the image data of normal image Zw, which was photographed by normal-image photographing element 25 and output via visible image processing circuit 34b, combined therewith and output on a single screen as a visible image at the same time.

Figure 8:
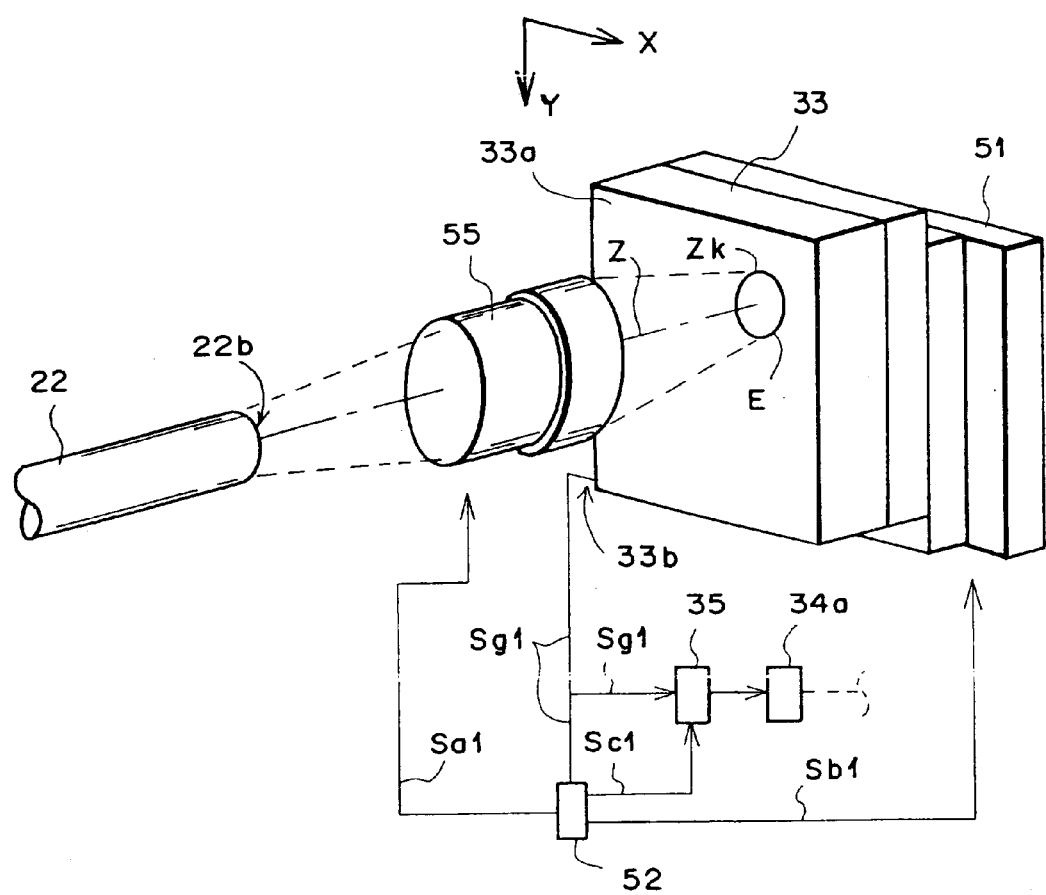
FIG. 8 is a schematic drawing of a fluorescent endoscope according to the second embodiment of the present invention.

FIG. 8 is a schematic drawing of the main part of a fluorescent endoscope implementing photographing apparatus for executing the photographing method according to the second embodiment of the present invention, and the structures having functions in common with those in the first embodiment are labeled with the same reference numerals. As shown in FIG. 8, the fluorescent endoscope according top the second embodiment of the present invention comprises a zooming optical means 55 capable of changing the zooming rate of a fluorescent image Zk transferred to output face 22b of the image fiber and assembled at a predetermined zooming rate on fluorescent image photographing element, an XY table 51 for supporting fluorescent image photographing element 33, moving fluorescent image photographing element 33 and the light-receiving face thereof on a parallel XY plane surface and which is provided with a drive portion (not shown) for changing the position at which fluorescent image Zk is assembled within light-receiving zone 33a, and a photographing-conditions setting device 52 for splitting the signal again output from readout port 33b of fluorescent-image photographing element 33, inputting said split signal and obtaining the total quantity of fluorescent light the fluorescent image photographing element received, and outputting 4 setting signals, corresponding to said obtained quantity of received fluorescent light, related to the zooming rate of zooming optical system 55, the fluorescent image receiving sector within light-receiving zone 33a of the fluorescent-image photographing element, the readout zone within light-receiving zone 33a of the fluorescent-image photographing element, and the readout frequency of the photographing element to the zooming optical system 55, XY table 51 and image signal extracting circuit 35, and the fluorescent image photographing element 33, respectively, wherein the other structures are the same as those of the first embodiment.

Note that photographing conditions setting device 52 is also provided with a function for changing, corresponding to the zooming rate of zooming optical system 55, the readout frequency of fluorescent image photographing element 33, and corresponding to the degree to which the zooming rate of zooming optical system 55 becomes lower, the readout frequency of fluorescent image photographing element 33 is set lower. In addition, for cases in which said fluorescent image photographing element is a charge-amplification type photographing element that amplifies the charge by impact ionization, the readout frequency of the fluorescent image photographing element is fixed, and is not changed by the zooming rate of zooming optical system 55.

That is to say, according to photographing elements that are not charge-amplification type photographing elements that amplify the charge by impact ionization, for cases in which the readout speed is 30 frames/second, a greater quantity of readout noise than dark noise is produced, and said readout noise accounts for the greater part of the noise produced. Here, if the readout speed is set and the number of pixels read out per frame is ¼, it is possible to make the readout frequency ¼ (it is possible to increase the time to readout 1 pixel by 4 times). Because the quantity of readout noise becomes larger in proportion to the readout frequency, if the readout frequency becomes ¼, the readout noise becomes ½. In other words, if the zooming rate is set at ½ and the predetermined observation zone is focused smaller on the photographing element and the number of pixels to be read out is made to be ¼, the readout frequency can be made to be ¼, and as a result, the readout noise can be reduced by ¼. Accordingly, the quantity of noise produced is reduced, and the sensitivity is improved (the S/N ratio of the image signal obtained is improved).

On the other hand, for cases in which a charge-amplification type photographing element that amplifies the charge by impact ionization is used at a readout speed of 30 frames/second, the dark noise accounts for the greater part of the noise produced (compared to a normal photographing element, the readout noise becomes less than ¹⁄₁₀). The reverse side of this is that this dark noise cannot be reduced by the effect of impact ionization. Therefore, by making the zooming rate of zooming optical system 55 ½ and focusing the predetermined observation zone smaller on the photographing element and making the number of pixels to be readout ¼, even if the readout frequency is made ¼, the dark noise is not reduced. For cases such as this, quite the opposite, if the readout frequency is fixed and not changed in correspondence to the zooming rate, the number of pixels read out when the zooming rate has been set low becomes small, the time required to read out 1 frame is shortened, and the effect whereby the dark noise is reduced can be used.

Note that for cases in which the zooming rate of zooming optical system 55 has been made low, the predetermined image is focused in a smaller zone on the photographing element (on a small number of pixels), and this small number of pixels is controlled by photographing conditions setting device 52 so as to be obtained as a 1 frame image.

Next, operation of the second embodiment will be explained. As shown in FIG. 8, in the initial state, in which zooming optical system 55 has been set to the desired zooming rate and XY table 51 has been set to the desired position, the fluorescent image Zk transferred to output face 22b of the image fiber is assembled within light-receiving zone 33a of the fluorescent-image photographing element at the desired size as an image having a circular outline in fluorescent image focusing zone E, photographed and output from readout port 33b as image signal Sg1. Then, the image signal Sg1 output from readout port 33b is split in two: the image signal Sg1 transferred to one side of the transfer circuit is input to the image signal extraction circuit 35, and the image signal Sg1 transferred to the other side of the transfer circuit is input to photographing-conditions setting device 52. Note that because the image signals of the split image signal have the same signal value as the image signal prior to splitting, all 3 of said image signals are represented as Sg1.

Next, setting the settings of zooming optical system 55, XY table 51 and image signal extraction circuit 35, based on the setting signals output from photographing-conditions setting device 52 into which image signal Sg1 has been input, will be explained. Photographing-conditions setting device 52 into which image signal Sg1 has been input obtains the total quantity of fluorescent light Tp1 received by fluorescent image photographing element 33, that is, obtains the total quantity of fluorescent light received from fluorescent image Zk, and by dividing the total quantity of received light Tp1 by the value, Op, of the standard quantity of light received per pixel, which has been entered and recorded in photographing-conditions setting device 52 in advance, photographing-conditions setting device 52, obtains a number of pixels, Tp1/Op=Gn1, appropriate for receiving the light of said fluorescent image Zk. In other words, if fluorescent image Zk is focused on a number of pixels Gn1 (individual pixels) within light-receiving zone 33a of the fluorescent image photographing element, the average quantity of light received per pixel in the light-receiving zone receiving the light of fluorescent image Zk can be made to match the standard value Op of the quantity of light to be received per pixel recorded in photographing-conditions setting device 52.

Note that said standard of quantity of received Op is set at the minimum quantity of light required to be received per pixel so as to ensure for the clarity of the fluorescent image to be viewed, and accompanying reception of a quantity of light per pixel that is lower than this value, the signal charge stored due to reception of the fluorescent light becomes buried in the signal charge stored due to noise, and the fluorescent image to be viewed has poor clarity, whereby it is difficult to distinguish clearly the structures therein.

For cases in which the relation of the number of pixels Gn1 to aforementioned value Nfx4 is such that Nfx4>Gn1, the number of pixels receiving the light of fluorescent image Zk is Gn1, and for cases in which the relation is such that Nfx4<Gn1, the number of pixels receiving the light of fluorescent image Zk is the number of pixels Gn1' satisfying the condition: Nfx4>Gn1'. That is to say, even for cases in which the quantity of light emitted from a living-tissue subject is extraordinarily large, the fluorescent image Zk is not focused on a number of pixels greater than that required; the number of pixels receiving the light is set so that the quantity of light received per pixel is increased. Based on the number of pixels receiving the light of fluorescent image Zk, set as described above, the area of the light-receiving zone in which fluorescent image Zk is assembled, fluorescent image assembly area P1, is obtained.

Figure 9:
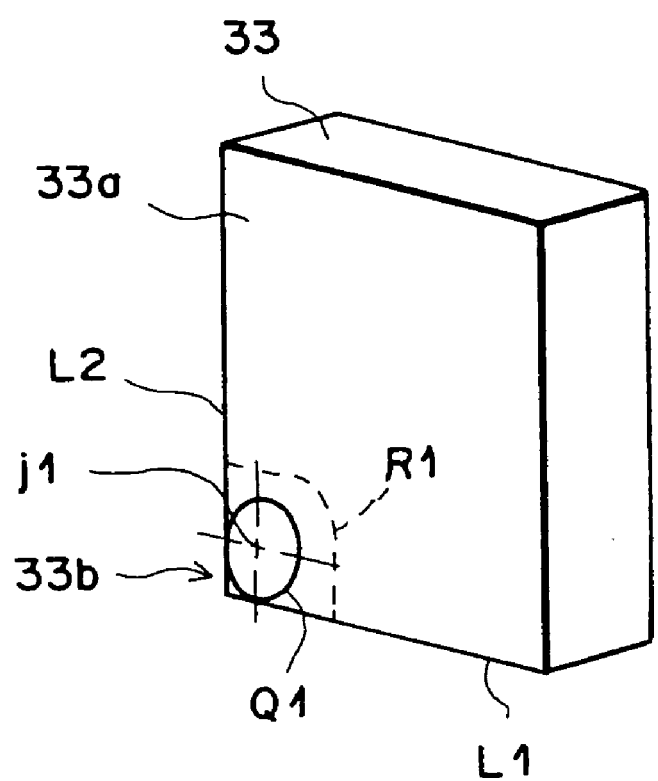
FIG. 9 shows a fluorescent image light-receiving sector set within the light-receiving zone.

Next, the obtaining of the setting signals by photographing conditions setting device 52, based on aforementioned fluorescent image assembly area P1, will be explained. First, by obtaining the ratio of output face 22b of the image fiber to aforementioned fluorescent image assembly area P1, a setting signal Sa1, which sets the predetermined zooming rate M of zooming optical system 55 is obtained so that the area of the fluorescent image Zk to be assembled within light-receiving zone 33a of the fluorescent image photographing element is equivalent to fluorescent image assembly area P1. Next, in the same way as in the first embodiment and as shown in FIG. 9, within a circular zone inscribed by sides L1 and L2 and enclosing readout port 33b within light-receiving zone 33a of the fluorescent image photographing element, fluorescent image light-receiving sector Q1 within area P1 is set, and based on the position of center-point J1 within said fluorescent image light-receiving sector Q1, a setting signal Sb1, which determines the orientations of the X and Y directions of fluorescent image photographing element 33, is determined. Then, by setting as an image readout zone R1 a desired zone contained within fluorescent image light-receiving sector Q1 within light-receiving zone 33*a* of the fluorescent image photographing element, a setting signal Sc1 for extracting a specific image signal corresponding to the pixels contained in image readout zone R1 is obtained.

Figure 10:
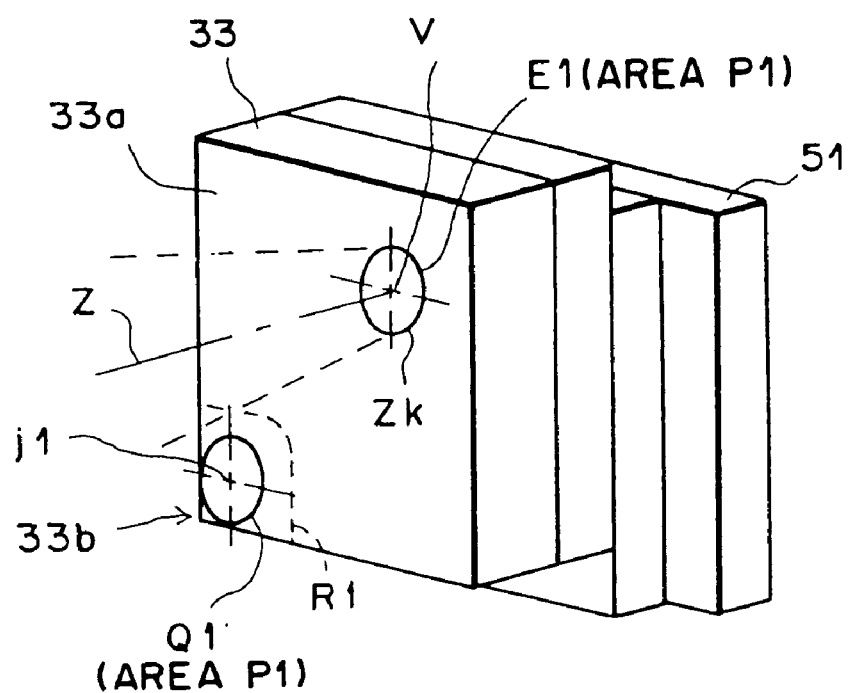
FIG. 10 shows a fluorescent image focusing zone in which fluorescent image Zk is to be assembled.

Continuing, photographing conditions setting device 52 outputs setting signals Sa1, Sb1 and Sc1 to zooming optical system 55, XY table 51 and image signal extraction circuit 35, respectively. When setting signal Sa1 is input to zooming optical system 55, the zooming rate thereof is set, and as shown in FIG. 10, fluorescent image Zk having a fluorescent image assembly area P1 is assembled within fluorescent image focusing zone E1 within light-receiving zone 33*a* of the fluorescent image photographing element.

Then, as shown in FIG. 11, when setting signal Sb1 is input to XY table 51, fluorescent image photographing element 33 is moved by XY table 51 in the direction of arrow H so as to match center-point J1 of fluorescent image light-receiving sector Q1 within said light-receiving zone 33*a* with the position at which light axis Z of the zooming optical system focusing fluorescent image Zk intersects with light-receiving zone 33*a* of the fluorescent image photographing element, that is, center-point V of the fluorescent image focusing zone E1. That is to say, center-point J1 of fluorescent image light-receiving sector Q1 within light-receiving zone 33*a* of fluorescent image photographing element 33 is moved together with fluorescent image photographing unit 33 toward center-point V of fluorescent image focusing zone E1, in which the fluorescent image Zk has been assembled; the relative positions of the assembly zone, in which fluorescent image Zk has been assembled, and fluorescent image photographing element 33 are changed and XY table 51 stops at the position at which aforementioned fluorescent image focusing zone E1 and fluorescent image light-receiving sector Q1 are matched.

Then, fluorescent image Zk is photographed under the settings described above, image signal Sg1 that has been read out from readout port 33*b* of fluorescent image photographing element 33 and input to image signal extraction circuit 35, only the image signal obtained from the pixels contained within the range of readout zone R1 that has been set within light-receiving zone 33*a* is extracted and output, and the extracted and output image signal is input to visible-image signal processing circuit 34*a*, converted to a visible-image signal and output.

The visible-image signal, carrying the image data of fluorescent image Zk, output from visible image data processing circuit 34*a*, in the same way as in the first embodiment, is photographed by normal-image photographing element 25 and output via visible-image signal processing circuit 34*b*, and input, combined with the image signal carrying the image data of normal image Zw, to display 400 and output simultaneously on one display screen as a visible image (refer to FIG. 1).

Next, an explanation will be given for a case in which, with the fluorescent image Zk is in the state of being displayed as described above, the quantity of fluorescent light emitted from a living-tissue subject and the quantity of light received at fluorescent image photographing element 33 is reduced. As shown in FIG. 12, in the same way as described above, the photographing conditions setting device 52 into which the image signal Sg2 obtained when the quantity of fluorescent light received at the fluorescent image photographing element 33 is reduced obtains the total quantity of received light Tp2 received at fluorescent image photographing element 33, and by dividing said total quantity of received light Tp2 by aforementioned standard quantity of received light Op, a smaller number of pixels than that described above, Gn2=Tp2/Op, is obtained. In other words, if fluorescent image Zk is focused on the number of pixels Gn2 (individual pixels) within light-receiving zone 33*a* of fluorescent image photographing element 33, the average quantity of light received per pixel within this assembly zone can be made to be the same as the standard quantity of received light Op.

Then, in the same way as described above, for cases in which the relation of the number of pixels Gn2 to aforementioned value Nfx4 is such that Nfx4>Gn2, the number of pixels receiving the light of fluorescent image Zk is Gn2, and for cases in which the relation is such that Nfx4<Gn2, the number of pixels receiving the light of fluorescent image Zk is the number of pixels Gn2' satisfying the condition: Nfx4>Gn2'. Based on the number of pixels receiving the light of fluorescent image Zk, set as described above, the area of the light-receiving zone in which fluorescent image Zk is assembled, fluorescent image assembly area P2, is obtained.

Continuing, by the same procedure described above, setting signals Sa2, Sb2 and Sa3 are obtained by photographing conditions setting device 52, based on aforementioned fluorescent image focusing zone P2, and output to zooming optical means 55, XY table 51 and image signal extraction circuit 35, respectively. When setting signal Sa2 is input to zooming optical system 55, the zooming rate of zooming optical system 55 is set so that when fluorescent image Zk is assembled, the area within light-receiving zone 33*a* of the fluorescent image photographing element focusing said fluorescent image Zk becomes fluorescent image assembly area P2. Next, when setting signal Sb2 is input to XY table 51, fluorescent image light-receiving sector Q2 is set at the closest position to the readout port 33*b* of the fluorescent image photographing element within light-receiving zone 33*a* having the same area as aforementioned fluorescent image assembly area P2, and fluorescent image photographing element 33 is moved by XY table 51 so as to match center-point J2 of said fluorescent image light-receiving sector Q2 within said light-receiving zone 33*a* with the light axis Z of the optical system focusing fluorescent image Zk, that is, center-point V of the fluorescent image focusing zone E2. That is to say, fluorescent image focusing zone E2 is moved together with fluorescent image photographing element 33 toward fluorescent image light-receiving sector Q2 in which fluorescent image Zk is has been assembled, and XY table 51 stops at the position at which aforementioned fluorescent image focusing zone E2 and fluorescent image light-receiving sector Q2 are matched.

Then, according to the setting in which the resolution of aforementioned fluorescent image is lowered, the quantity of light received per pixel is increased and the S/N ratio improved, fluorescent image Zk is photographed and readout from readout port 33*b* as image signal Sg2, said image signal Sg2 is input to image signal extracting circuit 35 and only the image signal of the pixels contained within fluorescent image extraction zone R2 within fluorescent image light-receiving sector Q2, which has been set within light-receiving zone 33*a* based on aforementioned setting signal Sc2, is extracted and output, and said extracted and output image signal is converted to a visible-image signal and output.

The visible-image signal, carrying the image data of fluorescent image Zk, output from visible-image signal processing circuit 34a, in the same way as described above, is photographed by normal-image photographing element 25 and output via visible-image signal processing circuit 34b, and input, combined with the image signal carrying the image data of normal image Zw, to display 400 and output simultaneously on one display screen as a visible image.

In this way, according to the second embodiment of the present invention, by changing the size of the fluorescent image assembled within light-receiving zone 33a of the fluorescent image photographing element in accordance with the quantity of fluorescent light received at the photographing element, because adjustment can be made so that the quantity of light received per pixel is ensured and resolution of the fluorescent image is improved, the fluorescent image can be photographed as an image having an appropriate quantity of light as well as good resolution.

Note that according to the first and second embodiments, although fluorescent image Zk is assembled at the closest point to the readout port, even if fluorescent image Zk is not assembled at the closest point to the readout port, if the light received per pixel can be ensured to match the standard quantity of received light per pixel, the effect whereby the S/N ratio per pixel is improved can be obtained. Further, if the settings to assemble fluorescent image Zk at the closest point to the readout port are carried out, early readout of the signal charge, representing fluorescent image Zk, stored on each pixel of the fluorescent image focusing zone becomes possible, and because the time for dark noise to accumulate on each pixel contained in said fluorescent image focusing zone is shortened, the fluorescent image can be photographed as an image having a higher S/N ratio.

In addition, according to the first and second embodiments, an example utilizing a front-exposure type CCD photographing element was given, if a photographing element sequentially reads out the signal charge stored on each pixel, the photographing element to be utilized is not necessarily limited to front-exposure CCD type photographing elements; other photographing elements, such as rear-exposure type CCD photographing elements, etc. may also be used.

Note that for cases in which a rear-exposure type photographing element is used, because the quantum efficiency of a rear-exposure type photographing element is substantially twice that of a front-exposure type photographing element, in aforementioned standard photographing state, for cases in which a cancerous tissue is photographed as an image having an S/N ratio of 1 or higher, at normal temperature or lower, the photographing conditions can be set so that the sum of the number of electrons of readout noise and dark noise produced on each pixel within the light-receiving zone receiving the light of the fluorescent image is 20 or less and the fluorescent image formed on the output face of the image fiber photographed, and if the number of pixels receiving the light of fluorescent image Zk within the light-receiving zone is made few, the S/N ratio can be raised even further.

FIG. 13 is a schematic drawing showing the main part of a fluorescent image photographing unit, contained within a fluorescent endoscope apparatus implementing a photographing apparatus for carrying out the photographing method according to the third embodiment of the present invention, and structures having functions in common with those of the first embodiment are labeled with the same reference numerals. As shown in FIG. 13, the configuration of the fluorescent endoscope apparatus according to the third embodiment utilizes an MOS type photographing element 61 capable of reading out the signal charge stored on each pixel as the photographing element, which is set so that the fluorescent image Zk conveyed to output face 22b of the image fiber is assembled by an focusing mirror 32 in the fluorescent image focusing zone Es within the readout zone Fs set within light-receiving zone 61a of MOS type photographing element 61 and photographed, and in which the image signal extracting circuit 35 employed in the first embodiment has been excluded.

In addition, in the same way as in the first embodiment, the number of pixels Nd contained within fluorescent image focusing zone Es in which fluorescent image Zk has been assembled (the number of pixels Nd contained within light-receiving zone 61a receiving the light of fluorescent image Zk which has been assembled therein) is less than 4 times the number of pixels Nf displaying the fluorescent image formed on output face 22b of the image fiber, that is to say, is set so as to satisfy the condition: Nd×4>Nf.

According to this type of configuration, for cases in which the fluorescent image Zk conveyed to output face 22b of the image fiber is assembled by an focusing mirror 32 in the fluorescent image focusing zone Es within light-receiving zone 61a and photographed by MOS type photographing element 61, compared to cases in which fluorescent image Zk is focused on fluorescent image focusing zone Eb, which encompasses almost the entire light-receiving zone of the photographing element (refer to FIG. 14), cases in which fluorescent image Zk is assembled within light-receiving zone 61a on a small fluorescent image focusing zone Es satisfying the condition expressed by the formula: Nf×4>Nd, and photographed, the S/N ratio of the image can be improved due to the same reason as in the first embodiment.

For example, comparing fluorescent image Zk assembled large in fluorescent image focusing zone Zk of photographing element 61 to fluorescent image Zk assembled small within fluorescent image focusing zone Eb at $\frac{1}{16}$ the size of said fluorescent image focusing zone Es, the quantity of light received per pixel for cases in which fluorescent image Zk is assembled small on the $\frac{1}{16}$ size zone becomes 16 times that of cases in which fluorescent image Zk is assembled large on the entire light-receiving zone, and on the other hand, the quantity of noise produced per pixel is substantially equal. As a result, because the ratio of the signal charge stored on 1 pixel due to reception of fluorescent light to the signal charge stored as noise becomes high, the fluorescent image can be photographed as an image having a high S/N ratio.

Figure 15:
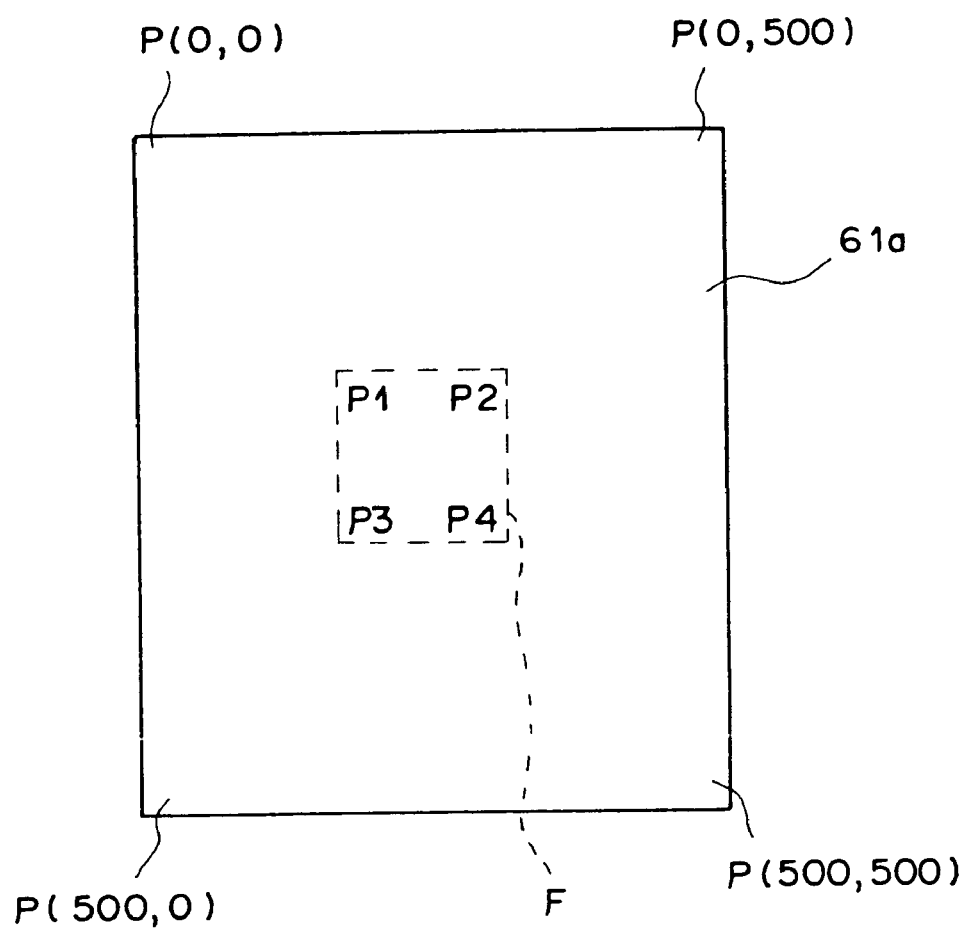
FIG. 15 shows the readout of an image signal from an MOS-type photographing element.

In addition, because the MOS type photographing element is capable of reading out, in a random manner, the signal charge stored on each pixel, there is no limitation due to the direction in which each pixel of the photographing element is arranged, and as shown in FIG. 15, for example, if the arrangement of the pixels of light-receiving zone 61a within MOS type photographing element 61 is 500×500 lines represented by P (500, 500), because the pixels contained within readout zone Fs enclosed within the 4 points of pixel P1=P (200, 200), pixel P2=P (200, 300), P3=(300, 200) and P4=(300, 300) can be set so as to be read out prior to the pixels contained within other zones, if said readout zone Fs is set so as to be read out prior to the other zones, the time for dark noise to accumulate on each pixel of readout zone Fs is shortened and the fluorescent image can be photographed as an image having a higher S/N ratio.

According to this type of setting, fluorescent image Zk is photographed by MOS type photographing element 61 and output therefrom as image signal Sg1, said image signal Sg1 is input to visible image processing circuit 34a, converted to a visible-image signal and output from fluorescent image photographing unit 300.

The visible-image signal, carrying the image data of fluorescent image Zk, output from visible-image signal processing circuit 34a, in the same way as in the first embodiment, is photographed by normal-image photographing element 25 and output via visible-image signal processing circuit 34b, and input, combined with the image signal carrying the image data of normal image Zw, to display 400 and output simultaneously on one display screen as a visible image.

FIG. 16 is a schematic drawing showing the main part of a fluorescent image photographing unit, contained within a fluorescent endoscope apparatus implementing a photographing apparatus for carrying out the photographing method according to the fourth embodiment of the present invention, and structures having functions in common with those of the third embodiment are labeled with the same reference numerals. Note that the third embodiment has been described in reference to the first embodiment, and a part of the explanation given below is given in reference to FIG. 1.

As shown in FIG. 16, the fluorescent endoscope apparatus according to the fourth embodiment comprises a zooming optical system 71 capable of changing the predetermined zooming rate at which the fluorescent image Zk conveyed to output face 22b of the image fiber is assembled within light-receiving zone 61a of MOS type photographing element 61, and a readout control device 73 for splitting and inputting the image signal output from MOS type photographing element 61, obtaining the total quantity of fluorescent light received at MOS type photographing element 61, obtaining the zooming rate setting value of zooming optical means 71 and the setting value of the readout zone within light-receiving zone 61a corresponding to said total quantity of received light, and outputting each respective setting signal to zooming optical system 71 and MOS type photographing element 61, wherein the other structures are the same as those of the third embodiment.

Next, the operation of photographing apparatus according to the fourth embodiment will be explained. In the initial state, in which the desired zooming rate of zooming optical system 71 and the desired readout zone within light-receiving zone 61a of MOS type photographing element 61 have been set, the fluorescent image Zk transferred to output face 22b of the image fiber is assembled at the desired position and the desired size within light-receiving zone 61a of MOS type photographing element 61 as an image having a round outline, photographed, and output as image signal Sg1. Then, the image signal Sg1 output from MOS type photographing element 61 is split in two: the image signal Sg1 transferred to one side of the transfer circuit is input to visible image processing circuit 34a, and the image signal Sg1 transferred to the other side of the transfer circuit is input to readout control device 73. Note that because the two image signals of the split image signal have the same signal value as the image signal prior to splitting, all three of said image signals are represented as Sg1.

Next, the setting of the zooming rate of zooming optical system 71, and the readout zone within light-receiving zone 61a, based on the setting signals output from readout control device 73 into which image signal Sg1 has been input, will be explained.

The readout control device 73, into which image signal Sg1 has been input, obtains the total quantity of fluorescent light received at MOS type photographing element 61, that is, the total quantity of received light Tp1 received through reception of fluorescent image Zk, and by dividing said total quantity of received light Tp1 by the value of the standard quantity of received light per pixel Op, which has been prerecorded in readout control device 73, an appropriate number of pixels to receive the light of fluorescent image Zk, Tp1/Op =Gn1, is obtained. In other words, if fluorescent image Zk is focused on a number of pixels Gn1 (individual pixels) within light-receiving zone 33a of the fluorescent image photographing element, the average quantity of light received per pixel within the light-receiving zone receiving the light of said fluorescent image Zk can be made to match that of the standard quantity of received light per pixel Op prerecorded in said readout control device 73.

Note that the value of aforementioned standard quantity of received light Op is set at the minimum quantity of light required to be received per pixel so as to ensure for the clarity of the fluorescent image to be viewed, and accompanying reception of a quantity of light per pixel that is lower than this value, the signal charge stored due to reception of the fluorescent light becomes buried in the signal charge stored due to noise, and the fluorescent image to be viewed has poor clarity, whereby it is difficult to distinguish clearly the structures therein.

For cases in which the relation of the number of pixels Gn1 to aforementioned value Nf×4 is such that Nf×4>Gn1, the number of pixels receiving the light of fluorescent image Zk is Gn1, and for cases in which the relation is such that Nf×4<Gn1, the number of pixels receiving the light of fluorescent image Zk is the number of pixels Gn1' satisfying the condition: Nf×4>Gn1'. That is to say, even for cases in which the quantity of light emitted from a living-tissue subject is extraordinarily large, the fluorescent image Zk is not focused on a number of pixels greater than that required; the number of pixels receiving the light is set so that the quantity of light received per pixel is increased. Based on the number of pixels receiving the light of fluorescent image Zk, set as described above, the area of the light-receiving zone in which fluorescent image Zk is assembled, fluorescent image assembly area P1, is obtained.

Continuing, the obtaining of the setting signals by readout control device 73, based on aforementioned fluorescent image assembly area P1, will be explained. First, by obtaining the ratio of output face 22b of the image fiber to aforementioned fluorescent image assembly area P1, the setting signal Sa1 for setting the predetermined zooming rate of zooming optical system 71, which causes the area within light-receiving zone 61a of MOS type photographing element 61 in which fluorescent image Zk is to be assembled to become equal to that of fluorescent image focusing zone P1, is obtained. Next, a setting signal Sb1 for setting a square-shaped readout zone F1, which circumscribes fluorescent image focusing zone E1 having a round shape, within which fluorescent image Zk is assembled in area P1 of light-receiving zone 61a, so that the center-point C1 thereof (the point at which the diagonal lines intersect) is matched with light axis Z of the optical system focusing the fluorescent image Zk, that is, with the center-point of fluorescent image fluorescent image focusing zone E1, is obtained.

Then, when setting Sa1 is input to zooming optical system 71, the zooming rate thereof is set, and fluorescent image Zk having fluorescent image assembly area P1 is assembled within light-receiving zone 61a of MOS type photographing element 61. Then, when setting signal Sb1 is input to MOS type photographing element 61, aforementioned readout zone F1 is set within the light-receiving zone 61a thereof.

According to the settings described above, fluorescent image Zk is photographed by MOS type photographing element 61 and output therefrom as image signal Sg1, said image signal Sg1 is input to visible image processing circuit 34a, converted to a visible-image signal and output from fluorescent image photographing unit 300.

The visible-image signal, carrying the image data of fluorescent image Zk, output from visible image data processing circuit 34a, in the same way as in the third embodiment, is photographed by normal-image photographing element 25 and output via visible-image signal processing circuit 34b, and input, combined with the image signal carrying the image data of normal image Zw, to display 400 and output simultaneously on one display screen as a visible image (refer to FIG. 1).

Next, an explanation will be with reference to FIG. 17 for cases in which, in the state described above in which the range of readout zone F1 containing fluorescent image Zk is displayed as a visible image, the quantity of light emitted from the living-tissue subject is reduced and the quantity of fluorescent light received on MOS type photographing element 61 is reduced.

Readout control device 73 into which image signal Sg2 has been input when the quantity of fluorescent light received by MOS type photographing element 61 is reduced, in the same way as described above, obtains the total quantity of fluorescent light received by MOS type photographing element 61, and by dividing the value of this total quantity of received light Tp2 by the value of aforementioned standard quantity of received light Op, a number of pixels Gn2 smaller than aforementioned number of pixels is obtained: Gn2=Tp2/Op. In other words, if fluorescent image Zk is focused on the number of pixels Gn2 (individual pixels) within light-receiving zone 61a of the fluorescent image photographing element, the average quantity of light received on the pixels within this assembly zone can be made to match the value of the standard quantity of received light Op.

Then, in the same way as described above, for cases in which the relation of the number of pixels Gn2 to aforementioned value Nfx4 is such that Nfx4>Gn2, the number of pixels receiving the light of fluorescent image Zk is Gn2, for cases in which the relation is such that Nfx4<Gn2, the number of pixels receiving the light of fluorescent image Zk is the number of pixels Gn2' satisfying the condition: Nfx4>Gn2'. Based on the number of pixels receiving the light of fluorescent image Zk, set as described above, the area of the light-receiving zone in which fluorescent image Zk is assembled, fluorescent image assembly area P2, is obtained.

Continuing, the obtaining of the setting signals by readout control device 73, based on aforementioned fluorescent image assembly area P2, will be explained. First, by obtaining the ratio of output face 22b of the image fiber to aforementioned fluorescent image assembly area P2, the setting signal Sa2 for setting the zooming rate of zooming optical system 71, is obtained. Next, a setting signal Sb2 for setting a square-shaped readout zone F2, which circumscribes fluorescent image focusing zone E2 having a round shape, within which fluorescent image Zk is assembled in area P2 of light-receiving zone 61a, so that the center-point C2 thereof (the point at which the diagonal lines intersect) is matched with light axis Z of the optical system focusing the fluorescent image Zk, that is, with the center-point of fluorescent image fluorescent image focusing zone E2, is obtained.

Then, when setting Sa2 is input to zooming optical system 71, the zooming rate thereof is set, and a small fluorescent image Zk having fluorescent image assembly area P2 is assembled within light-receiving zone 61a of MOS type photographing element 61. Then, when setting signal Sb2 is input to MOS type photographing element 61, a readout zone F2 containing aforementioned fluorescent image Zk, which has been assembled small within the light-receiving zone 61a thereof, is set within said light-receiving zone 61a.

According to the setting in which the resolution of aforementioned image is lowered, the quantity of light received per pixel is increased and the S/N ratio improved, the signal charge of the pixels contained within readout zone F2 is output from MOS type photographing element 61 as image signal Sg2', input to visible-image signal processing circuit 34a, converted to a visible-image signal and output from fluorescent image photographing unit 300.

The visible-image signal, carrying the image data of fluorescent image Zk, output from visible image data processing circuit 34a, in the same way as in the third embodiment, is photographed by normal-image photographing element 25 and output via visible-image signal processing circuit 34b, and input, combined with the image signal carrying the image data of normal image Zw, to display 400 and output simultaneously on one display screen as a visible image (refer to FIG. 1).

In this way, according to the fourth embodiment of the present invention, by changing the size of the fluorescent image assembled within light-receiving zone of the MOS type photographing element in accordance with the quantity of fluorescent light received at said photographing element, because adjustment can be made so that the quantity of light received per pixel is ensured and resolution of the fluorescent image is improved, the fluorescent image can be photographed as an image having an appropriate quantity of light as well as good resolution, a reading zone neither too small nor too large can be set in accordance with the size of the fluorescent image, whereby efficient initial readout of the fluorescent image becomes possible and the fluorescent image can be photographed as an image having a high S/N ratio.

Note that according to the fourth embodiment, an example in which a readout zone was set as a square-shaped circumscribed in the image focusing zone of the fluorescent image, and the signal charge of the pixels contained within said readout zone were set so as to be read out was given, however, the effect by which the noise produced per pixel is controlled, the quantity of received light increased and the S/N ratio improved can be obtained by focusing the fluorescent image small, and settings such as those described above are not necessarily required. However, if readout zone circumscribed within the image focusing zone of the fluorescent image is set and read out at an early period//prior to the other zones, compared to cases in a larger readout zone has been set read out thereof is performed, because the time for dark noise to accumulate on each pixel receiving the light of the fluorescent image is shortened, an effect by which the fluorescent image can be photographed as an image having a further improved S/N ratio can be obtained.

In addition, according to the third and fourth embodiments, examples were given in which an MOS type photographing element was used as the photographing element, however, if the photographing element used is capable of reading out the signal charge of each pixel in a random manner, it is not necessarily limited to being an MOS type photographing element.

Figure 18:
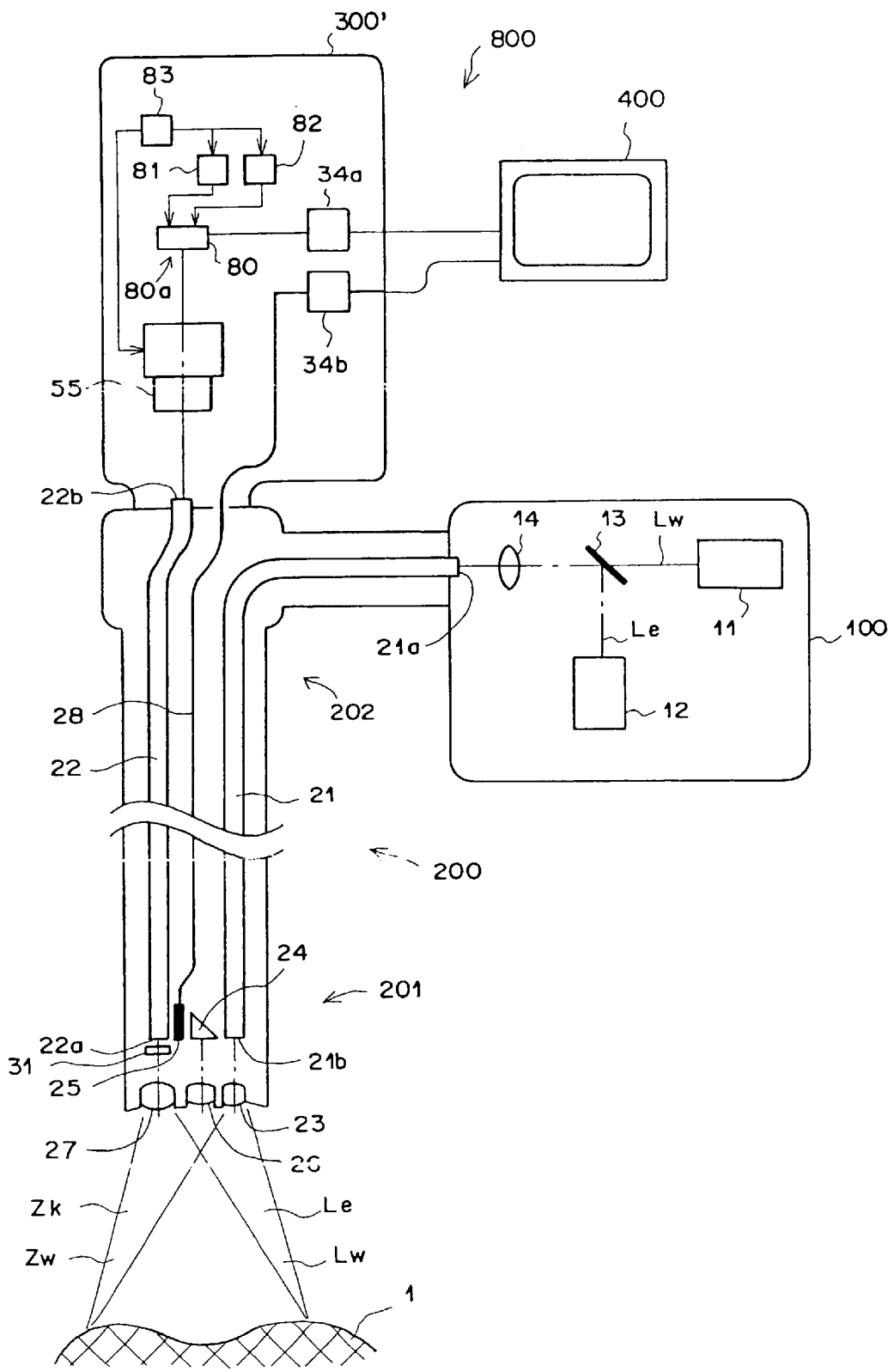
FIG. 18 is a schematic drawing of a fluorescent endoscope according to the fifth embodiment of the present invention.

FIG. 18 is a schematic drawing showing a part of a fluorescent image photographing unit, contained within a fluorescent endoscope apparatus implementing a photographing apparatus for carrying out the photographing method according to the fifth embodiment of the present invention, and structures in common with those of the first embodiment are labeled with the same reference numerals. The photographing apparatus utilized in the fluorescent endoscope apparatus according to the fifth embodiment of the present invention is a frame transfer type CCD for sequentially transferring and reading out the signal charge stored on each pixel, which is provided with a clearing drain.

Figure 19:
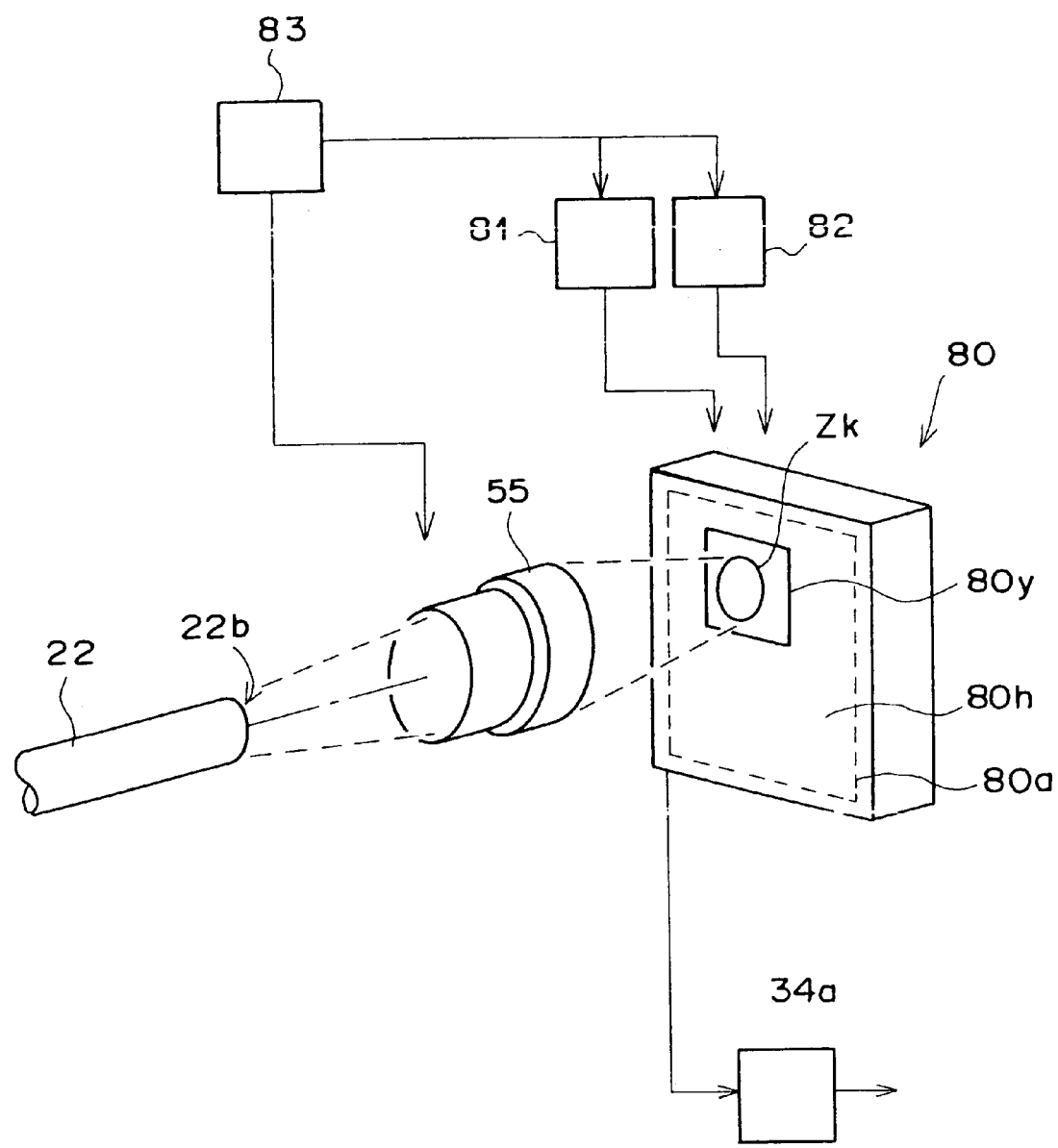
FIG. 19 is a schematic drawing of the main part of a fluorescent image photographing unit.
Figure 20:
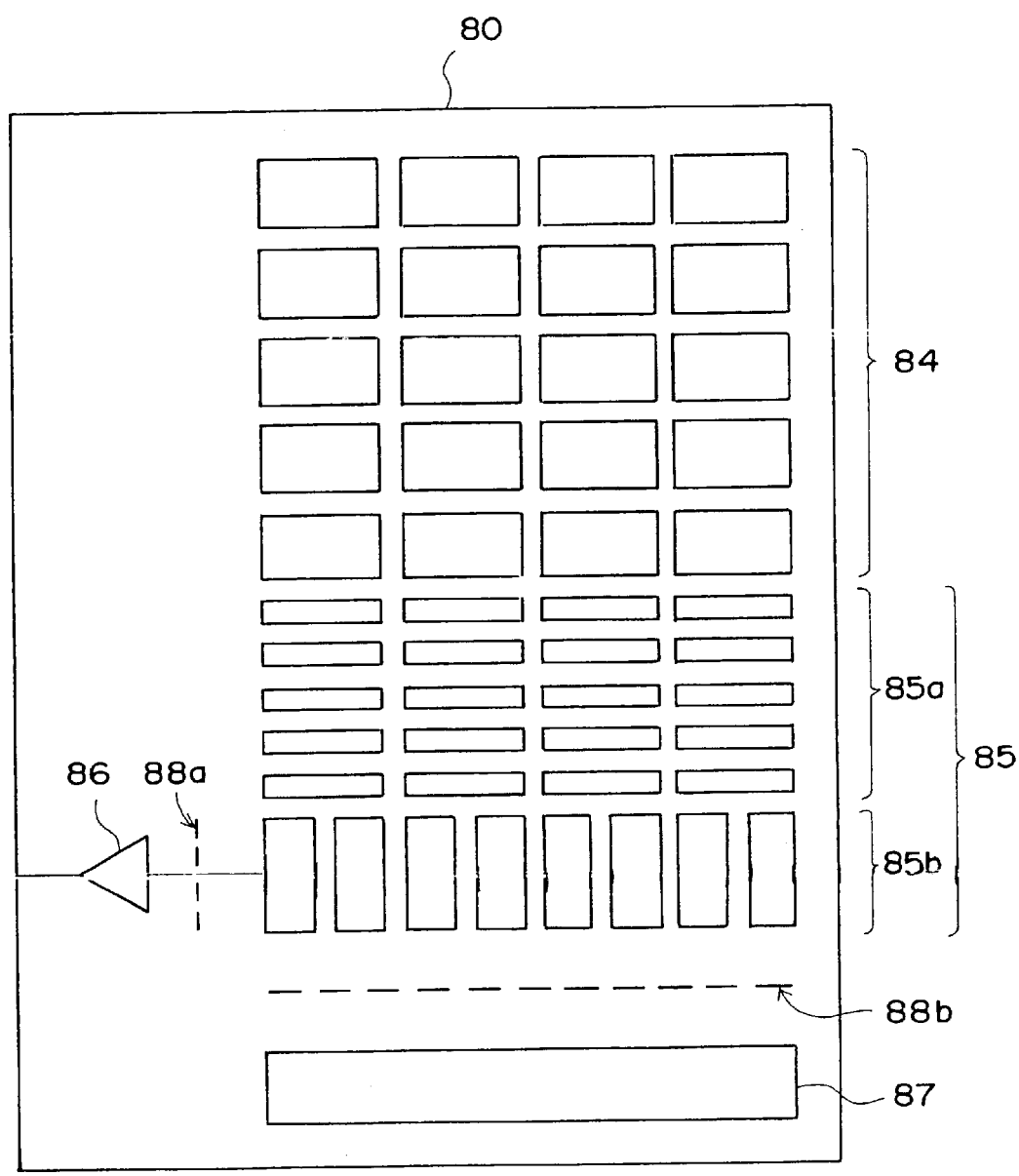
FIG. 20 is a schematic drawing showing the internal structures of a photographing element.

As shown in FIGS. 18 and 19, the fluorescent image photographing unit 300 of the fluorescent endoscope apparatus of the fifth embodiment comprises an image fiber 22, a photographing element 80 for sequentially transferring and reading out the signal charge stored on each pixel, a sequential-readout control means 81 and a gate control means 82 for controlling the readout of the signal charge of the light received by photographing element 80, a zooming optical system 55, which is an assembly means capable of changing the zooming rate, for focusing fluorescent image Zk transferred to output face 22b of the image cable on photographing element 80 (assembled as the light image of the subject), and a readout conditions setting device 83 for setting the zooming rate of zooming optical system 55 as well as the readout zone, and in which the image signal extraction circuit, for extracting the image signal, of the first embodiment has been excluded. The other structures are the same as those of the first embodiment. Note that the light-receiving zone 80a of photographing element 80 is provided with n×m number of individual light-receiving pixels arranged as a matrix.

The fluorescent image Zk transferred to output face 22b of the image fiber is focused on readout zone 80y, which is formed from ½ or less of the total number of light-receiving pixels of light-receiving zone 80a.

As shown in FIG. 18, photographing element 80 comprises a photoelectric conversion portion 84 formed of a number n×m light-receiving pixels arranged as a matrix and provided with a function for photoelectrically converting the light received at each pixel and storing said photoelectrically converted light as a signal charge on each pixel and a function for grouping together and vertically transferring the entire signal charge stored on the light-receiving pixels, a charge transfer portion 85 for sequentially transferring the signal charge from photoelectric conversion portion 84, which has been grouped together, vertically transferred and stored on each light-receiving pixel, a sequential-readout portion 86 for converting to an electric image signal and reading out the signal charge, of readout zone 80y, sequentially transferred by charge transfer portion 85, a clearing drain 87 for discarding outside of charge transfer portion 85 the signal charge stored on the pixels contained in non-readout zone 80h outside said readout zone 80y, a first gate 88a disposed between charge transfer portion 85 and sequential-readout portion 86 for controlling passage of the signal charge transferred by charge transfer portion 85 to sequential-readout portion 86 (that is, opening and closing of the gate is performed to control passage of the signal charge), and a second gate 88b disposed between charge transfer portion 85 and clearing drain 87 for controlling passage of the signal charge transferred by charge transfer portion 85 to clearing drain 87.

Charge transfer portion 85 is provided with a charge transfer storage portion formed of a number of pixels n×m arranged as a matrix for storing a signal charge, and a horizontal charge transfer portion 85b formed of a number of pixels m arranged in a straight line. Charge transfer storage portion 85a stores the signal charge grouped together and vertically transferred by charge transfer portion 84, and transfers said stored signal charge to horizontal transfer portion 85b 1 horizontal line at a time. Horizontal transfer portion 85b, by again horizontally transferring the signal charge transferred 1 horizontal line at a time from charge transfer storage portion 85a, has a function of grouping together and discarding, and a function of transferring said horizontal 1 line signal charge to sequential-readout portion 86.

Sequential readout control means 81 inputs the setting signal output from readout conditions setting device 83, and based on said setting signal, controls charge transfer storage portion 85a, horizontal transfer portion 85b and sequential-readout portion 86, and outputs vertical transfer commands, horizontal transfer commands, etc.

For cases in which a vertical transfer command is output from sequential readout control means 81, the charge transfer storage portion 85a and horizontal transfer portion 85b into which said command has been input transfer said horizontal 1 line signal charge in a vertical direction. That is to say, these signal charges are transferred 1 horizontal line at a time from charge transfer storage portion 85a to horizontal transfer portion 85b, and to clearing drain 87 and discarded.

For cases in which a horizontal transfer command is output from sequential readout control means 81, the charge transfer storage portion 85a and horizontal transfer portion 85b into which said command has been input cease said vertical transferring and transfer the 1 horizontal line signal charges transferred to horizontal transfer portion 85b toward sequential-readout portion 86 in a horizontal direction. Then, these signal charges are converted to electric image signals by sequential-readout portion 86 and read out.

Gate control means 82 inputs a binning processing conditions setting signal from readout conditions setting device 83, and in accordance with said input binning processing conditions, outputs to first gate 88a and second gate 88b signal carrying out control of the opening and closing thereof.

That is to say, for cases in which vertical binning processing is performed on an image signal, by closing first gate 88a when a vertical-transfer command has been output from sequential readout control means 81, the image signal transferred from charge transfer storage portion 85a to horizontal transfer portion 85b, and the 1 line portion signal charges transferred vertically toward clearing drain 87 cannot pass through second gate 88b and are sequentially multiplied and stored in horizontal transfer portion 85b.

On the other hand, for cases in which horizontal binning processing is performed on an image signal, by closing second gate 88b when a horizontal-transfer command has been output from sequential readout control means 81, the 1 line portion signal charges transferred horizontally toward sequential-readout portion 86 cannot pass through first gate 88a and are sequentially multiplied and stored in horizontal transfer portion 85b.

Next, the operation of the fifth embodiment will be explained.

Figure 21:
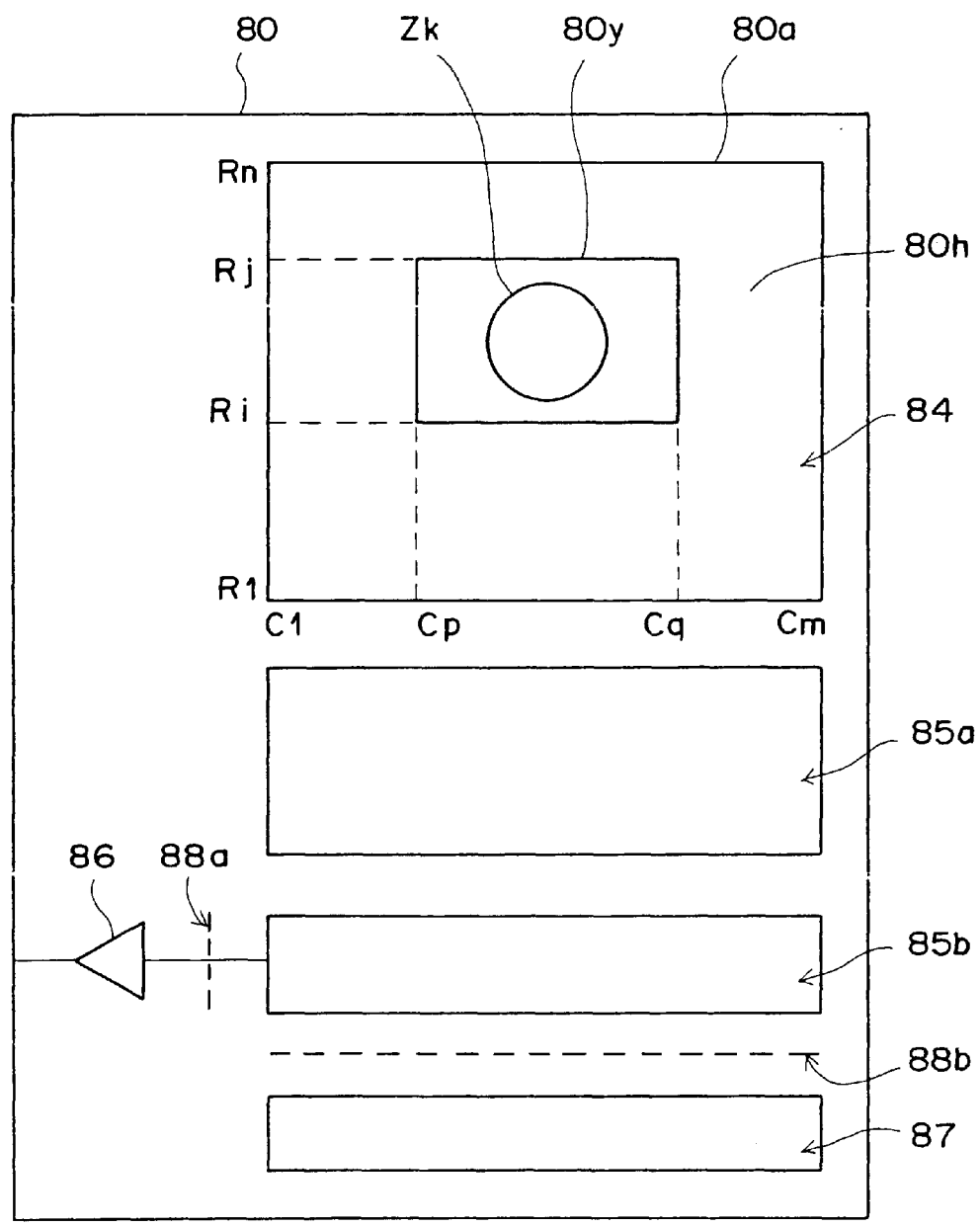
FIG. 21 shows the range of a readout zone set within the light-receiving zone of a photographing element.

Readout conditions setting device 83 outputs readout conditions setting signal to zooming optical system 55, sequential readout control means 81 and gate control means 82. As shown in FIG. 21, by these readout conditions, binning processing conditions are set so that readout zone 80y formed of ½ or less of the total number of light-receiving pixels of light-receiving zone 80a is set, and a 2 vertical pixel×2 horizontal pixel binning processing is performed on a circular fluorescent image Zk focused on said readout zone 80y.

More specifically, sequential readout control means 81, into which the setting signal output from readout conditions setting device 83 for setting readout zone 80*y* has been input, recognizes and records the position of all the light-receiving pixels contained within said readout zone 80*y*. Zooming optical system 55, into which the setting signal output from readout conditions setting device 83 for setting the zooming rate has been input, sets the zooming rate so that the circular fluorescent image Zk formed on output face 22*b* of the image fiber is assembled as a circular fluorescent image Zk within light-receiving zone 80*a*. Gate control means 82 and sequential readout control means 81, into which the setting signal output from readout conditions setting device 83 for setting the binning processing have been input, recognize and record that a 2 vertical pixel×2 horizontal pixel binning processing is to be performed on the signal charge transferred by charge transfer portion 85.

Note that as shown in FIG. 21, readout zone 80*y* is set so that it is formed by light-receiving pixels contained in rows Ri–Rj and columns Cp–Cq within light-receiving zone 80*a*, which is formed of n×m number of individual pixels arranged in rows R1–Rn and columns C1–Cm.

Hereinafter, taking the position of the light-receiving pixels of light-receiving zone 80*a*, which are arranged as a matrix, as the standard, when referring to each signal charge the corresponding position of aforementioned each light receiving pixel will be referred to: for example, the signal charge of row Ry, or the signal charge of column Cx, etc.

As described above, signal charge readout processing is initiated when each readout condition has been set by the setting signals from readout conditions setting device 83. Note that in the initial state of said initiated reading out, first gate 88*a* and second gate 88*b* are open: in the state in which signal charges can pass therethrough.

Figure 22:
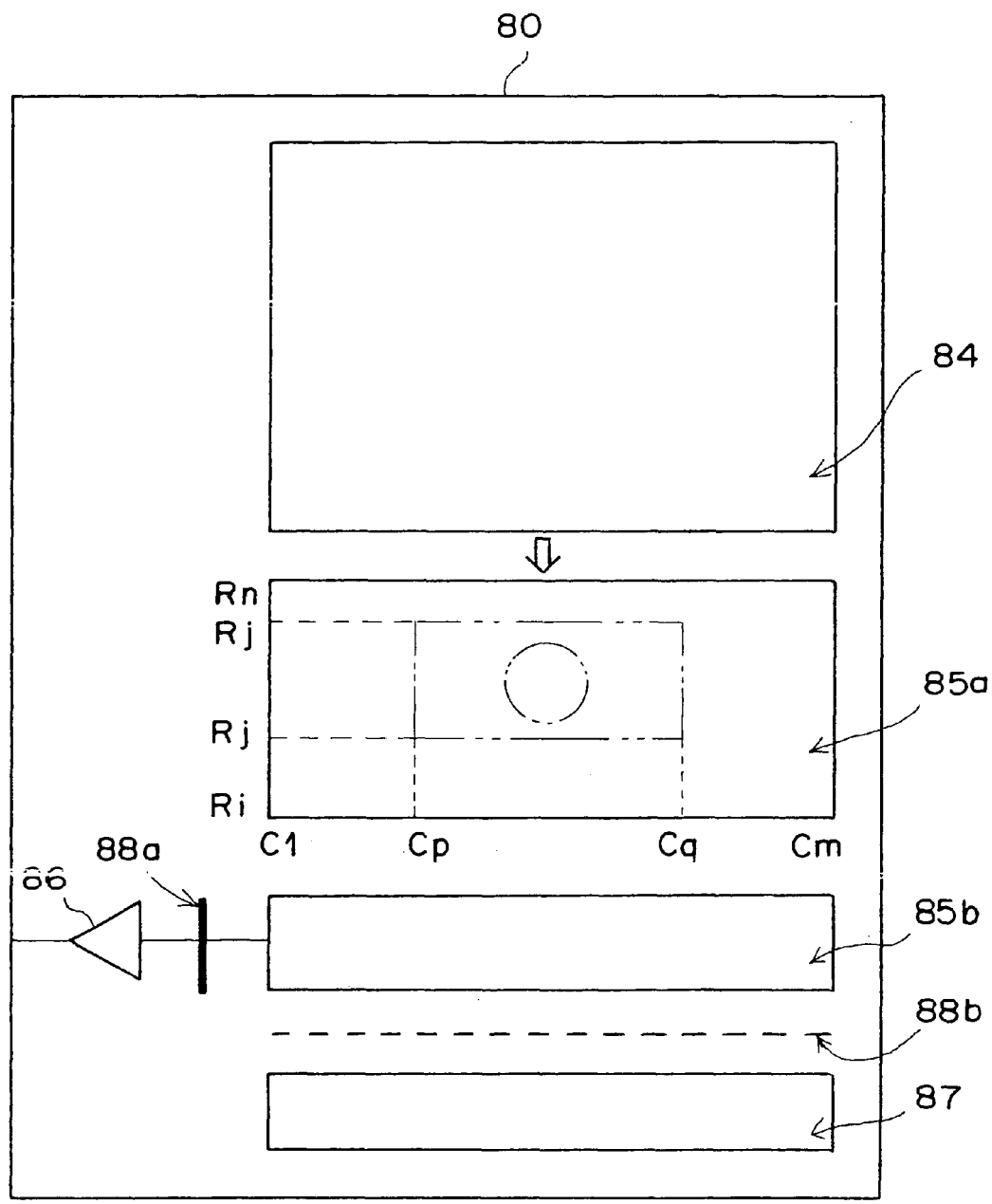
FIG. 22 shows a charge transfer and storage portion in the state in which a signal charge has been transferred thereto from the light-receiving zone.

When readout of the signal charge is initiated, first, the signal charge stored on the n×m number of individual pixels, from which light-receiving zone 80*a* is formed, is transferred to charge transfer storage portion 85*a*, which can store the entire signal charge stored on n×m number of individual pixels as such en mass (frame transfer) as a 1 screen portion (a 1 frame portion) (refer to FIG. 22).

The 1 screen portion signal charge transferred to and stored in charge transfer storage portion 85*a* is vertically transferred 1 horizontal line at a time upon issuance of a vertical transfer command from sequential readout control means 81.

Whether or not the signal charge stored on the light-receiving pixels within readout zone 80*y* is contained in these 1 horizontal line image signals is remembered by sequential readout control means 81, and because the signal charge due to light received within readout zone 80*y* is not contained in the signal charge of the first 1 horizontal line R1 of non-readout zone 80*h*, the signal charge from this first 1 horizontal line is vertically transferred again from horizontal transfer portion 85*b* to clearing drain 87 and discarded.

Also, because the photoelectrically converted signal charge of light received in readout zone 80*y* is not contained in the signal charge of each of rows R1–Ri of non-readout zone 80*h*, in the same way as described above, each 1 horizontal line of these signal charges is transferred to and discarded in clearing drain 87.

Then, when the 1 horizontal line signal charges of rows Ri–R1 that have been transferred to horizontal transfer portion 85*b* are transferred to clearing drain 87 and discarded, the signal charge of row Ri is transferred to horizontal transfer portion 85*b*. Because the signal charge of this 1 horizontal line, row Ri, contains a readout signal charge photoelectrically converted by pixels contained within readout zone 80*y*, said readout signal charge is subjected to binning processing in the vertical transfer direction (refer to FIG. 23).

Figure 24:
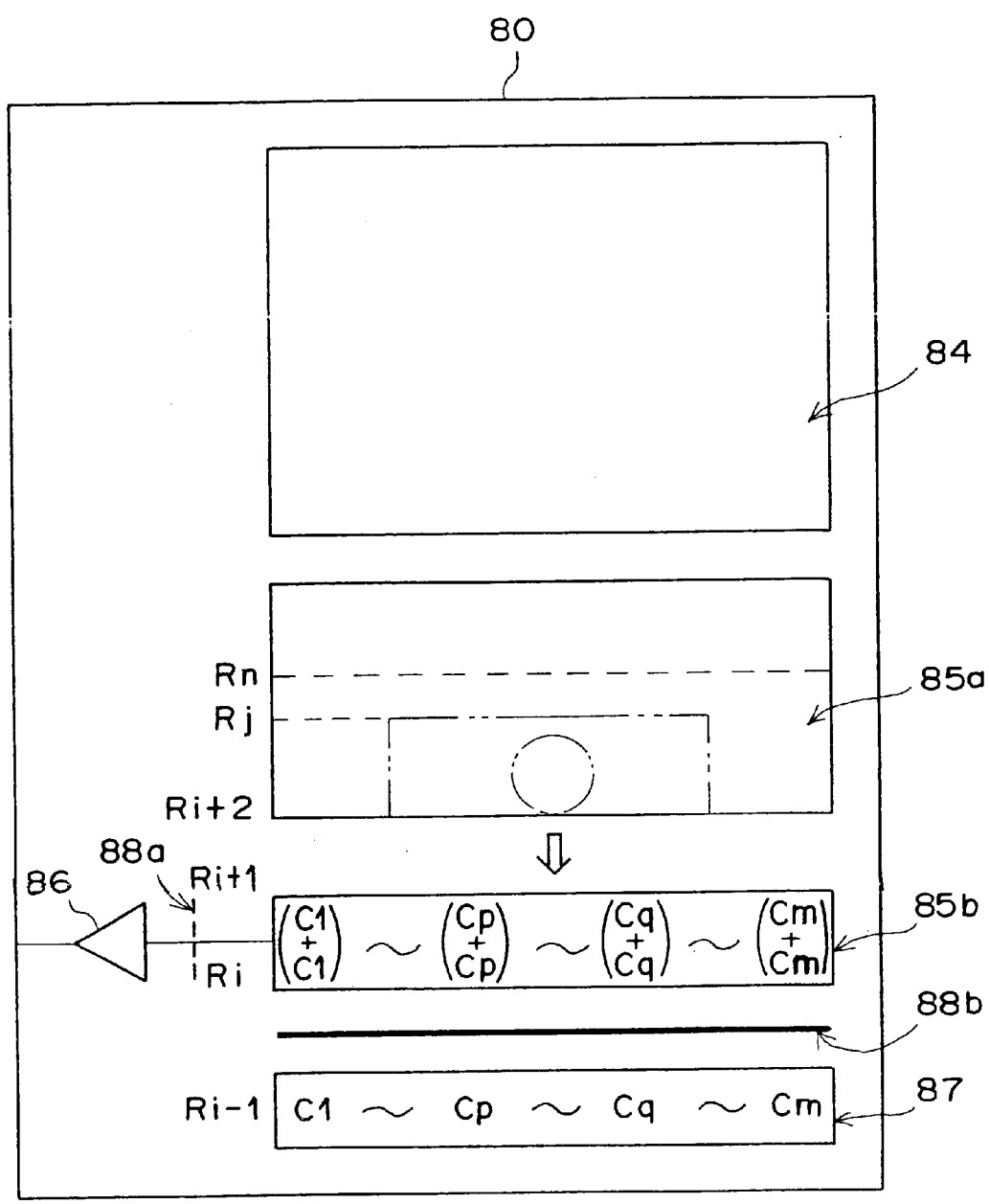
FIG. 24 shows a state in which a signal charge is subjected binning processing in the vertical transfer direction.

That is to say, gate control means 82 outputs a control signal and second gate 88*b* closes, the 1 horizontal line signal charge of row Ri transferred to horizontal 8 transfer portion 85*b* remains at horizontal transfer portion 85*b*, and the next 1 line horizontal signal charge, Ri+1, is vertically transferred, multiplied and stored (refer to FIG. 24).

Figure 25:
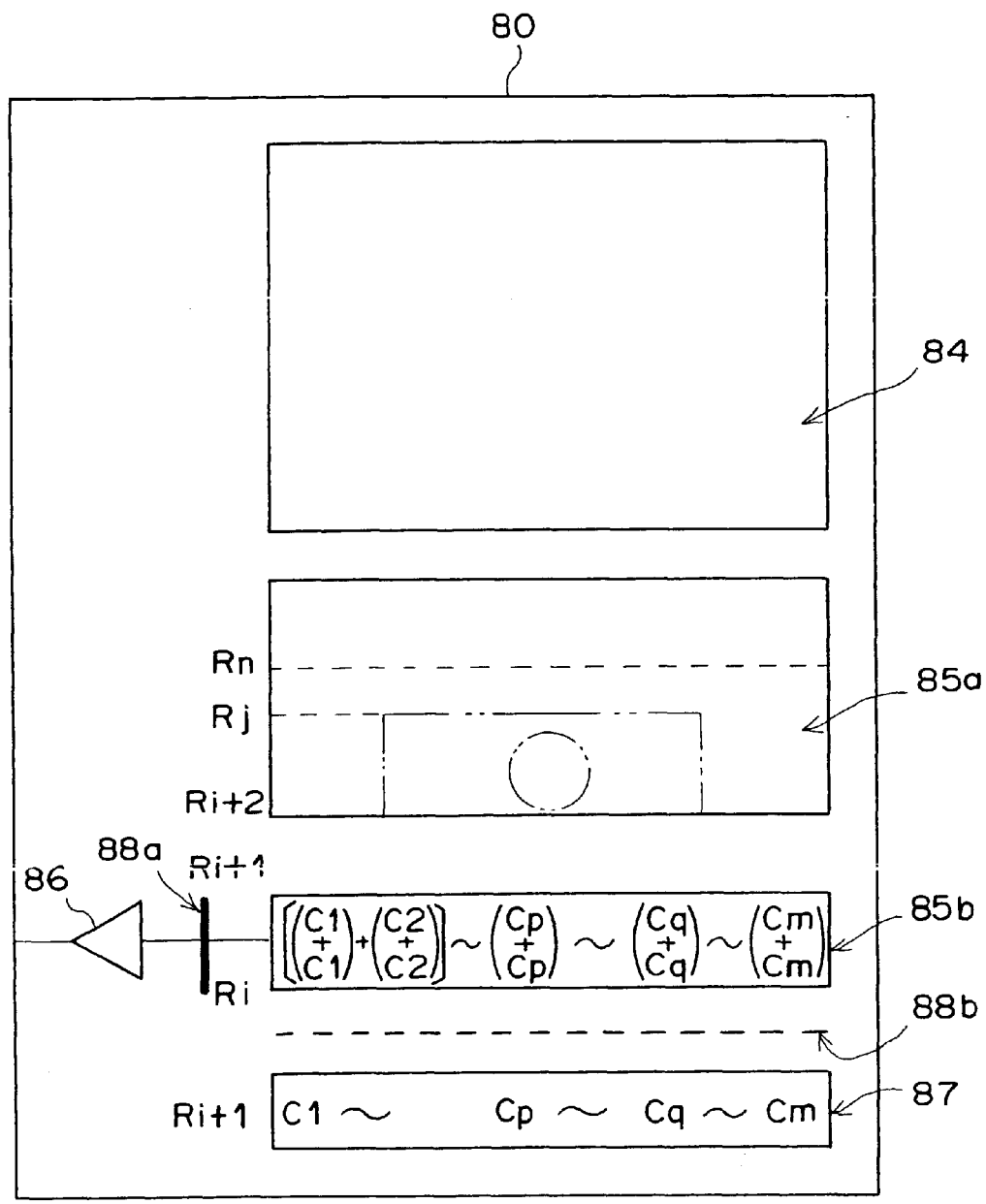
FIG. 25 shows a state in which a signal charge is subjected binning processing in the horizontal transfer direction.

Next, upon issuance of a horizontal transfer command from sequential readout control means 81, said two 1 horizontal line signal charges stored within horizontal transfer portion 85*b* are transferred toward sequential-readout portion 86 in the horizontal direction, however, at this point, first gate 88*a* is closed by gate control means 82, and the signal charge of columns C1 and C2 stored within horizontal transfer portion 85*b* is multiplied and stored (refer to FIG. 25). When multiplication of the signal charges is complete, first gate 88*a* opens, and the signal charge contained on said rows Ri and Ri+1 as well as columns C1 and C2, which have been subjected to 2×2 binning processing, are output to sequential-readout portion 86.

Because the signal charge subjected to binning processing contained on rows Ri and Ri+1 as well as columns C1 and C2 does not contain a signal charge photoelectrically converted by pixels contained within readout zone 80*y* (because it is a signal charge of non-readout zone 80*h*), these residual signal charges are read out as null by sequential-readout portion 86 and no subsequent processing is performed.

Afterward, first gate 88*a* is again closed, and next the signal charge of columns C3 and C4 within horizontal transfer portion 85*b* is multiplied, and subjected to binning processing in the same way as described above.

In this way, the signal charges stored within horizontal transfer portion 85 on columns C1–Cq are subjected 2 at a time to binning processing in a horizontal direction, however, because these signal charges within columns C1–Cp−1 are signal charges of the non-readout zone 80*h*, said signal charges are read out as null by sequential-readout portion 86 and no subsequent processing is performed, and the signal charge of columns Cp–Cq are read out as readout signal charges by sequential-readout portion 86, after which said signal charges are output to visible-image signal processing circuit 34*a*, converted to display signals and displayed on display 400.

In this way, upon completion of reading out of the signal charge stored on rows C1–Cq of horizontal transfer portion 85*b*, because the signal portion of the remaining rows Cq+1-Cm are signal charges of the non-readout zone 80*h*, second gate 88*b* opens, a vertical transfer command is output from sequential readout control means 81, and as shown in FIG. 26, the signal charges remaining in the 1 horizontal line portion of horizontal transfer portion 85*b* are grouped together, transferred to clearing drain 87 and discarded, and horizontal transfer portion 85*b* is cleared.

When readout of the signal charges of rows Ri–Rj of readout zone 80*y* is completed in this way, because the signal charges of the next row Rj+1 through the last row Rn are signal charges of non-readout zone 80*h*, in the same way as the processing performed on the signal charges of rows R1–Ri−1, said signal charges of rows Rj+1–Rn are discarded into clearing drain 87.

In addition, aforementioned binning processing is not limited to a 2 vertical pixel×2 horizontal pixel binning processing; the effect of further reducing the dark noise is obtained by performing any binning processing grouping.

Further, if the time required for reading out the signal charge of 1 pixel is already set uniformly at, for example, $\frac{1}{60}$ seconds, the portion of readout time saved by use of the clearing drain, the readout frequency used when reading out, as an image signal, the readout signal charge of readout zone 80y can be set low and readout can be performed slowly, and the readout noise can be further reduced.

Still further, if the readout zone in which fluorescent image Zk is assembled is set close to the readout port of the photographing element, because the charge stored in the readout zone can be read out even faster, and the dark noise can be further reduced.

Further still, when the signal charge stored on the light-receiving pixels of the non-readout zone are readout as null by sequential-readout portion 86, if the standard clock frequency for controlling the timing of the charge transfer operation is made faster and readout is carried out at high speed, because the time required for reading out a 1 frame portion can be further shortened, an effect by which the dark noise mixed with the readout signal charge stored on the light-receiving pixels of the readout zone is further reduced can be obtained.

Figure 27:
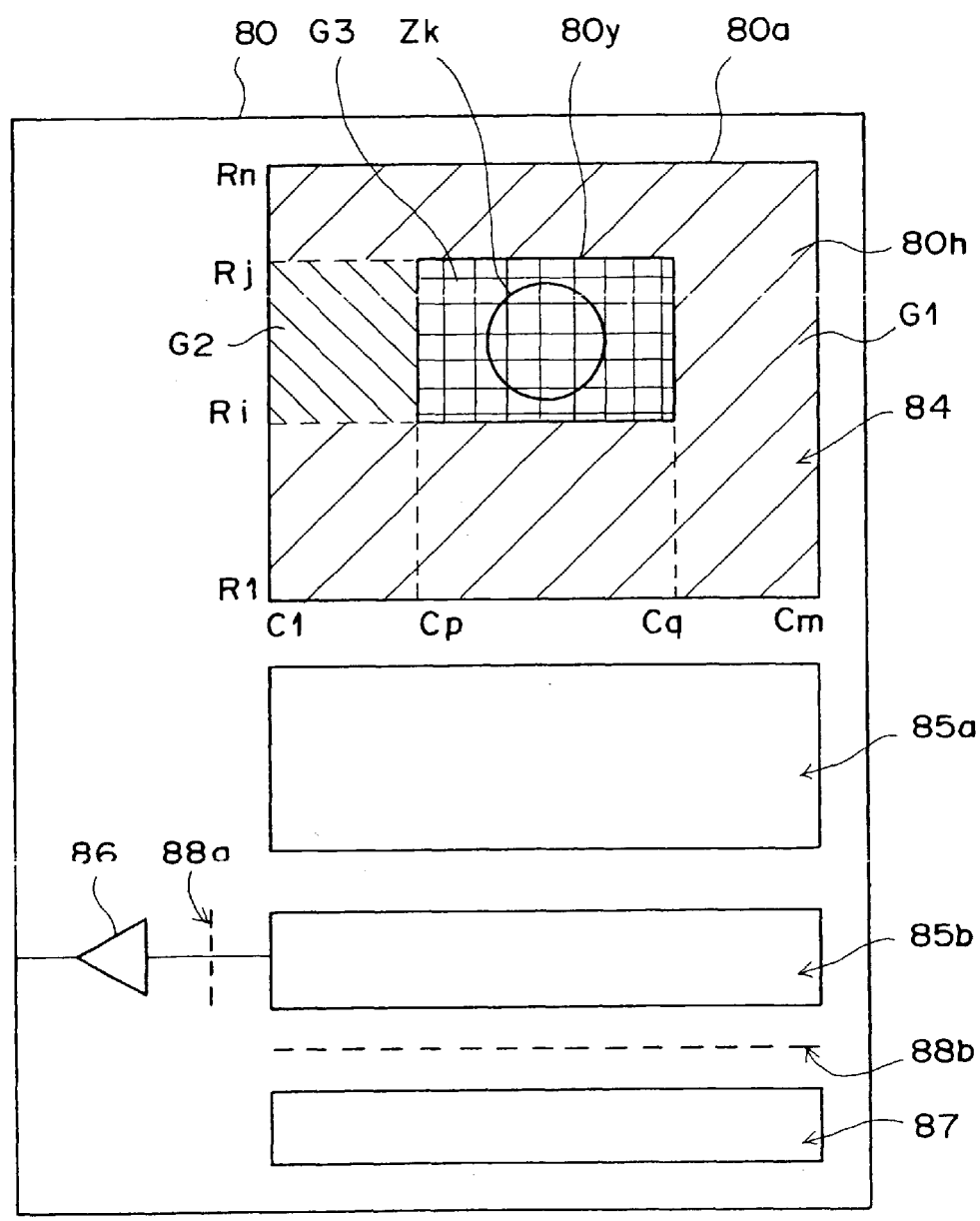
FIG. 27 shows a comparison between a zone read out as a signal charge and the readout zone.
Figure 28:
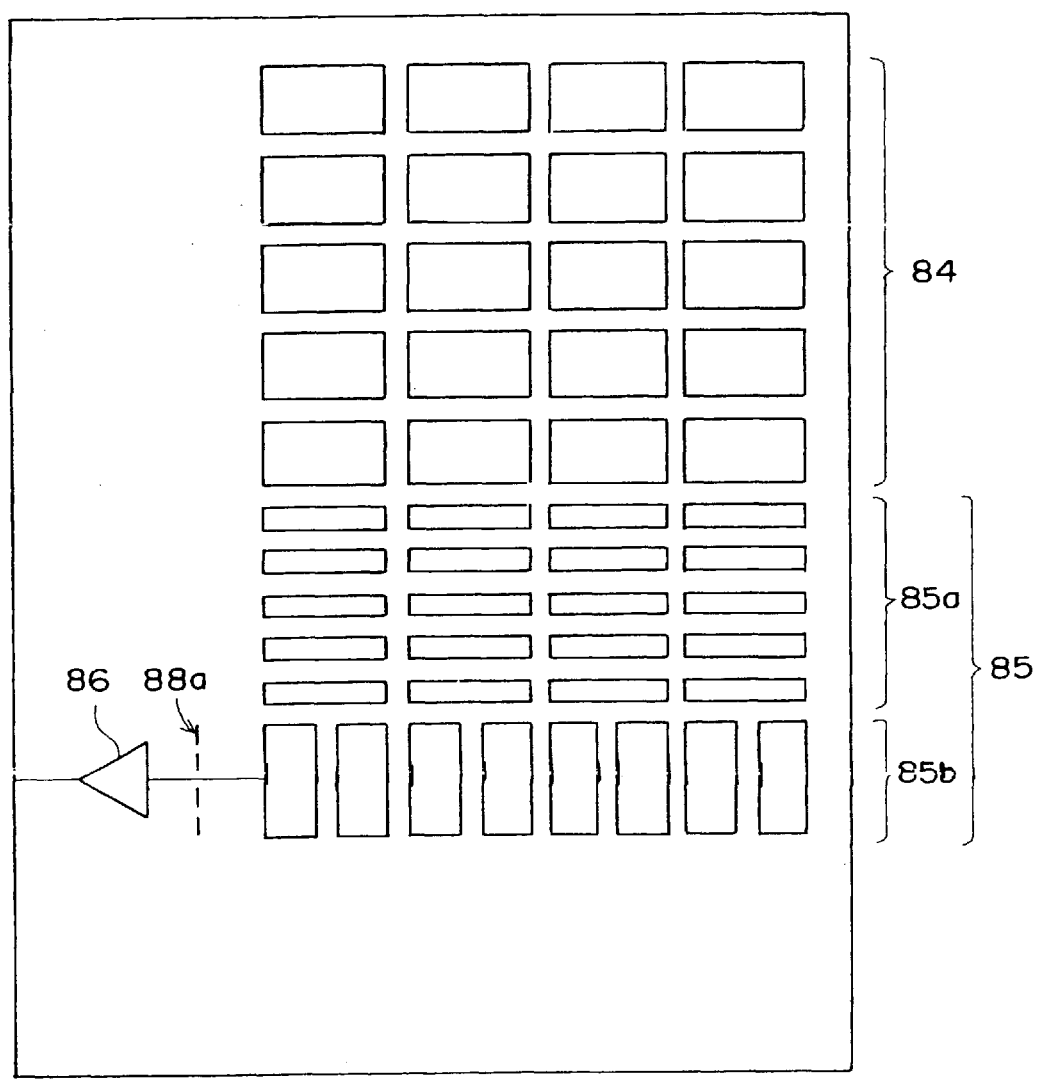
FIG. 28 is a schematic drawing of a photographing element not provided with a clearing drain.

Also, as shown in FIG. 28, with the clearing drain and second gate excluded from the photographing element, as shown in FIG. 27, the signal charge stored on the light-receiving pixels within the non-readout zone, which is formed of zones G1 and G2, can be read out as null by sequential-readout portion 86. Note that even for cases in which second gate 88b has been excluded, because the signal charge vertically transferred from charge transfer storage portion 85a can be multiplied and stored in horizontal transfer portion 85b, by control of binning processing in the horizontal direction by first gate 88a, binning processing in the horizontal as well as the vertical direction can be performed.

In addition, for reading out the signal charge of the readout-zone, it is not necessary that binning processing be performed and the signal charge read out, the signal charge of 1 light-receiving pixel can be read out in the normal way as a 1 pixel portion signal charge.

Further, readout of the signal charge stored on the light-receiving pixels of the non-readout zone as null can be carried out by any method, if said signal charge is not treated as a readout signal charge.

Figure 29:
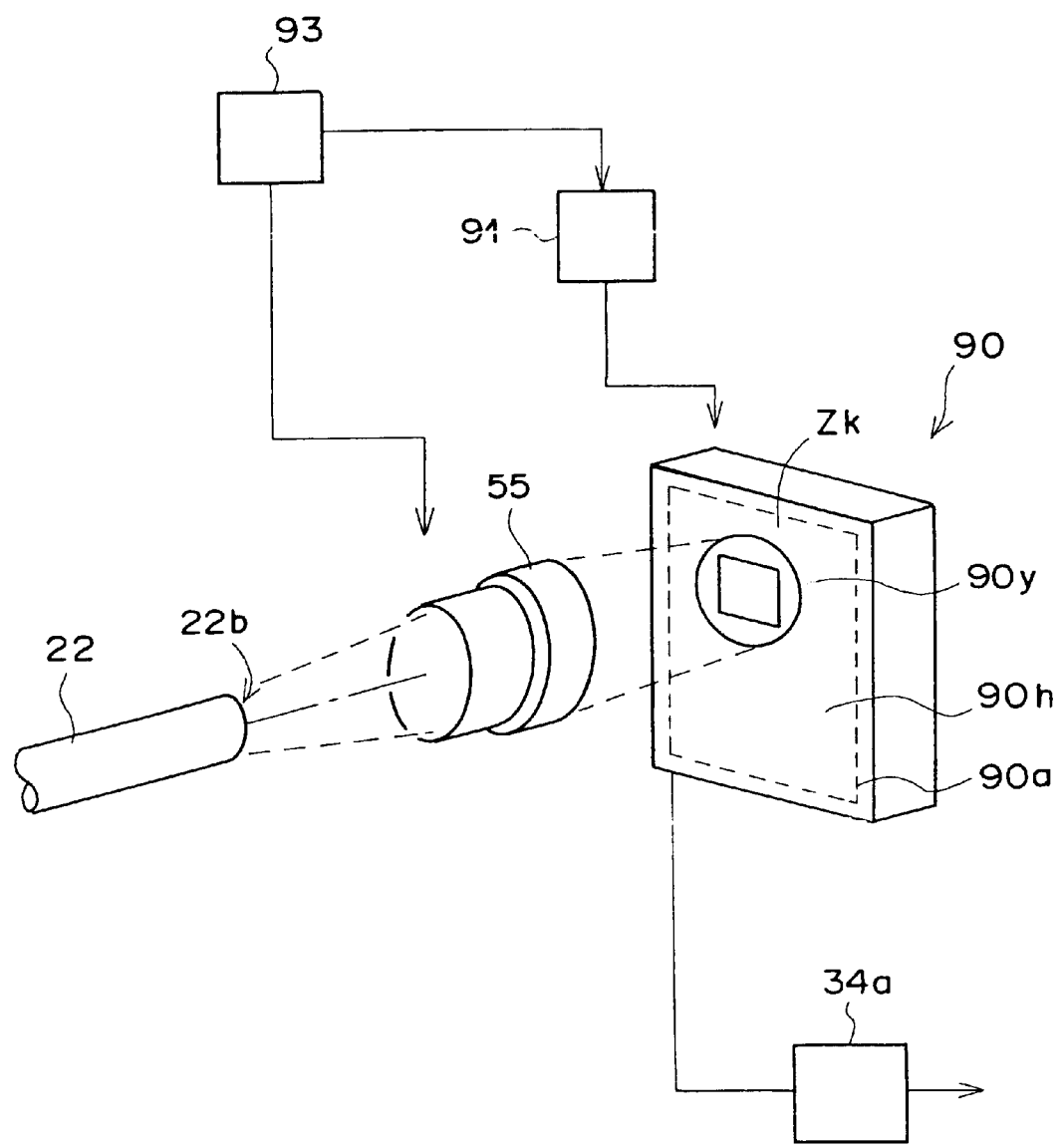
FIG. 29 is a schematic drawing of a fluorescent endoscope according to the sixth embodiment of the present invention.

FIG. 29 is a schematic drawing showing a part of a fluorescent image photographing unit, contained within a fluorescent endoscope apparatus implementing a photographing apparatus for carrying out the photographing method according to the sixth embodiment of the present invention, and structures in common with those of the fifth embodiment are labeled with the same reference numerals. The photographing apparatus utilized in the sixth embodiment is provided with an MOS type photographing element capable reading out, in a random manner, the signal charge stored on each pixel.

As shown in FIG. 29, the fluorescent endoscope of the sixth embodiment comprises an image fiber 22, a photographing element 90 capable of reading out, in a random manner, the signal charge stored on each pixel, a zooming optical system 55, for focusing fluorescent image Zk transferred to output face 22b of the image cable on photographing element 90 (assembled as the light image of the subject), and a readout conditions setting device 93 for setting the zooming rate of zooming optical system 55, as well as the readout zone, and a random readout control means 91, into which the setting signal output from readout conditions setting device 93 representing the readout zone is input, for controlling read out of the signal charge stored on the light-receiving pixels within the readout zone as well as read out of the signal charge stored on the light-receiving pixels contained within the non-readout zone outside of the readout zone, and in which the sequential readout control means and the gate control means of the fifth embodiment have been excluded. The other structures are the same as those of the fifth embodiment.

Zooming optical system 55 focuses the fluorescent image Zk transferred to output face 22b of the image fiber in the readout zone 90y, which is formed of ½ or less of the light-receiving pixels of light-receiving zone 90a.

Figure 30:
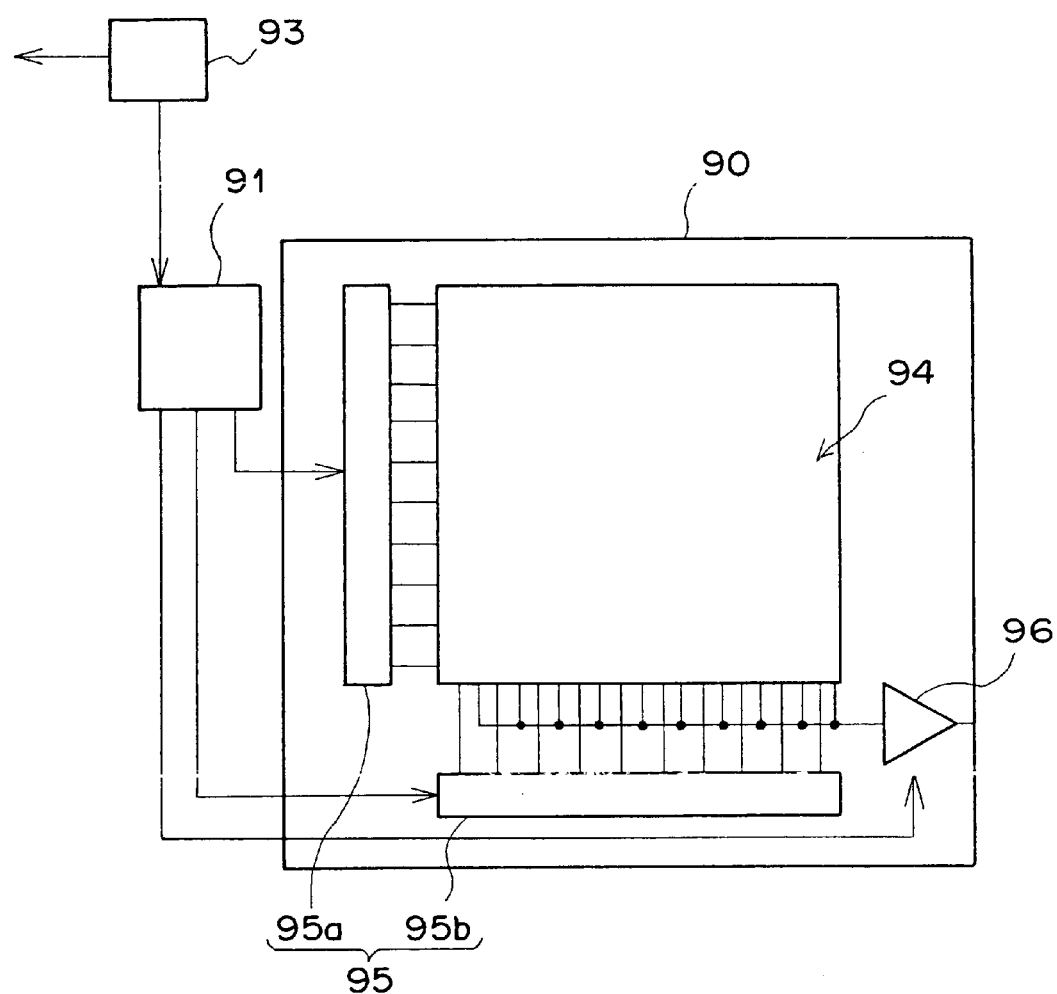
FIG. 30 is a schematic drawing of a photographing element.

As shown in FIG. 30, photographing element 90 comprises a photoelectric conversion portion 94 for photoelectrically converting the light received at each light-receiving pixel within the light-receiving zone to a signal charge and storing said signal charge, a pixel selection portion 95 formed of a row decoder 95a and a column decoder 95b for selecting, in a random manner, pixels from among the light-receiving pixels, and a random readout portion 96 for converting the signal charge of the randomly selected light-receiving pixels to an electric image signal and reading out said electric image signal.

Next, the operation of the sixth embodiment will be explained.

Zooming optical system 55 and random readout control means 91, into which setting signal output from readout conditions setting device 93 for setting the readout conditions have been input, set the readout zone 90y according to said readout conditions, assemble fluorescent image Zk in said readout zone, and set the binning processing conditions so that a 2 vertical pixel×2 horizontal binning processing is performed.

Figure 31:
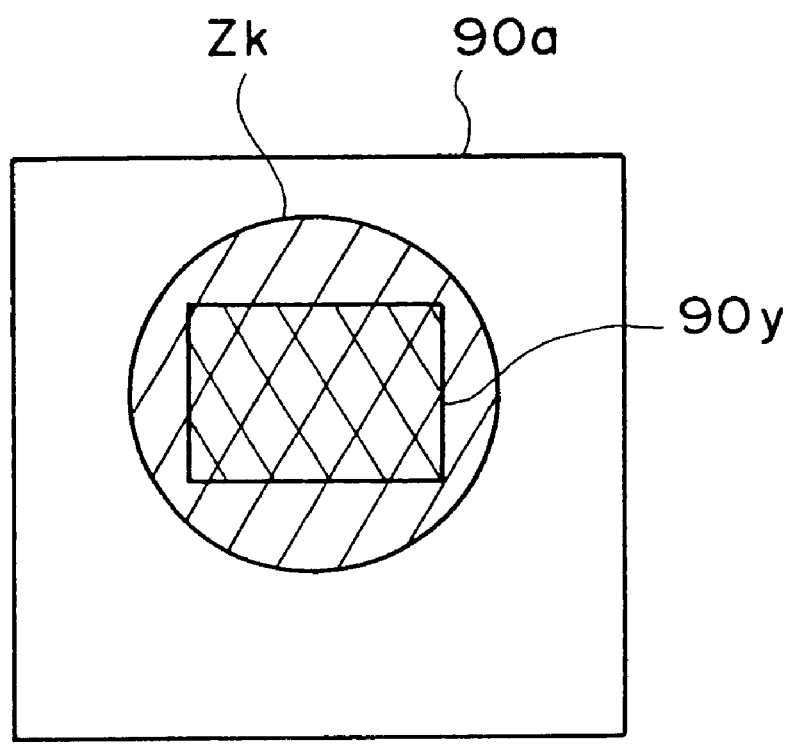
FIG. 31 shows a readout zone and the zone in which a fluorescent image has been assembled.

More specifically, random readout control means 91, into which the setting signal output from readout conditions setting device 93 for setting the readout zone has been input, as shown in FIG. 31, sets the readout zone 90y, which is formed of ½ or less of the total number of light-receiving pixels of light-receiving zone 90a, within said light-receiving zone 90a. On the other hand, zooming optical means 55, into which the setting signal for setting the zooming rate has been input, sets the zooming rate so as to position the fluorescent image Zk to be readout within said readout zone 90y, and the fluorescent image Zk formed on output face 22b of the image fiber is assembled. At this point, for cases in which the image to be read out is 1 portion of the fluorescent image Zk, it doesn't matter if the fluorescent be assembled so that it protrudes out of readout zone 90y.

Next, random readout control means 91 outputs a control signal to pixel selecting portion 95 so that an address of 2 vertical pixel×2horizontal pixel of the light-receiving pixels from within aforementioned set readout zone 90y is specified, and outputs a control signal to read out the signal charge to random readout portion 96. Pixel selecting means 95, into which said control signal has been input, sets the readout signal charge stored on the light-receiving pixels of the 2 vertical pixel×2 horizontal pixel address, within readout zone 90y, specified by pixel selecting means 95 so as to be in a state wherein readout thereof is possible.

Figure 32:
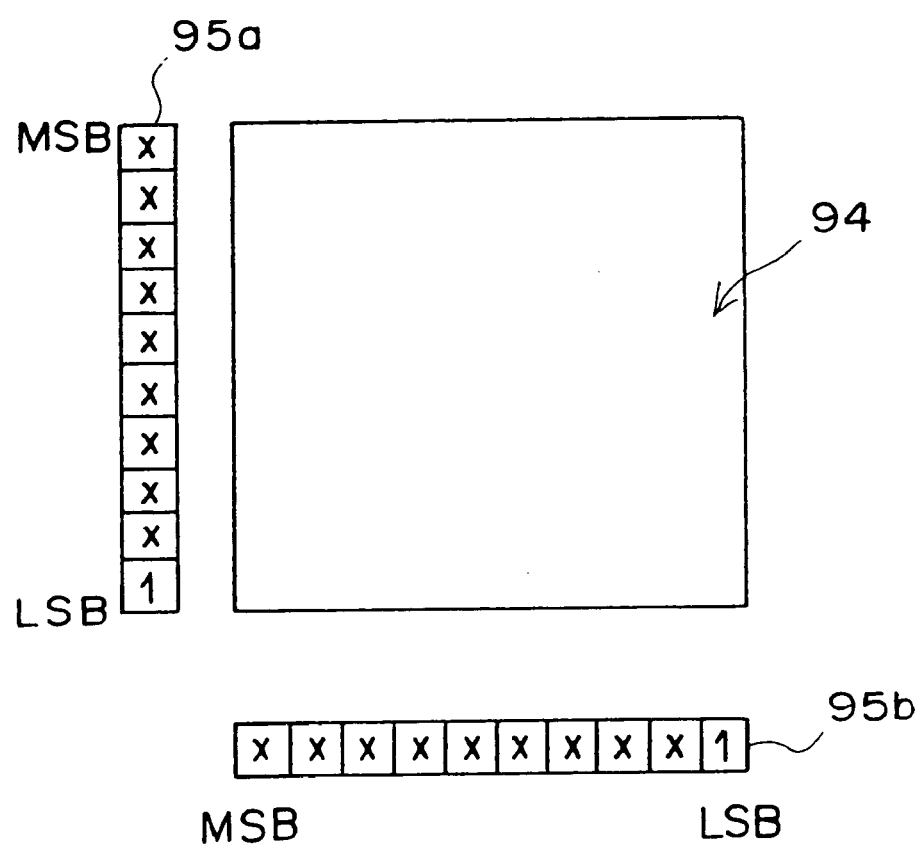
FIG. 32 shows the settings of the pixel selecting portion when a signal charge is subjected to binning processing and read out.

Here, as shown in FIG. 32, in order to set the signal charge of the 4 light-receiving pixels of the 2 vertical pixel×2 horizontal pixel address so as to be in a state wherein readout thereof is possible, row decoder 95a and column decoder 95ba 1 are in normally in a state in which 1 is set in the lowest position (LSB) of the specified address, and the light-receiving pixels of the 2 vertical×2 horizontal pixel address are specified from the upper address.

Random readout portion 96 multiplies (that is, performs binning processing on) the readout signal charge of the 4 light-receiving pixels set so as to be in a state in which readout thereof is possible, is converted to signal charge representing 1 pixel and read out.

In this way, 2 vertical pixel×2 horizontal pixel light-receiving pixels within readout zone 90y are consecutively selected by random readout control means 91, and by converting the readout signal charge of each 2 vertical pixel×2 horizontal pixel light-receiving pixels to an image signal representing a 1 pixel portion and reading out said 1 pixel portion image signal, readout of the signal charge of the light-receiving pixels of readout zone 90y is completed.

The signal readout in the manner described above is output from photographing element 90, and is converted to a visible-image signal by visible-image signal processing circuit 34a and displayed as a visible image on a display.

Figure 33:
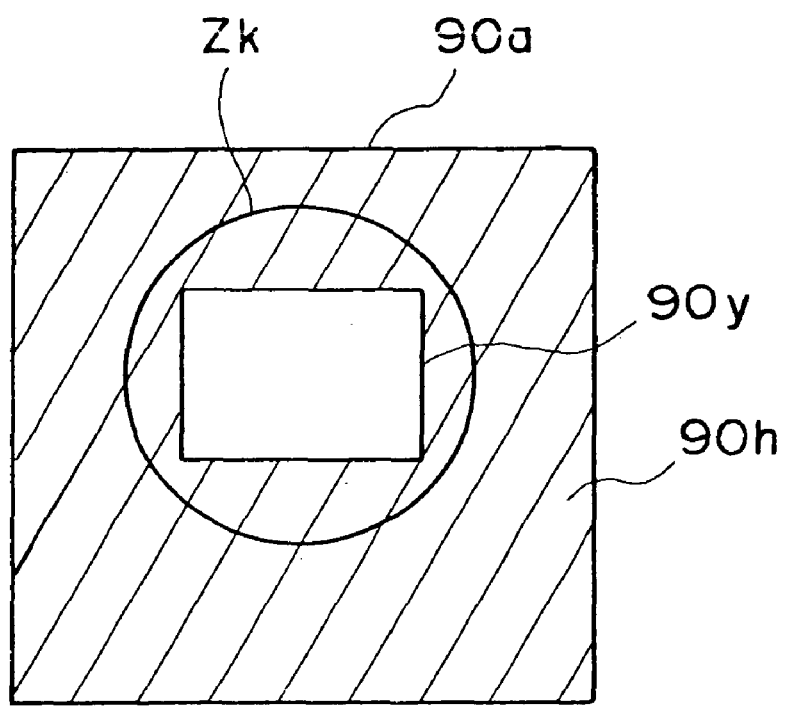
FIG. 33 shows the range of the non-readout zone.

For cases in which the next 1 screen portion is readout from photographing element 90, the residual signal charge stored on the light-receiving pixels of non-readout zone 90h (refer to FIG. 33) and the signal charge stored on the light-receiving pixels of the readout zone after readout of the readout signal charge are grouped together and read out from random readout portion 96 and discarded (cleared), after which, in the same way as described above, readout of the readout signal charge from the readout zone is initiated.

Figure 34:
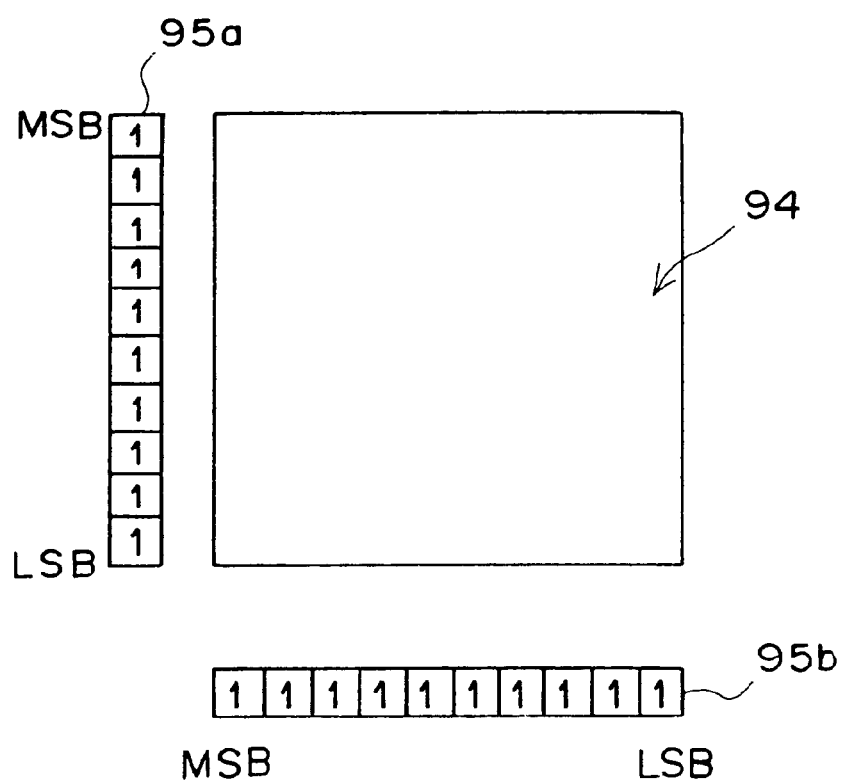
FIG. 34 shows the settings of the pixel selecting portion when the dump charge is grouped together and read out.

That is to say, a group together and readout control signal is output from random readout control means 91, and when said control signal is input to pixel selecting portion 95, the entire signal charge stored on the light-receiving pixels of light-receiving zone 90a is set so as to be in a state wherein readout thereof is possible. Here, in order to set the signal charge contained on all of the light-receiving pixels in a state wherein readout thereof is possible, as shown in FIG. 34, the addresses of row decoder 95a and column decoder 95b are all set so that from the highest position (MSB) to the lowest position (LSB), all are put in a state of 1.

Random readout portion 96 groups together and reads out the signal charge of all of the light-receiving pixels of light-receiving zone 90a, which has been set in a state wherein read out thereof is possible, and the entire signal charge of all of the light-receiving pixels of light-receiving zone 90a is discarded.

In this way, because the processing time for reading out a 1 screen portion of signal charge is shortened and readout of the signal charge of the light-receiving pixels of the readout zone can be completed rapidly, the quantity of dark noise, which accumulates with the passage of time, can be reduced, in addition to which, by grouping together and discarding the residual signal charge stored on the light-receiving pixels of the non-readout zone, the occurrence of blooming, which occurs due to the continuous accumulation of signal charge on the light-receiving pixels, can be prevented.

Note that aforementioned binning processing is not limited to a 2 vertical×2 horizontal pixel binning processing, and the effect by which the readout noise is further reduced can be obtained by use of any binning processing grouping. Further, it is not necessary to perform binning processing when performing the readout described above.

In addition, it is not necessary that the residual signal charge stored on the light-receiving pixels of non-readout zone and the signal charge stored on the light-receiving pixels of the readout zone after readout of the readout signal charge be grouped together and read out. Although the readout time is lengthened, as shown in FIG. 35, pluralities of pixels grouped together in blocks A1, A2, A3, . . . C2, C3, and each said block may be read out, or alternatively, the signal charge may be read out 1 pixel at a time (pixel by pixel).

Further, according to the fifth and sixth embodiments described above, the fluorescent image focused on the output face of the image fiber was the subject of photographing, however, it is also to implement the present invention for cases in which the image of the subject is assembled directly on the photographing element, not via an image fiber, and photographed by an electron endoscope. In addition, the subject of photographing is not limited to images formed by fluorescent light, reflected-light images formed of the light reflected from a subject illuminated with normal light can also be the subject of photographing: For example, it is possible to apply the present invention for use with an infrared camera, etc., for photographing the light image of a body in a dark place illuminated with a faint light as an image with a high S/N ratio. Further, the optical means for focusing the fluorescent image is not required to be a zooming optical means, the fluorescent image may be assembled by an optical means having a fixed magnification.

What is claimed is:

1. A photographing method in which fluorescent light emitted by a living-tissue subject that has been illuminated by stimulating light enters an image fiber and is guided toward the output face of said image fiber, and the fluorescent image formed at the output face of the image fiber is focused on the light-receiving zone of a photographing element and photographed by said photographing element, wherein the relationship between the number of pixels Nf forming the fluorescent image on the output face of the image fiber and the number of pixels Nd receiving the light of the fluorescent image assembled within the light-receiving zone of the photographing element satisfy the condition expressed by the formula: Nf×4>Nd.

2. A photographing method as defined in claim 1, wherein
   a front-exposure type photographing element is employed as said photographing element, and at normal temperature or lower, the fluorescent image is photographed under photographing conditions set so that the sum of the number of electrons of readout noise produced on each pixel within the light-receiving zone receiving the light of a fluorescent image and the number of electrons of dark noise is 10 or less.

3. A photographing method as defined in claim 1 or 2, wherein
   a rear-exposure type photographing element is employed as said photographing element, and at normal temperature or lower, the fluorescent image is photographed under photographing conditions set so that the sum of the number of electrons of readout noise produced on each pixel within the light-receiving zone receiving the light of a fluorescent image and the number of electrons of dark noise is 20 or less.

4. A photographing method as defined in claim 1 or 2, wherein
   said fluorescent image is focused such that the number of the light-receiving zone receiving the light of the fluorescent image is 40,000 or less, and said fluorescent image is photographed.

5. A photographing method as defined in claim 3, wherein
   said fluorescent image is focused such that the number of the light-receiving zone receiving the light of the fluorescent image is 40,000 or less, and said fluorescent image is photographed.

6. A photographing method as defined in claim 1 or 2, wherein
   the size of the fluorescent image focused on the light-receiving zone of the photographing element is changed corresponding to the quantity of light of said fluorescent image received at said photographing element.

7. A photographing method as defined in claim 3, wherein the size of the fluorescent image focused on the light-receiving zone of the photographing element is changed corresponding to the quantity of light of said fluorescent image received at said photographing element.

8. A photographing method as defined in claim 4, wherein the size of the fluorescent image focused on the light-receiving zone of the photographing element is changed corresponding to the quantity of light of said fluorescent image received at said photographing element.

9. A photographing method as defined in claim 5, wherein the size of the fluorescent image focused on the light-receiving zone of the photographing element is changed corresponding to the quantity of light of said fluorescent image received at said photographing element.

10. A photographing method as defined in claim 1 or 2, wherein
for cases in which said photographing element is capable of reading out in a random manner the signal charge stored on each pixel, a readout zone narrower than said light-receiving zone and which contains the fluorescent image is set within said light-receiving zone, and readout of said readout zone is performed prior to readout of other zones within said light-receiving zone.

11. A photographing apparatus comprising:
an optical system for directing fluorescent light emitted from a living-tissue subject illuminated by stimulating light into an image fiber, wherein said fluorescent light is guided to the output face of the image fiber, an image focusing means for focusing on the light-receiving zone of the photographing element the fluorescent image formed by the fluorescent light guided to the output face of the image fiber, and a photographing means for photographing the fluorescent image focused on the light-receiving zone thereof, wherein
said fluorescent image is focused on said light-receiving zone, wherein the relationship between the number of pixels Nf forming the fluorescent image on the output face of the image fiber and the number of pixels Nd receiving light of the fluorescent image assembled within the light-receiving zone of the photographing element satisfies the condition expressed by the formula: Nf×4>Nd.

12. A photographing apparatus as defined in claim 11, wherein
said photographing element is provided as a front-exposure type photographing element, in which the photographing conditions are set so that at normal temperature or lower the sum of the number of electrons of readout noise produced on each pixel within the light-receiving zone receiving the light of a fluorescent image and the number of electrons of dark noise is 10 or less.

13. A photographing apparatus as defined in claim 11, wherein
said photographing element is provided as a rear-exposure type photographing element, in which the photographing conditions are set so that at normal temperature or lower the sum of the number of electrons of readout noise produced on each pixel within the light-receiving zone receiving the light of a fluorescent image and the number of electrons of dark noise is 20 or less.

14. A photographing apparatus as defined in claim 11, 12 or 13, wherein
the image focusing means focuses said fluorescent image in a manner in which the number of pixels of the light-receiving zone receiving the light of the fluorescent image is 40,000 or less.

15. A photographing apparatus as defined in claim 11, 12 or 13, wherein
said image focusing means is capable of changing, corresponding to the quantity of light of said fluorescent image received at said photographing element, the size of the fluorescent image focused on the light-receiving zone of said photographing element.

16. A photographing apparatus as defined in claim 11, 12 or 13, wherein
said photographing means is capable of reading out in a random manner the signal charge stored on each pixel, and sets a readout zone narrower than the light-receiving zone and which contains the fluorescent image within the light-receiving zone, and
said photographing means is provided with a readout control means for carrying out read out of said readout zone prior to readout of other zones within the light-receiving zone.

17. A photographing apparatus as defined in claim 14 wherein
said photographing means is capable of reading out in a random manner the signal charge stored on each pixel, and sets a readout zone narrower than the light-receiving zone and which contains the fluorescent image within the light-receiving zone, and
said photographing means is provided with a readout control means for carrying out read out of said readout zone prior to readout of other zones within the light-receiving zone.

18. A photographing apparatus as defined in claim 15 wherein
said photographing means is capable of reading out in a random manner the signal charge stored on each pixel, and sets a readout zone narrower than the light-receiving zone and which contains the fluorescent image within the light-receiving zone, and
said photographing means is provided with a readout control means for carrying out read out of said readout zone prior to readout of other zones within the light-receiving zone.

19. A photographing apparatus as defined in claim 15 wherein
said photographing means is capable of reading out in a random manner the signal charge stored on each pixel, and sets a readout zone narrower than the light-receiving zone and which contains the fluorescent image within the light-receiving zone, and
said photographing means is provided with a readout control means for carrying out read out of said readout zone prior to readout of other zones within the light-receiving zone, which is also capable of changing the size of said readout zone.

20. A photographing apparatus as defined in claim 11, 12 or 13, wherein
said photographing element sequentially reads out the signal charge stored on each pixel, and is structured so that said fluorescent image is assembled at the closest position of the readout port of said photographing element within said light-receiving zone.

21. A photographing apparatus as defined in claim 14 wherein
said photographing element sequentially reads out the signal charge stored on each pixel, and is structured so that said fluorescent image is assembled at the closest position of the readout port of said photographing element within said light-receiving zone.

22. A photographing apparatus as defined in claim 15 wherein said photographing element sequentially reads out the signal charge stored on each pixel, and is structured so that said fluorescent image is assembled at the closest position of the readout port of said photographing element within said light-receiving zone.

23. A photographing apparatus as defined in claim 15 wherein said photographing element sequentially reads out the signal charge stored on each pixel, and said photographing element is provided with an focusing-position changing means capable of changing the position at which said fluorescent image is assembled within said light-receiving zone.

24. A photographing method as defined in claim 1 or 2, wherein the photographing element is a charge-amplifier type photographing element for amplifying the charge by impact ionization.

25. A photographing apparatus as defined in claim 11, 12 or 13, wherein the photographing element is a charge-amplifier type photographing element for amplifying the charge by impact ionization.

* * * * *

UNITED STATES PATENT AND TRADEMARK OFFICE
CERTIFICATE OF CORRECTION

PATENT NO.    : 6,760,058 B2
DATED         : July 6, 2004
INVENTOR(S)   : Kazuo Hakamata It is certified that error appears in the above-identified patent and that said Letters Patent is hereby corrected as shown below:

<u>Title page,</u>
Item [*] Notice, "Subject to any disclaimer, ther term of the this patent is extended or adjusted under 35 U.S.C. 154(b) by 433 days." should read -- Subject to any disclaimer, ther term of this patent is extended or adjusted under 35 U.S.C. 154(b) by 512 days. --.

Signed and Sealed this

Eighteenth Day of October, 2005

JON W. DUDAS
*Director of the United States Patent and Trademark Office*